United States Patent
Halazy et al.

(10) Patent No.: US 6,770,656 B2
(45) Date of Patent: Aug. 3, 2004

(54) AMINE DERIVATIVES FOR THE TREATMENT OF APOPTOSIS

(75) Inventors: Serge Halazy, Vetraz Monthoux (FR); Matthias Schwarz, Thonex (CH); Bruno Antonsson, Billiat (CH); Agnes Bombrun, Monnetier-Mornex (FR); Jean-Claude Martinou, Versonnex (FR); Dennis Church, Commugny (CH)

(73) Assignee: Applied Research Systems ARS Holding N.V., Curacao (NL)

( * ) Notice: Subject to any disclaimer, the term of this patent is extended or adjusted under 35 U.S.C. 154(b) by 0 days.

(21) Appl. No.: 10/182,745

(22) PCT Filed: Feb. 13, 2001

(86) PCT No.: PCT/EP01/01579
§ 371 (c)(1),
(2), (4) Date: Dec. 26, 2002

(87) PCT Pub. No.: WO01/60798
PCT Pub. Date: Aug. 23, 2001

(65) Prior Publication Data
US 2003/0216427 A1 Nov. 20, 2003

(30) Foreign Application Priority Data
Feb. 15, 2000 (EP) .................................. 00810128

(51) Int. Cl.$^7$ ................ C07D 213/04; A61K 31/47
(52) U.S. Cl. ................ 514/307; 514/330; 514/371; 514/423; 546/146; 546/225; 548/200; 548/542
(58) Field of Search ................ 546/146, 225; 548/200, 542; 514/307, 330, 371, 423

(56) References Cited

FOREIGN PATENT DOCUMENTS

| WO | 92 00278 | 1/1992 |
|---|---|---|
| WO | 92 19593 | 11/1992 |
| WO | 95 12581 | 5/1995 |
| WO | 96/06863 | 3/1996 |
| WO | 97 31898 | 9/1997 |

OTHER PUBLICATIONS

Michael D. Jacobson: "Apoptosis: Bcl–2–related proteins get connected" Current Biology, vol. 7, pp. R277–R281 1997.
Guido Kroemer: "The proto–oncogene Bcl–2 and its role in regulating apoptosis" Nature Medicine, vol. 3, No. 6, pp. 614–620 06/97.
John C. Reed: "Double identify for proteins of the Bcl–2 family" Nature, vol. 387, pp. 773–776, Jun. 19, 1997.
Ameeta Kelekar et al.: "Bcl–2–family proteins: the role of the BH3 domain in apoptosis" Trends in Cell Biology, vol. 8, pp. 324–330 08/98.
Isabelle Marinou et al.: "Viral proteins E1B19K and p35 protect sympathetic neurons from cell death induced by NGF deprivation" The Journal of Cell Biology, vol. 128, No. 1–2, pp. 201–208 01/95.
Thomas L. Deckwerth et al.: "Bax is required for neuronal death after trophic factor deprivation and during development" Neuron, vol. 17, pp. 401–411 09/96.
Gloria I. Perez et al.: "Prolongation of ovarian lifespan into advanced chronological age by Bax–deficiency" Nature Genetics, vol. 21, pp. 200–203 02/99.

*Primary Examiner*—Zinna Northington Davis
(74) *Attorney, Agent, or Firm*—Oblon, Spivak, McClelland, Maier & Neustadt, P.C.

(57) ABSTRACT

The present invention is related to substituted amine derivatives notably for use as pharmaceutically active compounds, as well as to pharmaceutical formulations containing such amine derivatives of formula (I). Said substituted amine derivatives are efficient modulators, in particular inhibitors, of the Bax function and/or activation. The present invention is furthermore related to novel substituted amine derivatives as well as methods of their preparation.

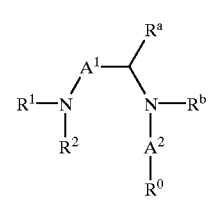

40 Claims, No Drawings

AMINE DERIVATIVES FOR THE TREATMENT OF APOPTOSIS

FIELD OF THE INVENTION

The present invention is related to new substituted amine derivatives for use as pharmaceutically active compounds, as well as pharmaceutical formulations containing such substituted amine derivatives. The pharmaceutically active compounds according to the present invention are useful for the treatment and/or prevention of disorders associated with apoptosis, including neurodegenerative disorders, diseases associated with polyglutamine tracts, epilepsy, ischemia, infertility, cardiovascular disorders, renal hypoxia, hepatitis and AIDS. Said amine derivatives display a modulatory and most notably an inhibitory activity of the cellular death agonist Bax and/or the activation pathways leading to Bax and allows therefore to block the release of cytochrome c. The present invention is furthermore related to novel pharmaceutically active substituted amino derivatives as well as to methods of their preparation.

BACKGROUND OF THE INVENTION

Apoptosis denotes the complex contortions of the membrane and organelles of a cell as it undergoes the process of programmed cell death. During said process, the cell activates an intrinsic suicide program and systematically destroys itself in a controlled manner or by a self-regulated process. The following series of events can be observed:

The cell surface begins to bleb and expresses pro-phagocytic signals. The whole apoptotic cell then fragments into membrane-bound vesicles that are rapidly and neatly disposed of by phagocytosis, so that there is minimal damage to the surrounding tissue.

The cell then separates from its neighbors.

The nucleus also goes through a characteristic pattern of morphological changes as it commits genetic suicide. The chromatin condenses and is specifically cleaved to fragments of DNA.

Neuronal cell death plays an important role in ensuring that the nervous system develops normally. It appears that the death of developing neurons depends on the size of the target that they innervate: cells with fewer synaptic partners are more likely to die than those that have formed multiple synapses. This may reflect a process, which balances the relative number of pre- to postsynaptic neurons in the developing nervous system. Although neuronal cell death is assumed to be apoptotic, it is only recently that neurons in developing rodent brain were conclusively shown to undergo apoptosis as classified by morphology and DNA fragmentation.

Neuronal death occurs via either apoptotic or necrotic processes following traumatic nerve injury or during neurodegenerative diseases. Multiple components are emerging as key players having a role in driving neuronal programmed cell death. Amongst the components leading to neuronal apoptosis are protein members belonging to the Bcl-2 family (see Jacobson, M. D. 1997. *Current Biology* 7:R 277–R281; Kroemer, G. C. 1997. *Nature Medicine*: 614–620; Reed, J. C. 1997. *Nature* 387:773–776).

Bcl-2 is a 26 kDa protein that localizes to the mitochondrial, endoplasmatic reticulum and perinuclear membranes. It is known by a person skilled in the art that the entire Bcl-2 family comprises both anti-apoptotic (Bcl-2, Bcl-$x_L$, Bcl-w, Mcl-1, A1, NR-13, BHRF1, LMW5-HL, ORF16, KS-Bcl-2, E1B-19K, CED-9) and pro-apoptotic (Bax, Bak, Bok, Bik, Blk, Hrk, BNIP3, $Bim_L$, Bad, Bid, EGL-1) molecules (see Kelekar, A., and C. B. Thompson 1998. *Trends in Cell Biology* 8:324–330). Said proteins can form homo- and hetero-dimers that involve amino acid sequences known as Bcl-2 homology (BH) domains. So far, four of said domains (BH1 to 4) have been identified, the BH3 having been attributed a particularly prominent role in view of the death-promoting cascade. Said BH3 domain of the pro-apoptotic members appears to be required for the interaction between anti and pro-apoptotic molecules. The principal site of action of some of the Bcl-2 family members seems to be the mitochondria. Mitochondria have been shown to play a major role in many types of apoptosis. In particular, this organelle has been shown to release Apoptosis Inducing Factor and cytochrome c, a hemoprotein which is bound to the outer surface of the inner mitochondrial membrane. Said cytochrome c has been shown to trigger caspase 9 activation through Apaf-1/caspase 9 complex formation. Bcl-2 family members play a key role in regulating cytochrome c release. While Bcl-2 and Bcl-$x_L$ have been shown to suppress cytochrome c release, Bax has been found to stimulate this event both in vitro using isolated mitochondria as well as in intact cells following heterologous expression (Martinou et al.; 1995 *The Journal of Cell Biology*, 128, 201–208). The mechanisms by which these proteins perform their function are currently unknown. The three-dimensional structure of Bcl-xL and Bid revealed structural similarities between these proteins and the channel-forming domains of the bacterial toxins colicins and diphtheria toxins. Consistent with such structural similarity, some members of this family including Bax were also found able to form ion channels in synthetic lipid membranes. The channel forming activity of these proteins has not yet been demonstrated in vivo.

Studies performed with Bax-deficient mice led to the conclusion that Bax plays a prominent role within the apoptosis pathways, notably in neuronal apoptosis. Bax is viewed to be essential for apoptosis induced by NGF deprivation in neonatal sympathetic neurons or for apoptosis induced in cerebellar granule cells by potassium deprivation from the culture medium. Moreover, it was found that in the Bax-deficient mice (knock-out) neonatal moto-neurons from the facial nucleus can survive following axotomy (see Deckwerth, T. L., Elliott J. L., Knudson C. M. et al. 1996. *Neuron* 17, 401–41). Hence, the inhibition of the Bax activity leading to the prevention of cytochrome c release from mitochondria during apoptosis, is viewed to be useful to protect neurons and also other cell types from various cell death stimuli.

In WO 97/01635 (Neurex Corp.) the inhibition of apoptosis in an effort to promote cell survival is suggested to be achieved by introducing into the cell a chimeric gene containing a polynucleotide encoding a Bax-ω-polypeptide being operably linked to a promoter effective to cause transcription of the polynucleotide in the cell. It is reported that the expression of the Bax-ω-polypeptide is effective to inhibit apoptosis in the cell.

WO 96/06863 claims agents for inducing apoptosis, notably for cancer therapy. Such agents interact with extracellular or cell surface membrane bound opiod-like molecules or their receptors. Such agents may be coupled to peptides which assist in the transport of the agents through the cell membrane to promote internalisation and accumulation in the cell nucleus if this is the site at which the agent produces apoptosis.

Perez et al. in *Nat. Genet.* 1999, 21(2), 200–203 have indicated that apoptosis plays a fundamental role in follicular atresia and they suggest to selectively disrupt the Bax function in order to extend the ovarian lifespan.

Bax inhibition could indeed represent an interesting therapy for all diseases associated with apoptosis, including neurodegenerative diseases (e.g. Alzheimer's disease, Parkinson's disease, diseases associated with polyglutamine tracts including Huntington's disease, spinocerebellar ataxias and dentatorubral-pallidoluysian atrophy; amyotrophic lateral sclerosis, retinitis pigmentosa and multiple sclerosis, epilepsy), ischemia (stroke, myocardial infarction and reperfusion injury), infertility (like pre-mature menopause, ovarian failure or follicular atresia), cardiovascular disorders (arteriosclerosis, heart failure and heart transplantation), renal hypoxia, hepatitis and AIDS.

Hence, it is an objective of the present invention to provide compounds enabling the treatment of a whole variety of apoptosis-related disorders, including notably the above mentioned diseases. It is specifically an objective of the present invention to provide a treatment of apoptosis related disorders by specifically modulating, e.g. by inhibiting, the Bax function or by inhibiting the Bax activation.

It is notably an objective of the present invention to provide relatively small molecule pharmaceuticals, more specifically non-proteinaceous molecules that avoid essentially all of the drawbacks arising from the use of large bio-peptides or bio-proteins (e.g. their restricted bio-availability as well as problems arising from possible in vivo intolerance), however, which are suitable for the treatment of diseases associated with abnormal apoptosis. It is particularly an objective of the present invention to provide relatively small molecule chemical compounds which are suitable Bax modulators (e.g. compounds inhibiting the Bax function or inhibiting the Bax activation) so to be available for a convenient method of treating diseases involving abnormal apoptosis. Moreover, it is an objective of the present invention to provide methods for preparing said small molecule chemical compounds. It is furthermore an objective of the present invention to provide new pharmaceutical formulations for the treatment of diseases which are caused by abnormal apoptosis, more specifically by Bax. It is finally an objective of the present invention to provide a method of treating diseases that are caused by abnormal apoptosis.

DESCRIPTION OF THE INVENTION

The aforementioned objectives have been met according to the independent claims which are set out hereinafter in the description. Preferred embodiments are set out within the de-pendent claims.

The following paragraphs provide definitions of the various chemical moieties that make up the compounds according to the invention and are intended to apply uniformly through-out the specification and claims unless an otherwise expressly set out definition provides a broader definition.

"$C_1$–$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenantrenyl and the like.

"$C_1$–$C_6$-alkyl aryl" refers to $C_1$–$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl,1,3,4-triazinyl, 1,2,3-triazinyl, benzofuryl, [2,3-dihydro] benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnnolinyl, napthyridinyl, pyrido[3,4-b] pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetra-hydroisoquinolyl, purinyl, pteridinyl, carbazolyl, xanthenyl or benzoquinolyl.

"$C_1$–$C_6$-alkyl heteroaryl" refers to $C_1$–$C_6$-alkyl groups having a heteroaryl substituent, including 2-furylmethyl, 2-thienylmethyl, 2-(1H-indol-3-yl)ethyl and the like.

"Alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"Alkynyl" refers to alkynyl groups preferably having from 2 to 6 carbon atoms and having at least 1–2 sites of alkynyl unsaturation, preferred alkynyl groups include ethynyl (—C≡CH), propargyl (—$CH_2$C≡CH), and the like.

"Acyl" refers to the group —C(O)R where R includes "$C_1$–$C_6$-alkyl", "aryl", "heteroaryl", "$C_1$–$C_6$-alkyl aryl" or "$C_1$–$C_6$-alkyl heteroaryl".

"Acyloxy" refers to the group —OC(O)R where R includes "$C_1$–$C_6$-alkyl", "aryl", "heteroaryl", "$C_1$–$C_6$-alkyl aryl" or "$C_1$–$C_6$-alkyl heteroaryl".

"Alkoxy" refers to the group —O—R where R includes "$C_1$–$C_6$-alkyl" or "aryl" or "hetero-aryl" or "$C_1$–$C_6$-alkyl aryl" or "$C_1$–$C_6$-alkyl heteroaryl". Preferred alkoxy groups include by way of example, methoxy, ethoxy, propoxy, butoxy, phenoxy and the like.

"Alkoxycarbonyl" refers to the group —C(O)OR where R includes "$C_1$–$C_6$-alkyl" or "aryl" or "heteroaryl" or "$C_1$–$C_6$-alkyl aryl" or "$C_1$–$C_6$-alkyl heteroaryl".

"Aminocarbonyl" refers to the group —C(O)NRR' where each R, R' includes independently hydrogen or $C_1$–$C_6$-alkyl or aryl or heteroaryl or "$C_1$–$C_6$-alkyl aryl" or "$C_1$–$C_6$-alkyl heteroaryl".

"Acylamino" refers to the group —NR(CO)R' where each R, R' is independently hydrogen or "$C_1$–$C_6$-alkyl" or "aryl" or "heteroaryl" or "$C_1$–$C_6$-alkyl aryl" or "$C_1$–$C_6$-alkyl heteroaryl".

"Halogen" refers to fluoro, chloro, bromo and iodo atoms.

"Sulfonyl" refers to group "—$SO_2$—R" wherein R is selected from H, "aryl", "heteroaryl", "$C_1$–$C_6$-alkyl", "$C_1$–$C_6$-alkyl" substituted with halogens e.g. an —$SO_2$—$CF_3$ group, "$C_1$–$C_6$-alkyl aryl" or "$C_1$–$C_6$-alkyl heteroaryl".

"Sulfoxy" refers to a group "—S(O)—R" wherein R is selected from H, "$C_1$–$C_6$-alkyl", "$C_1$–$C_6$-alkyl" substituted with halogens e.g. an —SO—$CF_3$ group, "aryl", "heteroaryl", "$C_1$–$C_6$-alkyl aryl" or "$C_1$–$C_6$-alkyl heteroaryl".

"Thioalkoxy" refers to groups —S—R where R includes "$C_1$–$C_6$-alkyl" or "aryl" or "hetero-aryl" or "$C_1$–$C_6$-alkyl aryl" or "$C_1$–$C_6$-alkyl heteroaryl". Preferred thioalkoxy groups include thiomethoxy, thioethoxy, and the like.

"Substituted or unsubstituted": Unless otherwise constrained by the definition of the individual substituent, the above set out groups, like "alkyl", "alkenyl", "alkynyl", "aryl" and "heteroaryl" etc. groups may optionally be substituted with from 1 to 5 substituents selected from the group consisting of "$C_1$–$C_6$-alkyl", "$C_1$–$C_6$-alkyl aryl", "$C_1$–$C_6$-alkyl heteroaryl", "$C_2$–$C_6$-alkenyl", "$C_2$–$C_6$-alkynyl", primary, secondary or tertiary amino groups or quaternary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Alternatively, said substitution could also comprise situations where neighboring substituents have undergone ring closure, notably when viccinal functional substituents are involved, thus forming e.g. lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formula I that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, trifluoroacetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and polygalacturonic acid. Said compounds can also be administered as pharmaceutically acceptable quaternary salts known by a person skilled in the art, which specifically include the quarternary ammonium salt of the formula —NR,R',R"$^+$Z$^-$, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an essentially enantiomeric synthesis or a synthesis comprising an enantioselective step, whereby a surplus of one enantiomer in the order of at least about 52% ee is yielded. In the absence of an enantiomeric synthesis, racemic products are usually obtained that do however also have the inventive set out activity as Bax inhibitors.

It was now found that compounds according to formula I are suitable pharmaceutically active agents, notably by effectively modulating the Bax function or the Bax activation.

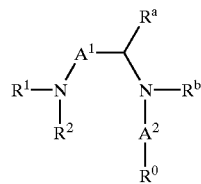

I $A^1$ $A^2$ are selected independently from each other from the group consisting of —C(O)— and —SO$_2$—.

$R^a$ is $C_1$–$C_{10}$ alkyl, $R^b$ is CH$_3$, or $R^a$ and $R_b$ taken together with the atoms to which they are attached form a five-membered saturated ring optionally containing a sulfur atom or a six-membered saturated ring optionally fused with an aryl or heteroaryl group.

$R^1$ is either H or $C_1$–$C_6$ alkyl.

$R^2$ is —($R^d$–$X_1$)$_m$—$R^e$ wherein m is an integer from 0 to 8.

Therein, $R^d$ is selected of aryl, heteroaryl, $C_1$–$C_{18}$ alkyl, 3–8-membered cycloalkyl, $C_2$–$C_{18}$ alkenyl or 3–8-membered cycloalkenyl, $C_2$–$C_{18}$ alkynyl.

$X_1$ is a bond, O, NH, NR$^g$, NR$^g$N$^{g'}$, S, Si(R$^g$R$^{g'}$), SO, SO$_2$, wherein R$^g$ and R$^{g'}$ are independently selected from the group consisting of substituted or unsubstituted $C_1$–$C_6$ alkyl, $C_2$–$C_8$ alkenyl, $C_2$–$C_8$ alkynyl, aryl or heteroaryl.

$R^e$ is selected of aryl-$C_1$–$C_{18}$ alkyl, aryl-$C_2$–$C_{18}$ alkenyl, aryl-$C_2$–$C_{18}$ alkynyl, heteroaryl-$C_1$–$C_{18}$ alkyl, heteroaryl-$C_2$–$C_{18}$ alkenyl, heteroaryl-$C_2$–$C_{18}$ alkynyl, $C_1$–$C_{18}$ alkyl, $C_2$–$C_{18}$ alkenyl, $C_2$–$C_{18}$ alkynyl. All of said $C_1$–$C_{18}$ alkyl, $C_2$–$C_{18}$ alkenyl and $C_2$–$C_{18}$ alkynyl groups have a terminal substituent of the formula —NRR' or —N$^+$RR'R" wherein R, R', R" are selected independently from each other of H, $C_1$–$C_6$-alkyl. Preferred $C_1$–$C_6$-alkyl are methyl and ethyl.

Alternatively, at least 2 of R, R' and R" form a 3–12 membered cyclic or bicyclic ring. A terminal ammonium moiety of the formula —N$^+$RR'R", with all groups R, R'and R" being organic residues represents one preferred embodiment. Another particularly preferred terminal amino group —NRR' is —NH$_2$.

Also $R^1$ and $R^2$ together with the N atom to which they are attached could form an unsubstituted or substituted 4–12 membered unsaturated or saturated ring containing one further heteroatom selected from O, N. Said ring may optionally be substituted by a substituent of the formula —NRR' or —N$^+$RR'R" or $R^e$, whereby a substituent $R^e$, as defined above.

$R^0$ is $R^f$—$X_2$—$R^{f'}$ wherein $R^f$ and $R^{f'}$ are independently from each other selected from the group consisting of aryl, heteroaryl, 3–8-membered cycloalkenyl, 3–8-membered cycloalkyl, $C_2$–$C_{18}$ alkyl, $C_2$–$C_{18}$ alkenyl, $C_2$–$C_{18}$ alkynyl, aryl-$C_1$–$C_{18}$ alkyl, aryl-$C_2$–$C_{18}$ alkenyl, aryl-$C_2$–$C_{18}$ alkynyl, heteroaryl-$C_1$–$C_{18}$ alkyl, heteroaryl-$C_2$–$C_{18}$ alkenyl, heteroaryl-$C_2$–$C_{18}$ alkynyl.

$X_2$ is a bond or O, S, Si(R$^g$R$^{g'}$), SO, SO$_2$, wherein R$^g$ and R$^{g'}$ are independently selected from the group consisting of substituted or unsubstituted $C_1$–$C_6$ alkyl, $C_2$–$C_8$ alkenyl, $C_2$–$C_8$ alkynyl, aryl or heteroaryl.

The present invention also includes the pharmaceutically acceptable salts, e.g. hydrates, acid addition salts thereof, as well as the pharmaceutically active derivatives of compounds of formula I. Preferred pharmaceutically acceptable salts of the compound I, are acid addition salts formed with pharmaceutically acceptable acids like hydrochloride, hydrobromide, trifluoroacetate, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

According to a preferred embodiment of the invention, $A^1$ and $A^2$ are each carbonyl (C═O) thus providing preferred compounds as illustrated by the below formula IA:

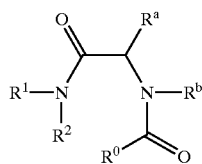

IA wherein $R^0$, $R^1$, $R^2$, $R^a$ and $R^b$ are as above-defined.

It was unexpectedly found that the above set out compounds according to formula I are suitable modulators of the Bax function. Thereby, the preferred compounds of formula (I) are those where $R^0$ represents a a $C_8$–$C_{18}$ alkyl group more preferred $R^0$ is a $C_{10}$–$C_{18}$ alkyl group and most preferred is a $C_{12}$-alkyl group.

At the same time, according to one preferred embodiment, $R^2$ is a long alkyl chain, preferably with $R^e$ being a $C_{10}$–$C_{18}$ alkyl having a terminal amino group NRR' or OR, particularly preferred is a $C_{10}$–$C_{18}$ alkyl having a terminal $NH_2$ group or OH group. Also, a terminal quarternary ammonium moiety of the formula —$N^+RR'R''$ of $R^2$ wherein each R, R', R'' are a $C_1$–$C_6$-alkyl or which form a cyclic or bicyclic ring is one embodiment of the invention.

According to a further preferred embodiment, $R^a$ and $R^b$ form either a five-membered saturated ring, optionally containing a sulfur atom, or a six-membered saturated ring wherein said ring may be fused with an unsubstituted phenyl group.

Preferred rings following to ring closure of $R^a$ and $R^b$ are pyrrolidinyl, piperidinyl, a fused piperidinyl, e.g. a tetrahydroisoquinolinyl (TIQ) or 1,3-thiazolidinyl.

Particularly preferred amine derivatives are those wherein $R^1$ is H or $CH_3$, most preferred H, $R^2$ is —$(R^d$—$X_1)_m$—$R^e$ in which $R^d$—$X_1$ is —$(CH_2)_2$—O— or a bond, $R^e$ is $C_1$–$C_{10}$-alkylamine, most preferred $R^2$ is $C_2$–$C_8$ alkylamine. Specific examples for $R^2$ is ethylenamine, hexylenamine or heptylenamine.

Particularly preferred amine derivatives are those wherein $R^0$ is selected from the group consisting of $C_4$–$C_{18}$ alkyl having optionally a terminal cyclohexyl group. Particularly preferred $R^0$ is $C_8$–$C_{18}$ alkyl, more preferred $C_{10}$–$C_{18}$ alkyl and most preferred $C_{12}$ alkyl. Further specific examples of $R^0$ are —$CH_2$-phenyl-O—$CH_2$-phenyl or —$CH_2$—Ph—Ph.

Where $R^a$ and $R^b$ form a five-membered saturated ring, optionally containing a sulfur atom, or a six-membered saturated ring optionally, optionally fused with an unsubstituted phenyl group, then preferably $A^1$ and $A^2$ are each (C=O) and $R^0$ is an unsubstituted $C_4$–$C_{16}$ alkyl having optionally a terminal cyclohexyl group or —$CH_2$—Ph—O—$CH_2$—Ph or $CH_2$—Ph—Ph, $R^1$ is H or —$CH_3$, $R^2$ is —$(R^d$—$X_1)_m$—$R^e$ wherein $R^d$—$X_1$ is —$(CH_2)_2$—O— with m being 0 or 2, $R^e$ is an unsubstituted $C_2$–$C_8$-alkylamine, more preferred a $C_2$–$C_7$ alkylamine and most preferred a hexylenamine.

A particularly preferred embodiment is wherein $R^a$ and $R^b$ form a piperidinyl, pyrrolidinyl or thiazolidinyl ring optionally fused with an unsubstituted phenyl group, $A^1$ and $A^2$ are each C=O, $R^0$ is an unsubstituted $C_4$ or $C_{12}$ alkyl chain, $R^1$ is H or $CH_3$, $R^2$ is —$(R^d$—$X_1)_m$—$R^e$ wherein m is 0 and $R^e$ is $C_2$–$C_8$ alkylamine.

Where $R^a$ and $R^b$ do not form any ring, a preferred embodiment of the amine derivative according to the present invention is wherein $R^b$ is $CH_3$, $R^a$ is iPr, $A^1$ and $A^2$ are each C=O, $R^0$ is $C_4$–$C_{15}$ alkyl, preferably a dodecyl group, $R^1$ is H, $R^2$ is —$(R^d$—$X_1)_m$—$R^e$ wherein m is 0, $R^e$ is $C_4$–$C_{10}$, particularly $C_6$ alkylamine.

The compounds of formula I may contain one or more asymmetric centers and may therefore exist as enantiomers or diastereoisomers. It is to be understood that the invention includes both mixtures and separate individual isomers or enantiomers of the compounds of formula I. In a particularly preferred embodiment the compounds according to formula I are obtained in an enantiomeric excess of at least 52% ee, preferably of at least 92–98% ee.

Specific examples of compounds of formula I include the following:

(S)-1-Tridecanoyl-piperidine-2-carboxylic acid (6-amino-hexyl)-amide (R)-1-Tridecanoyl-piperidine-2-carboxylic acid (6-amino-hexyl)-amide (±)-N-(6-Aminohexyl)-1-{[(2-{[2-(methyloxy)ethyl]oxy}ethyl)oxy]acetyl}piperidine-2-carboxamide (±)-N-(6-Aminohexyl)-1-(4-cyclohexylbutanoyl)piperidine-2-carboxamide (±)-N-(6-Aminohexyl)-1-([1,1'-biphenyl]-4-ylacetyl)piperidine-2-carboxamide (±)-N-(6-Aminohexyl)-1-({4-[(phenylmethyl)oxy]phenyl}acetyl)piperidine-2-carboxamide (S)-N-(6-Aminohexyl)-1-tridecanoylpyrrolidine-2-carboxamide (R)-N-(6-Aminohexyl)-1-tridecanoylpyrrolidine-2-carboxamide (±)-N-(6-Aminohexyl)-1-{[(2-{[2-(methyloxy)ethyl]oxy}ethyl)oxy]acetyl}pyrrolidine-2-carboxamide (±)-N-(6-Aminohexyl)-1-(4-cyclohexylbutanoyl)pyrrolidine-2-carboxamide (±)-N-(6-Aminohexyl)-1-([1,1'-biphenyl]-4-ylacetyl)pyrrolidine-2-carboxamide (±)-N-(6-Aminohexyl)-1-({4-[(phenylmethyl)oxy]phenyl}acetyl)pyrrolidine-2-carboxamide (±)-N-(6-Aminohexyl)-3-tridecanoyl-1,3-thiazolidine-4-carboxamide (±)-N-(6-Aminohexyl)-3-{[(2-{[2-(methyloxy)ethyl]oxy}ethyl)oxy]acetyl}-1,3-thiazolidine-4-carboxamide (±)-N-(6-Aminohexyl)-3-(4-cyclohexylbutanoyl)-1,3-thiazolidine-4-carboxamide (±)-N-(6-Aminohexyl)-3-([1,1'-biphenyl]-4-ylacetyl)-1,3-thiazolidine-4-carboxamide (±)-N-(6-Aminohexyl)-3-({4-[(phenylmethyl)oxy]phenyl}acetyl)-1,3-thiazolidine-4-carboxamide (±)-N-(6-Aminohexyl)-2-tridecanoyl-1,2,3,4-tetrahydroisoquinoline-3-carboxamide (±)-N-(6-Aminohexyl)-2-{[(2-{[2-(methyloxy)ethyl]oxy}ethyl)oxy]acetyl}-1,2,3,4-tetrahydroisoquinoline-3-carboxamide (±)-N-(6-Aminohexyl)-2-(4-cyclohexylbutanoyl)-1,2,3,4-tetrahydroisoquinoline-3-carboxamide (±)-N-(6-Aminohexyl)-2-([1,1'-biphenyl]-4-ylacetyl)-1,2,3,4-tetrahydroisoquinoline-3-carboxamide (±)-N-(6-Aminohexyl)-2-({4-[(phenylmethyl)oxy]phenyl}acetyl)-1,2,3,4 tetrahydroisoquinoline-3-carboxamide (S)-N-(1-{[(6-Aminohexyl)amino]carbonyl}-2-methylpropyl)-N-methyltridecanamide (±)-N-(6-Aminohexyl)-11-methyl-12-(1-methylethyl)-10-oxo-2,5,8-trioxa-11-azatridecan-13-amide (±)-N-(6-Aminohexyl)-2-[(4-cyclohexylbutanoyl)(methyl)amino-3-methylbutanamide (±)-N-(6-Aminohexyl)-2-[([ 1,1'-biphenyl]-4-ylacetyl)(methyl)amino]-3-methylbutanamide (±)-N-(6-Aminohexyl)-3-methyl-2-[methyl({4-[(phenylmethyl)oxy]phenyl}acetyl)amino]-butanamide (±)-N-(5-Aminopentyl)-1-tridecanoylpiperidine-2-carboxamide (±)-N-(5-Aminopentyl)-1-{[(2-{[2-(methyloxy)ethyl]oxy}ethyl)oxy]acetyl}piperidine-2-carboxamide (±)-N-(5-Aminopentyl)-1-(4-cyclohexylbutanoyl)piperidine-2-carboxamide (±)-N-(5-Aminopentyl)-1-([1,1'-biphenyl]-4-ylacetyl)piperidine-2-carboxamide (±)-N-(5-Aminopentyl)-1-({4-[(phenylmethyl)oxy]phenyl}acetyl)piperidine-2-carboxamide (±)-N-(5-Aminopentyl)-1-tridecanoylpyrrolidine-2-carboxamide (R)-N-(5-Aminopentyl)-1-tridecanoylpyrrolidine-2-carboxamide (S)-N-(5-Aminopentyl)-1-tridecanoylpyrrolidine-2-carboxamide (±)-N-(5-Aminopentyl)-1-{[(2-{[2-(methyloxy)ethyl]oxy}ethyl)oxy]acetyl}pyrrolidine-2-carboxamide (±)-N-(5-Aminopentyl)-1-(4-cyclohexylbutanoyl)pyrrolidine-2-carboxamide (±)-N-(5-Aminopentyl)-1-([1,1'-biphenyl]-4-ylacetyl)pyrrolidine-2-carboxamide (±)-N-(5-Aminopentyl)-1-({4-[(phenylmethyl)oxy]phenyl}acetyl)pyrrolidine-2-carboxamide (±)-N-(5-Aminopentyl)-3-tridecanoyl-1,3-thiazolidine-4-carboxamide (±)-N-(5-Aminopentyl)-3-{[(2-{[2-(methyloxy)ethyl]oxy}ethyl)oxy]acetyl}-1,3-thiazolidine-4-carboxamide (±)-N-(5-Aminopentyl)-3-(4-cyclohexylbutanoyl)-1,3-thiazolidine-4-carboxamide (±)-N-(5-Aminopentyl)-3-([1,1'-biphenyl]-4-ylacetyl)-1,3-thiazolidine-4-carboxamide (±)-N-(5-Aminopentyl)-3-({4-[(phenylmethyl)oxy]phenyl}acetyl)-1,3-thiazolidine-4-carboxamide (±)-N-(5-Aminopentyl)-2-tridecanoyl-1,2,3,4-tetrahydroisoquinoline-3-carboxamide (±)-N-(5-Aminopentyl)-2-{[(2-{[2-(methyloxy)ethyl]oxy}ethyl)oxy]acetyl}-1,2,3,4-tetrahydroisoquinoline-3-carboxamide (±)-N-((5-Aminopentyl)-2-(4-cyclohexylbutanoyl)-1,2,3,4-tetrahydroisoquinoline-3-carboxamide (±)-N-(5-Aminopentyl)-2-([1,1'-biphenyl]-4-ylacetyl)-1,2,3,4-tetrahydroisoquinoline-3-carboxamide (±)-N-(5-Aminopentyl)-2-({4-[(phenylmethyl)oxy]phenyl}acetyl)-1,2,3,4-tetrahydroisoquinoline-3-carboxamide (±)-N-(1-{[(5-Aminopentyl)amino]carbonyl}-2-methylpropyl)-N-methyltridecanamide (±)-N-(5-Aminopentyl)-11-methyl-12-(1-methylethyl)-10-oxo-2,5,8-trioxa-11-azatridecan-13-amide (±)-N-(5-Aminopentyl)-2-[(4-cyclohexylbutanoyl)(methyl)amino]-3-methylbutanamide (±)-N-(5-Aminopentyl)-2-[([1,1'-biphenyl]-4-ylacetyl)(methyl)amino]-3-methylbutanamide (±)-N-(5-Aminopentyl)-3-methyl-2-[methyl({4-[(phenylmethyl)oxy]phenyl}acetyl)amino]-butanamide (±)-N-(7-Aminoheptyl)-1-tridecanoylpiperidine-2-carboxamide (±)-N-(7-Aminoheptyl)-1-{[(2-{[2-(methyloxy)ethyl]oxy}ethyl)oxy]acetyl}piperidine-2-carboxamide (±)-N-(7-Aminoheptyl)-1-(4-cyclohexylbutanoyl)piperidine-2-carboxamide (±)-N-(7-Aminoheptyl)-1-([1,1'-biphenyl]-4-ylacetyl)piperidine-2-carboxamide (±)-N-(7-Aminoheptyl)-1-({4-[(phenylmethyl)oxy]phenyl}acetyl)piperidine-2-carboxamide (±)-N-(7-Aminoheptyl)-1-tridecanoylpyrrolidine-2-carboxamide (±)-N-(7-Aminoheptyl)-1-{[(2-{[2-(methyloxy)ethyl]oxy}ethyl)oxy]acetyl}pyrrolidine-2-carboxamide (±)-N-(7-Aminoheptyl)-1-(4-cyclohexylbutanoyl)pyrrolidine-2-carboxamide (±)-N-(7-Aminoheptyl)-1-([1,1'-biphenyl]-4-ylacetyl)pyrrolidine-2-carboxamide (±)-N-(7-Aminoheptyl)-1-({4-[(phenylmethyl)oxy]phenyl}acetyl)pyrrolidine-2-carboxamide (±)-N-(7-Aminoheptyl)-3-tridecanoyl-1,3-thiazolidine-4-carboxamide (±)-N-(7-Aminoheptyl)-3-{[(2-{[2-(methyloxy)ethyl]oxy}ethyl)oxy]acetyl}-1,3-thiazolidine-4-carboxamide (±)-N-(7-Aminoheptyl)-3-(4-cyclohexylbutanoyl)-1,3-thiazolidine-4-carboxamide (±)-N-(7-Aminoheptyl)-3-([1,1'-biphenyl]-4-ylacetyl)-1,3-thiazolidine-4-carboxamide (±)-N-(7-Aminoheptyl)-3-({4-[(phenylmethyl)oxy]phenyl} acetyl)-1,3-thiazolidine-4-carboxamide (±)-N-(7-Aminoheptyl)-2-tridecanoyl-1,2,3,4-tetrahydroisoquinoline-3-carboxamide (±)-N-(7-Aminoheptyl)-2-{[(2-{[2-(methyloxy)ethyl]oxy}ethyl)oxy]acetyl}-1,2,3,4-tetrahydroisoquinoline-3-carboxamide (±)-N-(7-Aminoheptyl)-2-(4-cyclohexylbutanoyl)-1,2,3,4-tetrahydroisoquinoline-3-carboxamide (±)-N-(7-Aminoheptyl)-2-([1,1'-biphenyl]-4-ylacetyl)-1,2,3,4-tetrahydroisoquinoline-3-carboxamide (±)-N-(7-Aminoheptyl)-2-({4-[(phenylmethyl)oxy]phenyl}acetyl)-1,2,3,4-tetrahydroisoquinoline-3-carboxamide (±)-N-(1-{[(7-Aminoheptyl)amino]carbonyl}-2-methylpropyl)-N-methyltridecanamide (±)-N-(7-Aminoheptyl)-11-methyl-12-(1-methylethyl)-10-oxo-2,5,8-trioxa-11-azatridecan-13-amide (±)-N-(7-Aminoheptyl)-2-[([1,1'-biphenyl]-4-ylacetyl)(methyl)amino]-3-methylbutanamide (±)-N-(7-Aminoheptyl)-3-methyl-2-[methyl({4-[(phenylmethyl)oxy]phenyl}acetyl)amino]-butanamide (±)-N-[2-({2-[(2-Aminoethyl)oxy]ethyl}oxy)ethyl]-1-tridecanoylpiperidine-2-carboxamide (±)-N-[2-({2-[(2-Aminoethyl)oxy]ethyl}oxy)ethyl]-1-{[(2-{[2-(methyloxy)ethyl]oxy}ethyl)oxy]acetyl}piperidine-2-carboxamide (±)-N-[2-({2-[(2-Aminoethyl)oxy]ethyl}oxy)ethyl]-1-(4-cyclohexylbutanoyl)piperidine-2carboxamide (±)-N-[2-({2-[(2-Aminoethyl)oxy]ethyl}oxy)ethyl]-1-([1,1'-biphenyl]-4-ylacetyl)piperidine-2-carboxamide (±)-N-[2-({2-[(2-Aminoethyl)oxy]ethyl}oxy)ethyl]-1-({4-[(phenylmethyl)oxy]phenyl})-acetyl) piperidine-2-carboxamide (±)-N-[2-({2-[(2-Aminoethyl)oxy]ethyl}oxy)ethyl]-1-tridecanoylpyrrolidine-2-carboxamide (±)-N-[2-({2-[(2-Aminoethyl)oxy]ethyl}oxy)ethyl]-1-{[(2-{[2-(methyloxy)ethyl]oxy}-ethyl)oxy]acetyl}pyrrolidine-2-carboxamide (±)-N-[2-({2-[(2-Aminoethyl)oxy]ethyl}oxy)ethyl]-1-(4-cyclohexylbutanoyl)pyrrolidine-2-carboxamide (±)-N-[2-({2-[(2-Aminoethyl)oxy]ethyl}oxy)ethyl]-1-([1,1'-biphenyl]-4-ylacetyl)pyrrolidine-2-carboxamide (±)-N-[2-({2-[(2-Aminoethyl)oxy]ethyl}oxy)ethyl]-1-({4-[(phenylmethyl)oxy]phenyl}-acetyl)pyrrolidine-2-carboxamide (±)-N-[2-({2-[(2-Aminoethyl)oxy]ethyl}oxy)ethyl]-3-tridecanoyl-1,3-thiazolidine-4-carboxamide (±)-N-[2-({2-[(2-Aminoethyl)oxy]ethyl}oxy)ethyl]-3-{[(2-{[2-(methyloxy)ethyl]oxy}-ethyl)oxy]acetyl}-1,3-thiazolidine-4-carboxamide (±)-N-[2-({2-[(2-Aminoethyl)oxy]ethyl}oxy)ethyl]-3-(4-cyclohexylbutanoyl)-1,3-thiazolidine-4-carboxamide (±)-N-[2-({2-[(2-Aminoethyl)oxy]ethyl}oxy)ethyl]-3-([1,1'-biphenyl]-4-ylacetyl)-1,3-thiazolidine-4-carboxamide (±)-N-[2-({2-[(2-Aminoethyl)oxy]ethyl}oxy)ethyl]-3-({4-[(phenylmethyl)oxy]phenyl}-acetyl)-1,3-thiazolidine-4-carboxamide (±)-N-[2-({2-[(2-Aminoethyl)oxy]ethyl}oxy)ethyl]-2-tridecanoyl-1,2,3,4-tetrahydroisoquinoline-3-carboxamide (±)-N-[2-({2-[(2-Aminoethyl)oxy]ethyl}oxy)ethyl]-2-{[(2-{[2-(methyloxy)ethyl]oxy}-ethyl)oxy]acetyl}-1,2,3,4-tetrahydroisoquinoline-3-carboxamide (±)-N-[2-({2-[(2-Aminoethyl)oxy]ethyl}oxy)ethyl]-2-(4-cyclohexylbutanoyl)-1,2,3,4-tetrahydroisoquinoline-3-carboxamide (±)-N-[2-({2-[(2-Aminoethyl)oxy]ethyl}oxy)ethyl]-2-([1,1'-biphenyl]-4-ylacetyl)-1,2,3,4-tetrahydroisoquinoline-3-carboxamide (±)-N-[2-({2-[(2-Aminoethyl)oxy]ethyl}oxy)ethyl]-2-({4-[(phenylmethyl)oxy]phenyl}-acetyl)-1,2,3,4-tetrahydroisoquinoline-3-carboxamide (±)-N-[1-({[2-({2-[(2-Aminoethyl)oxy]ethyl}oxy)ethyl]amino}carbonyl)-2-methylpropyl]-N-methyltridecanamide (±)-N-[2-({2-[(2-Aminoethyl)oxy]ethyl}oxy)ethyl]-11-methyl-12-(1-methylethyl)-10-oxo-2,5,8-trioxa-11-azatridecan-13-amide (±)-N-[2-({2-[(2-Aminoethyl)oxy]ethyl}oxy)ethyl]-2-[(4-cyclohexylbutanoyl)(methyl)-amino]-3-methylbutanamide (±)-N-[2-({2-[(2-Aminoethyl)oxy]ethyl}oxy)ethyl]-2-[([1,1'-biphenyl]-4-ylacetyl)(methyl)-amino]-3-methylbutanamide (±)-N-[2-({2-[(2-Aminoethyl)oxy]ethyl}oxy)ethyl]-3-methyl-2-[methyl({4-[(phenyl-methyl)oxy]phenyl}acetyl)amino]butanamide (±)-N-Methyl-N-(2-{[2-(methylamino)ethyl]oxy}ethyl)-1-{[(2-{[2-(methyloxy)ethyl]-oxy}ethyl)oxy]acetyl}piperidine-2-carboxamide (±)-N-Methyl-N-(2-{[2-(methylamino)ethyl]oxy}ethyl)-1-tridecanoylpyrrolidine-2-carboxamide (±)-N-Methyl-N-(2-{[2-(methylamino)ethyl]oxy}ethyl)-1-{[(2-{[2-(methyloxy)ethyl]-oxy}ethyl)oxy]acetyl}pyrrolidine-2-carboxamide (±)-1-(4-Cyclohexylbutanoyl)-N-methyl-N-(2-{[2-(methylamino)ethyl]oxy}ethyl)-pyrrolidine-2-carboxamide (±)-1-([1,1'-Biphenyl]-4-ylacetyl)-N-methyl-N-(2-{[2-(methylamino)ethyl]oxy}ethyl)-pyrrolidine-2-carboxamide (±)-N-Methyl-N-(2-{[2-(methylamino)ethyl]oxy}ethyl)-1-({4-[(phenylmethyl)oxy]-phenyl}acetyl)pyrrolidine-2-carboxamide (±)-N-Methyl-N-(2-{[2-(methylamino)ethyl]oxy}ethyl)-3-tridecanoyl-1,3-thiazolidine-4-carboxamide (±)-N-Methyl-N-(2-{[2-(methylamino)ethyl]oxy}ethyl)-3-{[(2-{[2-(methyloxy)ethyl]oxy}-ethyl)oxy]acetyl}-1,3-thiazolidine-4-carboxamide (±)-3-(4-Cyclohexylbutanoyl)-N-methyl-N-(2-{[2-(methylamino)ethyl]oxy}ethyl)-1,3-thiazolidine-4-carboxamide (±)-3-([1,1'-Biphenyl]-4-ylacetyl)-N-methyl-N-(2-{[2-(methylamino)ethyl]oxy}ethyl)-1,3-thiazolidine-4-carboxamide (±)-N-Methyl-N-(2-{[2-(methylamino)ethyl]oxy}ethyl)-3-({4-[(phenylmethyl)oxy]-phenyl}acetyl)-1,3-thiazolidine-4-carboxamide (±)-N-Methyl-N-(2-{[2-(methylamino)ethyl]oxy}ethyl)-2-tridecanoyl-1,2,3,4-tetrahydroisoquinoline-3-carboxamide (±)-N-Methyl-N-(2-{[2-(methylamino)ethyl]oxy}ethyl)-2-{[(2-{[2-(methyloxy)ethyl]oxy}-ethyl)oxy]acetyl}-1,2,3,4-tetrahydroisoquinoline-3-carboxamide (±)-2-(4-Cyclohexylbutanoyl)-N-methyl-N-(2-{[2-(methylamino)ethyl]oxy}ethyl)-1,2,3,4-tetrahydroisoquinoline-3-carboxamide (±)-2-([1,1'-Biphenyl]-4-ylacetyl)-N-methyl-N-(2-{[2-(methylamino)ethyl]oxy}ethyl)-1,2,3,4-tetrahydroisoquinoline-3-carboxamide (±)-N-Methyl-N-(2-{[2-(methylamino)ethyl]oxy}ethyl)-2-({4-[(phenylmethyl)oxy]-phenyl}acetyl)-1,2,3,4-tetrahydroisoquinoline-3-carboxamide (±)-N,11-Dimethyl-N-(2-{[2-(methylamino)ethyl]oxy}ethyl)-12-(1-methylethyl)-10-oxo-2,5,8-trioxa-11-azatridecan-13-amide (±)-N-Methyl-N-[6-(methylamino)hexyl]-1-{[(2-{[2-(methyloxy)ethyl]oxy}ethyl)oxy]-acetyl}piperidine-2-carboxamide (±)-N-Methyl-N-[6-(methylamino)hexyl]-1-tridecanoylpyrrolidine-2-carboxamide (±)-N-Methyl-N-[6-(methylamino)hexyl]-1-{[(2-{[2-(methyloxy)ethyl]oxy}ethyl)oxy]-acetyl}pyrrolidine-2-carboxamide (±)-1-(4-Cyclohexylbutanoyl)-N-methyl-N-[6-(methylamino)hexyl]pyrrolidine-2-carboxamide (±)-1-([1,1'-Biphenyl]-4-ylacetyl)-N-methyl-N-[6-(methylamino)hexyl]pyrrolidine-2-carboxamide (±)-N-Methyl-N-[6-(methylamino)hexyl]-1-({4-[(phenylmethyl)oxy]phenyl}acetyl)-pyrrolidine-2-carboxamide (±)-N-Methyl-N-[6-(methylamino)hexyl]-3-tridecanoyl-1,3-thiazolidine-4-carboxamide (±)-N-Methyl-N-[6-(methylamino)hexyl]-3-{[(2-{[2-(methyloxy)ethyl]oxy}ethyl)oxy]-acetyl}-1,3-thiazolidine-4-carboxamide (±)-3-(4-Cyclohexylbutanoyl)-N-methyl-N-[6-(methylamino)hexyl]-1,3-thiazolidine-4-carboxamide (±)-3-([1,1'-Biphenyl]-4-ylacetyl)-N-methyl-N-[6-(methylamino)hexyl]-1,3-thiazolidine-4-carboxamide (±)-N-Methyl-N-[6-(methylamino)hexyl]-3-({4-[(phenylmethyl)oxy]phenyl}acetyl)-1,3-thiazolidine-4-carboxamide (±)-N-Methyl-N-[6-(methylamino)hexyl]-2-tridecanoyl-1,2,3,4-tetrahydroisoquinoline-3-carboxamide (±)-N-Methyl-N-[6-(methylamino)hexyl]-2-{[(2-{[2-(methyloxy)ethyl]oxy}ethyl)oxy]-acetyl}-1,2,3,4-tetrahydroisoquinoline-3-carboxamide (±)-2-(4-Cyclohexylbutanoyl)-N-methyl-N-[6-(methylamino)hexyl]-1,2,3,4-tetrahydroisoquinoline-3-carboxamide (±)-2-([1,1'-Biphenyl]-4-ylacetyl)-N-methyl-N-[6-(methylamino)hexyl]-1,2,3,4-tetrahydroisoquinoline-3-carboxamide (±)-N-Methyl-N-[6-(methylamino)hexyl]-2-({4-[(phenylmethyl)oxy]phenyl}acetyl)-1,2,3,4-tetrahydroisoquinoline-3-carboxamide (±)-N,11-Dimethyl-N-[6-(methylamino)hexyl]-12-(1-methylethyl)-10-oxo-2,5,8-trioxa-11-azatridecan-13-amide (±)-N-(6-Aminohexyl)-1-pentanoylpiperidine-2-carboxamide (±)-N-(2-Aminoethyl)-1-pentanoylpiperidine-2-carboxamide (±)-N-(2-Aminoethyl)-1-tridecanoylpiperidine-2-carboxamide (R)-1-Undecanoyl-piperidine-2-carboxylic acid (5-amino-pentyl)-amide (S)-1-Undecanoyl-piperidine-2-carboxylic acid (5-amino-pentyl)-amide (R)-1-Undecanoyl-piperidine-2-carboxylic acid (3-amino-propyl)-amide (S)-1-Undecanoyl-piperidine-2-carboxylic acid (3-amino-propyl)-amide (R)-1-Nonanoyl-piperidine-2-carboxylic acid (5-amino-pentyl)-amide (S)-1-Nonanoyl-piperidine-2-carboxylic acid (5-amino-pentyl)-amide (R)-1-Nonanoyl-piperidine-2-carboxylic acid (3-amino-propyl)-amide (S)-1-Nonanoyl-piperidine-2-carboxylic acid (3-amino-propyl)-amide (R)-1-Octanoyl-piperidine-2-carboxylic acid (5-amino-pentyl)-amide (S)-1-Octanoyl-piperidine-2-carboxylic acid (5-amino-pentyl)-amide (R)-1-Octanoyl-piperidine-2-carboxylic acid (3-amino-propyl)-amide (S)-1-Octanoyl-piperidine-2-carboxylic acid (3-amino-propyl)-amide (R)-1-Hexanoyl-piperidine-2-carboxylic acid (5-amino-pentyl)-amide (S)-1-Hexanoyl-piperidine-2-carboxylic acid (5-amino-pentyl)-amide (R)-1-Hexanoyl-piperidine-2-carboxylic acid (3-amino-propyl)-amide (S)-1-Hexanoyl-piperidine-2-carboxylic acid (3-amino-propyl)-amide (R)-1-(2-Biphenyl-4-yl-ethanoyl)-piperidine-2-carboxylic acid (5-amino-pentyl)-amide (R)-1-(1-Biphenyl-4-yl-methanoyl)-piperidine-2-carboxylic acid (5-amino-pentyl)-amide (R)-1-Undecanoyl-piperidine-2-carboxylic acid (4-diethylaminobutyl)-amide (R)-1-Undecanoyl-piperidine-2-carboxylic acid (3-dimethylamino-propyl)-amide (R)-1-(Decane-1-sulfonyl)-piperidine-2-carboxylic acid (5-amino-pentyl)-amide (R)-1-(Decane-1-sulfonyl)-piperidine-2-carboxylic acid (3-amino-propyl)-amide (R)-1-Undecanoyl-pyrrolidine-2-carboxylic acid (5-amino-pentyl)-amide (S)-1-Undecanoyl-pyrrolidine-2-carboxylic acid (5-amino-pentyl)-amide (R)-1-Undecanoyl-pyrrolidine-2-carboxylic acid (3-amino-propyl)-amide (S)-1-Undecanoyl-pyrrolidine-2-carboxylic acid (3-amino-propyl)-amide (R)-1-Nonanoyl-pyrrolidine-2-carboxylic acid (5-amino-pentyl)-amide (S)-1-Nonanoyl-pyrrolidine-2-carboxylic acid (5-amino-pentyl)-amide (R)-1-Nonanoyl-pyrrolidine-2-carboxylic acid (3-amino-propyl)-amide (S)-1-Nonanoyl-pyrrolidine-2-carboxylic acid (3-amino-propyl)-amide (R)-1-Octanoyl-pyrrolidine-2-carboxylic acid (5-amino-pentyl)-amide (S)-1-Octanoyl-pyrrolidine-2-carboxylic acid (5-amino-pentyl)-amide (R)-1-Octanoyl-pyrrolidine-2-carboxylic acid (3-amino-propyl)-amide (S)-1-Octanoyl-pyrrolidine-2-carboxylic acid (3-amino-propyl)-amide (R)-1-Hexanoyl-pyrrolidine-2-carboxylic acid (5-amino-pentyl)-amide (S)-1-Hexanoyl-pyrrolidine-2-carboxylic acid (5-amino-pentyl)-amide (R)-1-Hexanoyl-pyrrolidine-2-carboxylic acid (3-amino-propyl)-amide (S)-1-Hexanoyl-pyrrolidine-2-carboxylic acid (3-amino-propyl)-amide (R)-1-(2-Biphenyl-4-yl-ethanoyl)-pyrrolidine-2-carboxylic acid (5-amino-pentyl)-amide (R)-1-(1-Biphenyl-4-yl-methanoyl)-pyrrolidine-2-carboxylic acid (5-amino-pentyl)-amide (R)-1-Undecanoyl-pyrrolidine-2-carboxylic acid (4-diethylaminobutyl)-amide (R)-1-Undecanoyl-pyrrolidine-2-carboxylic acid (3-dimethylamino-propyl)-amide (R)-1-(Decane-1-sulfonyl)-pyrrolidine-2-carboxylic acid (5-amino-pentyl)-amide (R)-1-(Decane-1-sulfonyl)-pyrrolidine-2-carboxylic acid (3-amino-propyl)-amide (R)-N-(5-Aminopentyl)-methyl-C-(methyl-undecanoyl-amino)-butyramide (R)-N-(3-Aminopropyl)-methyl-C-(methyl-undecanoyl-amino)-butyramide (R)-N-(5-Aminopentyl)-methyl-C-(methyl-nonanoyl-amino)-butyramide (R)-N-(5-Aminopentyl)-methyl-C-(methyl-octanoyl-amino)butyramide Thereby, the most preferred compounds are those which are selected from the group consisting of:

(S)-1-Tridecanoyl-piperidine-2-carboxylic acid (6-amino-hexyl)-amide (R)-1-Tridecanoyl-piperidine-2-carboxylic acid (6-amino-hexyl)-amide (S)-N-(6-Aminohexyl)-1-tridecanoylpyrrolidine-2-carboxamide (R)-N-(6-Aminohexyl)-1-tridecanoylpyrrolidine-2-carboxamide (R)-N-(6-Aminopentyl)-1-tridecanoylpyrrolidine-2-carboxamide (S)-N-(6-Aminopentyl)-1-tridecanoylpyrrolidine-2-carboxamide (S)-N-(1-{[(6-Aminohexyl)amino]carbonyl}-2-methylpropyl)-N-methyltridecanamide A further aspect of the present invention is related to the use of the amine derivatives of formula I for the preparation of pharmaceutical compositions and their use for treating diseases including Alzheimer's disease, Parkinson's disease, diseases associated with polyglutamine tracts including Huntington's disease, spinocerebellar ataxias and dentatorubral-pallidoluysian atrophy; amyotrophic lateral sclerosis, Crohn's disease, retinitis pigmentosa and multiple sclerosis, epilepsy), ischemia (stroke, myocardial infarction and reperfusion injury), infertility (like premature menopause, ovarian failure or follicular atresia), cardiovascular disorders (arteriosclerosis, heart failure and heart transplantation), renal hypoxia, hepatitis and AIDS.

According to a preferred embodiment, the above cited diseases or disease states are treated by the modulation of the Bax function, or the modulation (e.g. the inhibition) of the activation or expression of Bax, respectively, via the use of compounds of formula I, whereby the term Bax function notably comprises the actually active form of Bax as an oligomer (see B. Antonsson et al. in 2000 BiochemJ., Vol. 345, 271–278). Through the modulation of the Bax function, a convenient method of treatment of disorders mediated by Bax is expected, including in particular neuronal disorders and/or disorders of the immune system. Said modulation could notably involve the inhibition of the activity (activation) and/or of the expression of Bax. Also, said modulation of the Bax function or activity could actually comprise the inhibition or disruption for instance of the Bid interaction with Bax, which has been shown to play a role within the context of the Bax activation leading to cytochrome c release (see J. C. Martinou et al. in 1999 The Journal of Cell Biology, 144(5), 891–901). As a result of the inhibition of the Bax activation by Bid upon using the compounds according to formula I, the cytochrome c release could be inhibited or essentially blocked, thus providing a convenient means to modulate the above described apoptosis pathways. As a result, by said modulation of the apoptosis pathways a whole variety of disorders associated with abnormal apoptosis is expected to be treated.

It is reported herein that the compounds of formula I are suitable to be used as a medicament, i.e. they are suitable for use in treating disorders of the autoimmune system and neuronal system of mammals, notably of human beings. More specifically, the compounds according to formula I, alone or in the form of a pharmaceutical composition, are useful for the modulation, in particular for the inhibition, of the Bax function and/or the Bax activation. More specifically, the compounds according to formula I, alone or in the form of a pharmaceutical composition, are useful for the treatment or prevention of disorders associated with abnormal expression or activation of Bax. The compounds according to formula I could be employed alone or in combination with further pharmaceutical agents. The compounds of formula I are suitable to be used as a medicament alone or in the form of a pharmaceutical composition together with suitable carriers, diluents or excipients. The compounds of formula I are suitable to be used for the preparation of orally administrated pharmaceutical compositions.

Thus, according to the present invention, compounds pursuant to formula I are particularly useful for the treatment or prevention of immuno- and/or neuronal-related diseases or pathological states in which preferably the modulation, in particular the inhibition, of the Bax function and/or the Bax activation plays a crucial role, such as neurodegenerative diseases (e.g. Alzheimer's disease, Parkinson's disease, diseases associated with polyglutamine tracts including Huntington's disease, spinocerebellar ataxias and dentatorubral-pallidoluysian atrophy; amyotrophic lateral sclerosis, Crohn's disease, retinitis pigmentosa and multiple sclerosis, epilepsy), ischemia (stroke, myocardial infarction and reperfusion injury), infertility (like premature menopause, ovarian failure or follicular atresia), cardiovascular disorders (arteriosclerosis, heart failure and heart transplantation), renal hypoxia, hepatitis and AIDS.

As a matter of fact, prior to the herein reported surprisingly found pharmaceutically active amine derivatives according to formula I, nothing was known in respect of the use of small molecule chemical compounds as active inhibitors of the pro-apoptosis agent Bax. Nothing was known in respect of the possibility to disrupt or to substantially block—with small molecules—the activation of Bax, for instance via Bid (being another Bcl-2 family member which is involved in the pathways leading to the release of cytochrome c).

A further aspect of the present invention consists in the use of amine derivatives of formula I for the preparation of a pharmaceutical composition for the treatment or prevention of disorders associated with an abnormal Bax function or abnormal (e.g. elevated) Bax activation, an abnormal expression or activity of Bax as well as said pharmaceutical compositions themselves. Hence, such amine derivatives of formula I being useful for the preparation of a pharmaceutical composition for the treatment or prevention of disorders which are preferably associated with the modulation of the Bax function or activation, in particular with the abnormal expression or activity of Bax have the above set out general formula I. Also, the amine derivatives of formula I of the present invention are useful for the treatment of neurodegenerative diseases (e.g. Alzheimer's disease, Parkinson's disease, diseases associated with polyglutamine tracts including Huntington's disease, spinocerebellar ataxias and dentatorubral-pallidoluysian atrophy; amyotrophic lateral sclerosis, Crohn's disease, retinitis pigmentosa and multiple sclerosis, epilepsy), ischemia (stroke, myocardial infarction and reperfusion injury), infertility (like premature menopause, ovarian failure or follicular atresia), cardiovascular disorders (arteriosclerosis, heart failure and heart transplantation), renal hypoxia, hepatitis and AIDS.

A further aspect of the present invention consists in the use of amine derivatives according to formula I for the preparation of a pharmaceutical composition for the treatment or prevention of disorders associated with abnormal Bax function or Bax activation, an abnormal expression or activity of Bax as well as said pharmaceutical compositions themselves. Such a composition could be prepared by using the compounds according to formula I. Hence, such compounds of formula I useful for the preparation of a pharmaceutical composition for the treatment or prevention of disorders associated with the modulation of the Bax function or activation, in particular with the abnormal expression or activity of Bax have the general formula:

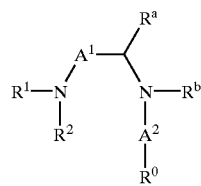

and its geometrical isomers, in an optically active form as enantiomers, diastereomers, as well as in the form of racemate, as well as pharmaceutically acceptable salts thereof, wherein $A^1$ and $A^2$ are selected independently from each other from the group consisting of —C(O)— and —SO$_2$—.

$R^a$ is $C_1$–$C_{10}$ alkyl, $R^b$ is $CH_3$, or $R^a$ and $R^b$ taken together with the atoms to which they are attached form a five-membered saturated ring optionally containing a sulfur atom or a six-membered saturated ring optionally fused with an aryl or heteroaryl group.

$R^1$ is either H or $C_1$–$C_6$ alkyl.

$R^2$ is —($R^d$—$X_1$)$_m$—$R^e$ wherein m is an integer from 0 to 8.

Therein, $R^d$ is selected of aryl, heteroaryl, $C_1$–$C_{18}$ alkyl, 3–8-membered cycloalkyl, $C_2$–$C_{18}$ alkenyl or 3–8-membered cycloalkenyl, $C_2$–$C_{18}$ alkynyl.

$X_1$ is a bond, O, NH, NR$^g$, NR$^g$N$^{g'}$, S, Si(R$^g$R$^{g'}$), SO, SO$_2$, wherein $R^g$ and $R^{g'}$ are independently selected from the group consisting of substituted or unsubstituted $C_1$–$C_6$ alkyl, $C_2$–$C_8$ alkenyl, $C_2$–$C_8$ alkynyl, aryl or heteroaryl.

$R^e$ is selected of aryl-$C_1$–$C_{18}$ alkyl, aryl-$C_2$–$C_{18}$ alkenyl, aryl-$C_2$–$C_{18}$ alkynyl, heteroaryl-$C_1$–$C_{18}$ alkyl, heteroaryl-$C_2$–$C_{18}$ alkenyl, heteroaryl-$C_2$–$C_{18}$ alkynyl, $C_1$–$C_{18}$ alkyl, $C_2$–$C_{18}$ alkenyl, $C_2$–$C_{18}$ alkynyl, said $C_1$–$C_{18}$ alkyl, $C_2$–$C_{18}$ alkenyl and $C_2$–$C_{18}$ alkynyl have a terminal substituent of the formula —OR, —NRR' or —N$^+$RR'R" wherein R, R', R" are selected independently from each other of H, $C_1$–$C_6$-alkyl, preferably methyl or ethyl. Alternatively, at least 2 of R, R' and R" form a 3–12 membered cyclic or bicyclic ring. A terminal ammonium moiety of the formula —N$^+$RR'R", with all groups R, R' and R" being organic residues represents one preferred embodiment. A further preferred terminal amino group is —NH$_2$ and OH.

Also $R^1$ and $R^2$ together with the N atom to which they are attached could form an unsubstituted or substituted 4–12 membered unsaturated or saturated ring containing one further heteroatom selected from O, N. Said ring may optionally be substituted by $R^e$, or directly by a terminal substituent of the formula OR, —NRR' or —N$^+$RR'R" wherein R, R', R" are H, $C_1$–$C_6$-alkyl whereby $R^e$ is as defined above.

$R^0$ of the above formula (1) is $R^f$—$X_2$—$R^{f'}$ wherein $R^f$ and $R^{f'}$ are independently from each other selected from the group consisting of aryl, heteroaryl, 3–8-membered cycloalkenyl, 3–8-membered cycloalkyl, $C_2$–$C_{18}$ alkyl, $C_2$–$C_{18}$ alkenyl, $C_2$–$C_{18}$ alkynyl, aryl-$C_1$–$C_{18}$ alkyl, aryl-$C_2$–$C_{18}$ alkenyl, aryl-$C_2$–$C_{18}$ alkynyl, heteroaryl-$C_1$–$C_{18}$ alkyl, heteroaryl-$C_2$–$C_{18}$ alkenyl, heteroaryl-$C_2$–$C_{18}$ alkynyl, $X_2$ is a bond or O, S, Si(R$^g$R$^{g'}$), SO, SO$_2$, wherein $R^g$ and $R^{g'}$ are selected as above defined.

Still a further object of the present invention is a process for preparing the novel compounds according to formula I which have been set out above.

Compounds of formula I of this invention can be prepared from readily available starting materials using the following general methods and procedures.

It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvent used, but such conditions can be determined by a person skilled in the art by routine optimisation procedures.

Compounds according to the general formula I could be obtained by two major processes (A) and (B).

According to the process (A), compounds according to the general formula I are prepared from the corresponding protected amino derivatives as described in the literature and as set out in the ensuing examples and shown in Scheme I, below.

Scheme I, wherein $A^1$=$A^2$ are carbonyl (C=O), illustrates the reaction of a protected amino acid derivative of formula IIA with an amino derivative of formula III to form protected amino derivatives of formula IVA. The formula IVA compounds, after a deprotection step, then react with carboxylic acid derivatives of formula VA to form compounds of formula I.

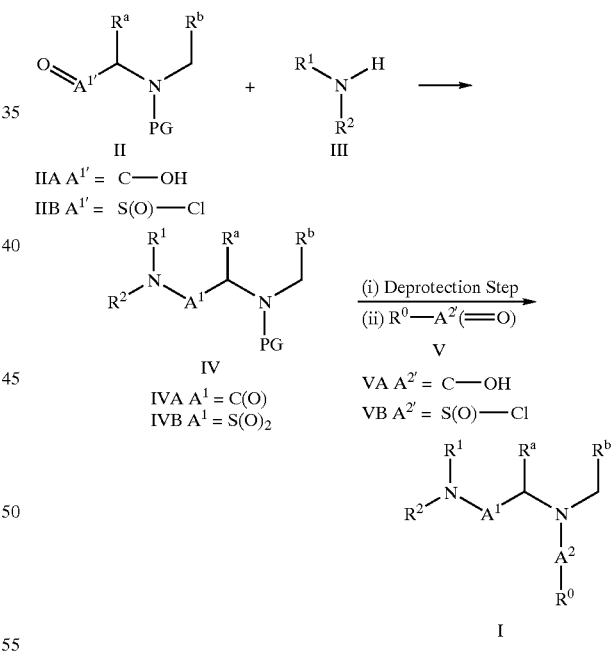

According to scheme I, the compounds of formula I wherein $A^1$=$A^2$ are S(O)$_2$, are obtained by the reaction of a protected amino derivative of formula IIB with an amino derivative of formula III to form protected amino derivatives of formula IVB. Then, said formula IVB compounds are first subjected to a deprotection step (being performed according to methods that are well known to a person skilled in the art), and are then reacted with sulfonyl chloride derivatives of formula VB to finally provide the compounds of formula I.

Still according to scheme I, the compounds of formula I wherein, $A^1$=(C=O) and $A^2$=S(O)$_2$ are obtained by the reaction of a protected amino acid derivative of formula IIA with an amino derivative of formula III to form protected amino derivatives of formula IVA. Then, said formula IVA compounds are first subjected to a deprotection step (being performed according to methods that are well known to a person skilled in the art), and are then reacted with sulfonyl chloride derivatives of formula VB to finally provide the compounds of formula I.

Scheme I also illustrates the reaction pathways to provide the compounds of formula I wherein $A^1=S(O)_2$ and $A^2=C(O)$ or $A^1=A^2=C(O)$. Thus, for obtaining compounds wherein $A^1=S(O)_2$ and $A^2=C(O)$ a protected amino derivative of formula IIB is reacted with an amino derivative of formula III to form protected amino derivatives of formula IVB. The formula IVB compounds, after a deprotection step, then react with acid derivatives of formula VA to form compounds of formula I.

Compounds of formula I can be prepared as individual enantiomers or in an enantiomeric enriched form from the appropriate enantiomer of formula II or as a racemic mixture from the appropriate racemic compound of formula II. Individual enantiomers of the invention can be prepared from racemates by resolution using methods known in the art for the separation of racemic mixtures into their constituent enantiomers, for example using HPLC on a chiral column, or using separation of salts of diastereomers.

Compounds of formula II, III and V are either commercially available compounds or may be prepared by standard synthetic techniques as hereinafter described in the Examples.

According to an alternative method (process (B)), the compounds according to the general formula I are prepared from the corresponding protected amino derivatives by solid-phase protocols such as described in the example 2, also for the specific compounds set out in Tables 1 and 2 and also shown in schemes II and III, below.

Scheme II

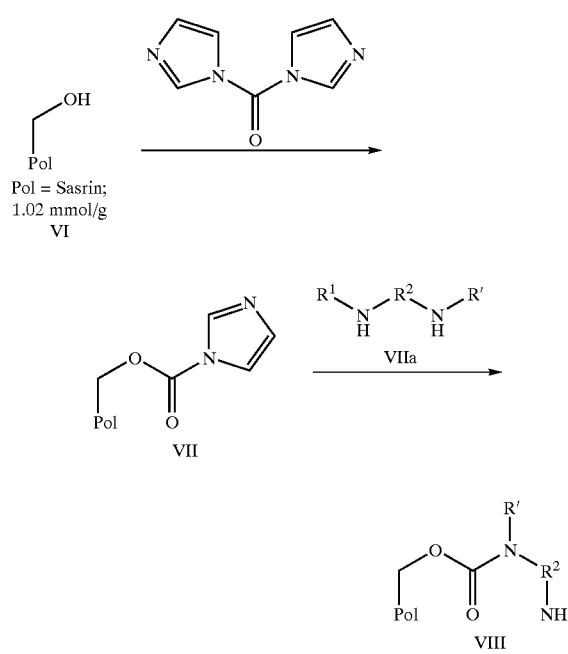

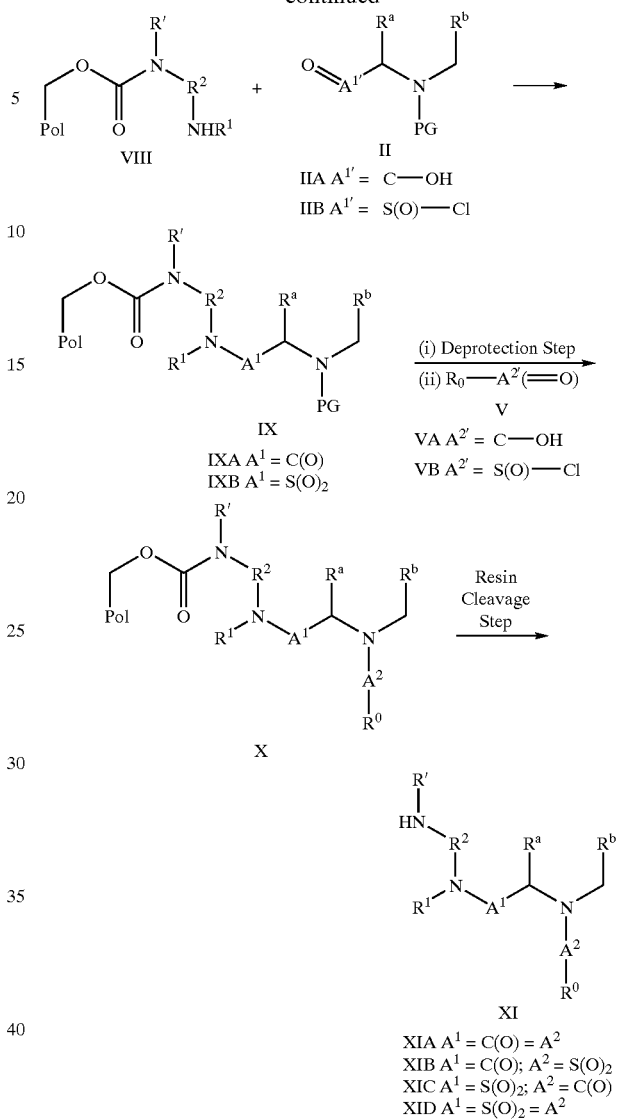

In the solid-phase reaction pathways depicted in Scheme II, a primary or secondary diamine of formula VIIa is reacted with the activated resin VII. Said compound VII is derived from reaction of the acid-labile hydroxymethyl resins VI—such as Sasrin or ArgoGel MB-OH (Argonaut), having been conditioned by standard processes well known to the practitioner skilled in the art, e.g. by using phosgene equivalents, such as CDI, triphosgene, or others. The free amino group of the carbamate VIII can then be coupled to commercial and non-commercial N-protected amino carboxylic acid derivatives IIA using standard peptide coupling protocols well known to the person skilled in the art. After N-deprotection, the free amino group can be reacted either with acid derivatives of formula VA, or with sulfonyl chlorides of formula VB, to yield, after acid-catalyzed cleavage from the solid support, compounds of formula XIA, or of formula XIB, respectively. Through the synthesis depicted in Scheme II, compounds of formula I could be obtained, wherein the terminal NR,R' groups within the substituent $R^2$ are $NH_2$ or NH—$C_1$–$C_6$-alkyl.

Alternatively, the free amino group of the carbamate VIII can be reacted with N-protected amino derivatives of formula IIB using standard protocols for sulfonamide formation well known to the person skilled in the art. After N-deprotection, the free amino group can be reacted either with acid derivatives of formula VA, or with sulfonyl chlorides of formula VB, to yield, after acid-catalyzed cleavage from the solid support, compounds of formula XIC, or of formula XID, respectively.

Other derivatives of formula I are prepared using known modifications to the scheme II reaction sequence. Compounds of formula I wherein A is a sulfonyl functionality are prepared by replacing formula II and V with sulfonyl chloride functional groups to yield sulfonamide derivatives.

Based on a further solid-supported reaction sequence, compounds of formula I can be obtained by performing the reactions illustrated in Scheme III.

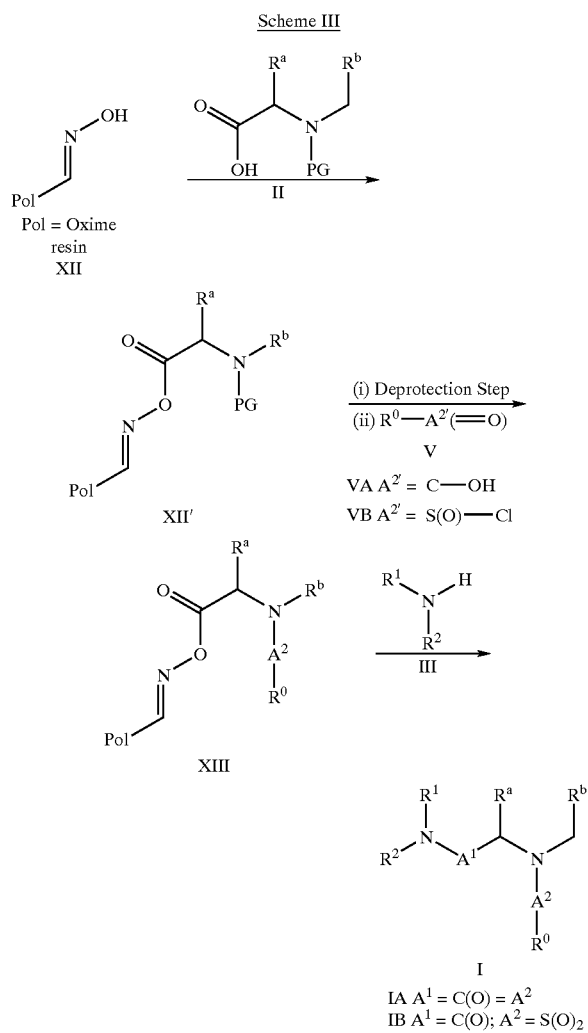

According to the general procedures well known to the practitioner in the field of solid-phase synthesis, N-protected commercial or non-commercial amino acids II are coupled to oxime resin XII (e.g. Oxime Resin from Novabiochem) yielding XII'. After N-deprotection, the free amino group can be reacted either with acid derivatives of formula VA, or with sulfonyl chlorides of formula VB, to yield, after cleavage from the solid support with primary or secondary amines III, compounds of formula IA, or of formula IB, respectively.

According to a further general process, compounds of formula I can be converted to alternative compounds of formula I, employing suitable interconversion techniques which are known to a person skilled in the art.

Compounds of this invention can be isolated in association with solvent molecules by crystallization from evaporation of an appropriate solvent. The pharmaceutically acceptable acid addition salts of the compounds of formula I, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula I with a suitable base. Both types of salt may be formed or interconverted using ion-exchange resin techniques.

A final aspect of the present invention is related to the formulations containing the active compounds according to formula I. When employed as pharmaceuticals, the compounds of formula I of the present invention are typically administered in the form of a pharmaceutical composition. Hence, pharmaceutical compositions comprising a compound of formula I and a pharmaceutically acceptable carrier, diluent or excipient therefore are also within the scope of the present invention. A person skilled in the art is aware of a whole variety of such carrier, diluent or excipient compounds suitable to formulate a pharmaceutical composition. Also, the present invention provides compounds for use as a medicament. In particular, the invention provides compounds according to formula I for use as Bax modulators, i.e. for the treatment of disorders or disease states in mammals, notably in human beings. Said disorders are associated with inappropriate cell death, including neurodegenerative disorders, diseases associated with polyglutamine tracts, epilepsy, ischemia, infertility, cardiovascular disorders, renal hypoxia, hepatitis and AIDS, either alone or in combination with other medicaments.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral administration (including subcutaneous use) Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the amino derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the amino derivative is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the compounds of formula I in such compositions is/are typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences*, 17$^{th}$ Edition, 1985, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples which are not to be construed as limiting the scope of the invention.

EXAMPLES

The following abbreviations are hereinafter used in the accompanying examples: min (minute), hr (hour), g (gram), mmol (millimole), m.p. (melting point), eq (equivalents), mL (milliliter), µL (microliters), mL (milliliters), DCM (dichloromethane), TFA (trifluoro-acetic acid), rt (room temperature), DMSO (dimethylsulfoxide), DMSO-d$_6$ (deuterated dimethylsulfoxide), THF (tetrahydrofuran), Na$_2$SO$_4$ (sodium sulfate), MgSO$_4$ (magnesium sulfate), CDCl$_3$ (deuterated chloroform), DIEA, (diisopropylethyl amine), TEA (triethyl amine), EtOAc (ethyl acetate), cHex (cyclohexane), Et$_2$O (diethyl ether), ACN (acetonitrile), NaHCO$_3$ (sodium bicarbonate), HOBt (1-hydroxybenzotriazole), EDCI (1-(3-di-methyl-amino-propyl)-3-ethylcarbodiimide), dimethylformamide (DMF), K$_2$CO$_3$ (potassium carbonate), HATU (N-{(dimethylamino) (1H-1,2,3-triazolo[4,5-b]pyridin-1-yl)-methylene}-N-methylmethanaminium hexafluorophosphate N-oxide), CDI (carbonyl-diimidazole).

Example 1

(S)-1-Tridecanoyl-piperidine-2-carboxylic acid (6-amino-hexyl)-amide (See Scheme 1)

A solution of (S)-(6-{[1-(1-tridecanoyl-piperidin-2-yl)-methanoyl]-amino}-hexyl)-carbamic acid tert-butyl ester (3.9 g, 7.45 mmol) in DCM (40 mL) was treated with TFA (8 mL) at −20° C. for two days until disappearance of the starting material. The reaction mixture was allowed to warm up to rt and was washed with an aqueous saturated solution of K$_2$CO$_3$. Extraction, drying over MgSO$_4$ and evaporation in vacuo gave a yellow oil. Purification via flash chromatography (SiO$_2$, 5×13 cm$^2$ column) using a mixture (90:10:2) of DCM:MeOH(5% aqueous solution of NH3) gave the title compound (1.35 g) as a pale yellow oil. The residue was taken in anhydrous DCM (25 mL) and treated with TFA (246 µL, 365 mg) at —10° C. Evaporation of the solvents gave the title compound (1.67 g, 3.11 mmol) as a yellow oil in a 42% yield.

Analysis for C$_{25}$H$_{49}$N$_3$O$_2$. 2TFA.0.037CH$_2$Cl$_2$: Calculated: C, 59.66; H, 9.44; N, 7.83. Found: C, 60.04; H, 9.33; N, 7.77%.

(S)-(6-{[1-(1-Tridecanoyl-piperidin-2-yl)-methanoyl]-amino}-hexyl)-carbamic acid tert-butyl ester was obtained by treating a solution of {6-[(1-piperidin-2-yl-methanoyl)-amino]hexyl}-carbamic acid tert-butyl ester in DCM (100 mL) with tridecanoic acid (2.36 g, 1.1 equiv.) in the presence of HATU (5.0 g, 1.3 equiv.) and DIEA (4.2 mL, 2.4 equiv.). After 2 hours of stirring at rt the reaction was judged to be complete by tlc monitoring. DCM was added (50 mL) and the reaction mixture was washed 3 times with citric acid (0.5 M). 3 times with an aqueous saturated solution of NaHCO$_3$ and with brine. Drying over Na$_2$SO$_4$, evaporation in vacuo gave a residue which was purified via flash chromatography (SiO$_2$) using EtOAc:chexanes (6:4) as eluant. (S)-(6-{[1-(1-Tridecanoyl-piperidin-2-yl)-methanoyl]-amino}-hexyl)-carbamic acid tert-butyl ester (4.6 g) was obtained as a yellow oil in a 87% yield.

$^1$H-RMN (CDCl$_3$/CD$_3$OD (14/1), 300 MHz) δ 5.05 (d, 0.8H), 4.50 (d, 0.2H), 4.37 (d, 0.2H), 3.68 (d, 0.8H), 3.27–2.86 (m, 5H), 2.55–2.05 (m, 3H), 1.70–1.10 (m, 42H), 0.79 (t, 3H).

{6-[(1-Piperidin-2-yl-methanoyl)-amino]hexyl}-carbamic acid tert-butyl ester was obtained by treating (L)-2-(6-tert-butoxycarbonylamino-hexylcarbamoyl)-piperidine-1-carboxylic acid 9H-fluoren-9-ylmethyl ester (7.0 g, 12.8 mmol) with 500 mL of a solution piperidine in DMF (20%) for 50 min. After evaporation of the solvent in vacuo, the resulting pale yellow solid was flash chromatographed using DCM:MeOH (90:10) as eluant. After evaporation of the solvent in vacuo {6-[(1-piperidin-2-yl-methanoyl)-amino]hexyl}-carbamic acid tert-butyl ester was obtained a white solid in a 80% yield.

MS (APCI): (M+1)=328.

To a solution of (L)-piperidine-1,2-dicarboxylic acid 1-(9H-fluoren-9-ylmethyl)ester (5.0 g, 14.2 mmol) in 400 mL of DCM were added (6-amino-hexyl)-carbamic acid tert-butyl ester (3.96 g, 1.1 equiv.), HATU (7.0 g, 1.3 equiv.) and DIEA (10.8 mL, 4.4 equiv.) under inert atmosphere.

After 2 hours of stirring at rt the reaction mixture was washed twice with an aqueous solution of HCl (1M), twice with an aqueous saturated solution of NaHCO$_3$ and with brine. After drying over Na$_2$SO$_4$, evaporation in vacuo, an oily residue was obtained and filtered through a silica plug using a mixture of EtOAc:chexanes (8:2) as eluant. After evaporation in vacuo (L)-2-(6-tert-butoxycarbonylamino-hexylcarbamoyl)-piperidine-1-carboxylic acid 9H-fluoren-9-ylmethyl ester was obtained as a white foam in a 90% yield. MS (APCI): (M+Na)=572.

Example 2

(R)-1-Tridecanoyl-piperidine-2-carboxylic acid (6-amino-hexyl)-amide (See Scheme 2)

To a 500 mg-batch of ArgoGel MB-OH (from Argonaut; loading 0.4 mmol/g, 0.2 mmol) was added a solution of 163 mg (1 mmol, 5 eq.) carbonyldiimidazole and 171 µl (1 mmol, 5 eq.) DIEA in 5 ml of dry THF, and the resulting mixture was allowed to react for 7 h at room temperature under gentle shaking. After this time, the resin was washed with THF (2×), DCM (2×), DMF (1×) and then directly used for the following step. The resin was allowed to react for 15 h at room temperature with a solution of 230 µl (2 mmol, 10 eq.) 1,6-hexanediamine (see compound VIIa in Scheme 2) and 342 µl (2 mmol, 10 eq.) DIEA in 5 ml DMF. After this time, the resin batches were washed with DMF (3×), DCM (1×), THF (2×), DCM (3×), and Et$_2$O (2×) and dried in vacuo. To the resulting resin batch was added a solution of 211 mg (0.6 mmol, 3 eq.) Fmoc-D-pipecolic acid (see compound IIa in Scheme 2), 228 mg (0.6 mmol, 3 eq.) HATU, and 206 µl (1.2 mmol, 6 eq.) DIEA in 3 ml anhydr. DMF. After a reaction time of 8 h at ambient temperature, the resin was washed with DMF (5×), DCM (5×), DMF (5×), DCM (3×), Et$_2$O (2×), and dried in vacuo. The resin was now treated with 4ml of a solution of 20% (v/v) piperidine in DMF for 20 min at room temperature, then washed with DMF (5×), DCM (5×), DMF (5×). To the resulting resin was added a solution of 129 mg (0.6 mmol, 3 eq.) tridecanoic acid (see compound V in Scheme 2), 228 mg (0.6 mmol, 3 eq.) HATU, and 206 µl (1.2 mmol, 6 eq.) DIEA in 3 ml anhydr. DMF. After a reaction time of 8h at room temperature, the reaction was worked up by washing with DMF (5×), DCM (5×), DMF (5×), DCM (3×), Et$_2$O (2×), and the resin batches were dried in vacuo at r.t. O/N. The resin was treated with a solution of 20% (v/v) TFA in DCM for 10 min at room temperature, to release the title compound from the resin in 60% overall yield.

$^1$H-RMN (CDCl$_3$, 300 MHz) δ 8.14 (bs, 3H), 6.74 (bs, 1H), 5.06 (bs, 0.85H), 4.53 (d, 0.15H), 4.44 (bs, 0.15H), 3.73 (d, 0.85H), 3.23 (m, 3H), 2.99 (bs, 2H), 2.34 (bs, 2H), 2.14 (d, 1H), 1.85–1.15 (m, 33H), 0.86 (t, 3H).

Examples 3 through 140

The compounds belonging to examples 3 through 140 were prepared by following the procedure outlined above for example 2 and by using the correspondingly adapted starting materials.

Thus, the diamine compounds of formula VIIa (see scheme 2) may be selected from the group comprising ethylenediamine, propanediamine, butanediamine, pentanediamine, heptanediamine, octanediamine, nonanediamine, decanediamine etc. Such diamine compounds are either commercially available or may be obtained by methods that are known to a person skilled in the art. Also, said diamine compounds may be transformed according to procedures known to a person skilled in the art, in order to obtain secondary diamine compounds or ammonium salts.

The amino carboxylic acid derivatives to form the protected species of formula IIa may be selected from the group comprising pipecolic acid (2-piperidinecarboxylic acid), pyrrolidine-2-carboxylic acid, 5-carboxylic acid 1,3-thiazolidine, 3-carboxylic acid-1,2,3,4-tetrahydroisoquinoline, N-methylvaline, etc. Accordingly, the amino sulfonly chlorides may be selected from the group comprising pyrrolidine-2-sulfonyl chloride, 5-sulfonyl chloride 1,3-thiazolidine, 3-sulfonyl chloride-1,2,3,4-tetrahydroisoquinoline, pipecolic sulfonyl chloride etc. In order to obtain the protected species of formula IIA or IIB said amino carboxylic acid derivatives or amino sulfonly chlorides are protected with suitable protecting groups including Fmoc, Boc, etc. using methods that known to a person skilled in the art.

The carboxylic acids and sulfonyl chlorides of the formulas VA and VB are commercially available and may be selected from the group comprising C$_1$–C$_{18}$ carboxylic acids, e.g. saturated or unsaturated carboxylic or fatty acids or the sulfonyl chloride derivatives, polyether carboxylic acids or their sulfonyl chloride derivatives. Specific carboxylic acids of formula VA are cyclohexylbutanoic acid, (2-(2)-methyloxyethyl)oxyethyloxy acetic acid, 1,1'-biphenyl-4-acetic acid, 4-phenyl-methyloxyphenyl acetic acid, decane sulfonylchloride, heptane sulfonylchloride, etc.

The overall yields for obtaining the compounds listed in Table 1 range from 50–90%.

TABLE 1

(Examples 2–140):

| Ex. No. | Structure | IUPAC Name | MW | % by HPLC (220 nm) | FI-MS(APCI) m/z mode | FI-MS(APCI) m/z neg. mode |
|---|---|---|---|---|---|---|
| 2 | 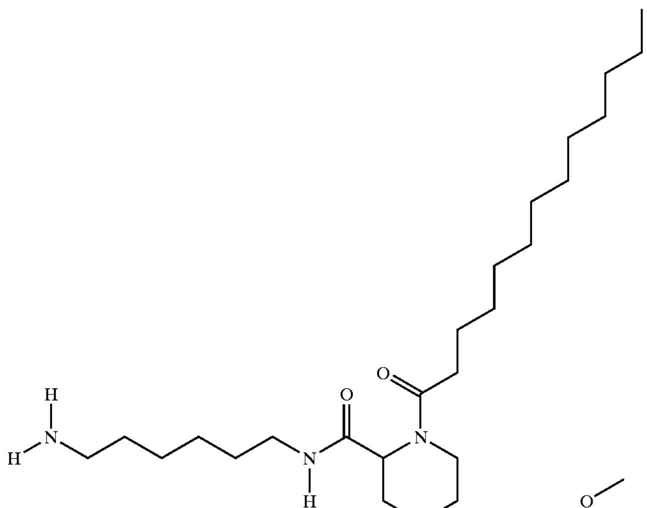 | (R)-N-(6-aminohexyl)-1-tridecanoylpiperidine-2-carboxamide | 423.69 | n/a | 424.2 | 422.4 |
| 3 | 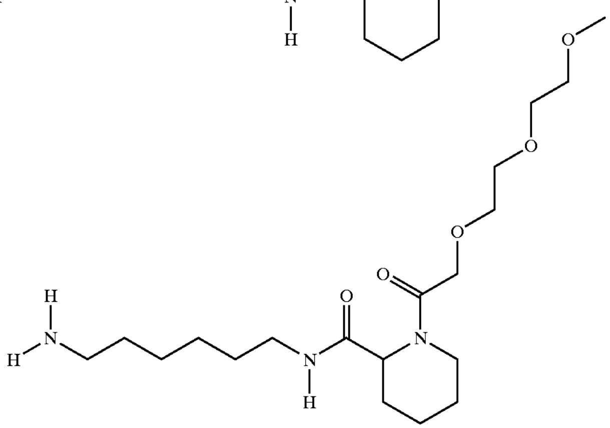 | N-(6-aminohexyl)-1-{[(2-(methyloxy)ethyl]oxy]ethyl)oxy]acetyl)piperidine-2-carboxamide | 387.52 | n/a | 388.2 | 386.0 |

TABLE 1-continued (Examples 2–140):

| Ex. No. | Structure | IUPAC Name | MW | | |
|---|---|---|---|---|---|
| 4 | (cyclohexylbutanoyl-piperidine-2-carboxamide structure) | N-(6-aminohexyl)-1-(4-cyclohexylbutanoyl)piperidine-2-carboxamide | 379.59 | n/a | 380.2 379.0 |
| 5 | (biphenylacetyl-piperidine-2-carboxamide structure) | N-(6-aminohexyl)-1-[(1,1′-biphenyl)-4-ylacetyl]piperidine-2-carboxamide | 421.59 | 82% | 422.2 420.0 |

TABLE 1-continued (Examples 2–140):

| Ex. No. | Structure | IUPAC Name | MW | | | |
|---|---|---|---|---|---|---|
| 6 | 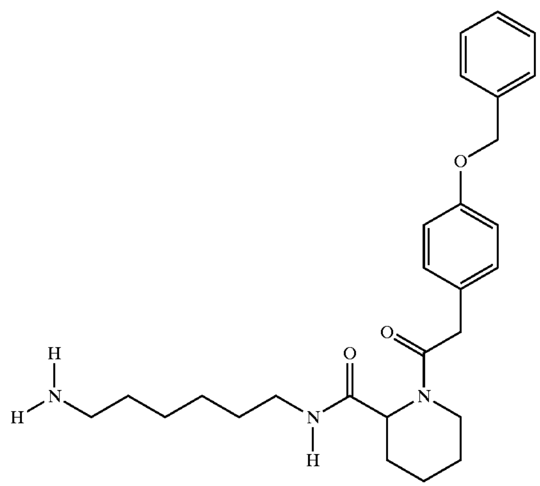 | N-(6-aminohexyl)-1-({4-[(phenylmethyl)oxy]phenyl}acetyl)piperidine-2-carboxamide | 451.61 | 76% | 452.2 | 450.2 |
| 7 | 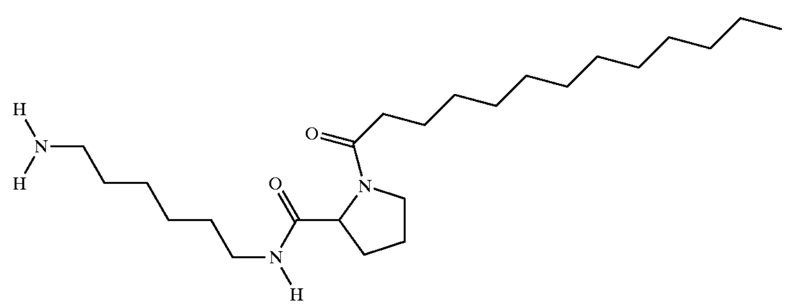 | (S)-N-(6-aminohexyl)-1-tridecanoylpyrrolidine-2-carboxamide | 409.66 | n/a | 410.2 | 408.2 |

TABLE 1-continued (Examples 2–140):

| Ex. No. | Structure | IUPAC Name | MW | Purity | FI-MS |
|---|---|---|---|---|---|
| 8 | 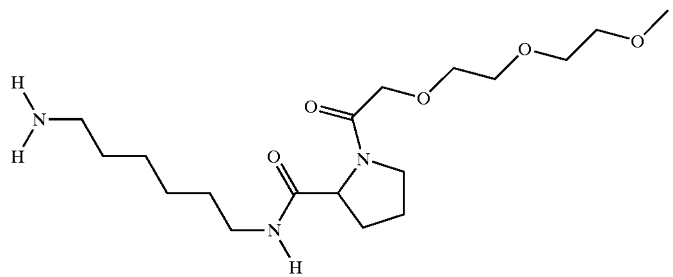 | N-(6-aminohexyl)-1-{[(2-{[2-(methyloxy)ethyl]oxy}ethyl)oxy]acetyl}pyrrolidine-2-carboxamide | 373.50 | n/a | 374.0 372.0 |
| 9 | 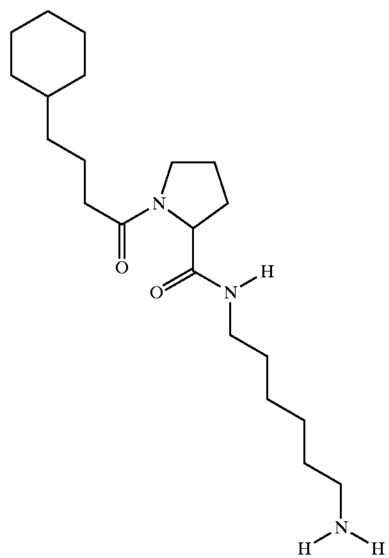 | N-(6-aminohexyl)-1-(4-cyclohexylbutanoyl)pyrrolidine-2-carboxamide | 365.56 | 366.2 | 364.3 |

TABLE 1-continued
(Examples 2-140):
| Ex. No. | Structure | IUPAC Name | MW | | |
|---|---|---|---|---|---|
| 10 | 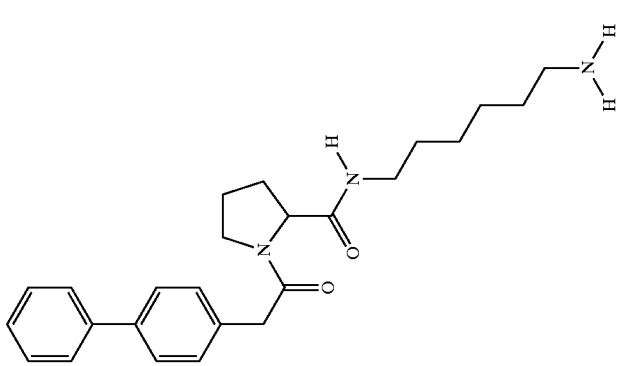 | N-(6-aminohexyl)-1-[[1,1'-biphenyl]-4-ylacetyl)pyrrolidine-2-carboxamide | 407.56 | 96% | 408.0 406.0 |

TABLE 1-continued (Examples 2-140):

| Ex. No. | Structure | IUPAC Name | MW | | |
|---|---|---|---|---|---|
| 11 | 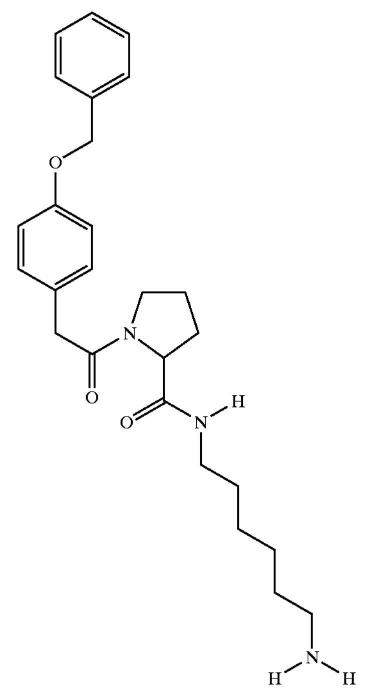 | N-(6-aminohexyl)-1-({4-[(phenylmethyl)oxy]phenyl}acetyl)pyrrolidine-2-carboxamide | 437.59 | 96% | 438.2 436.0 |
| 12 | 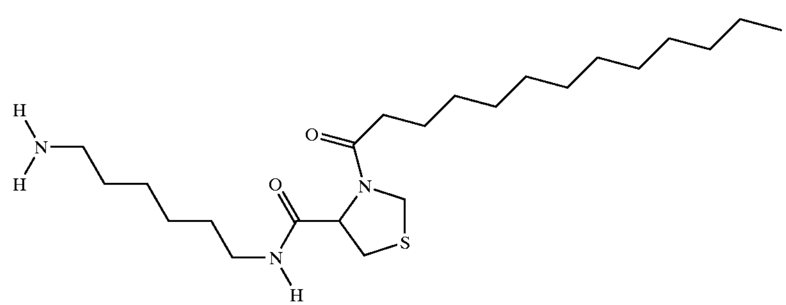 | N-(6-aminohexyl)-3-tridecanoyl-1,3-thiazolidine-4-carboxamide | 427.70 | n/a | 428.2 426.2 |

TABLE 1-continued (Examples 2-140):

| Ex. No. | Structure | IUPAC Name | MW | | |
|---|---|---|---|---|---|
| 13 | 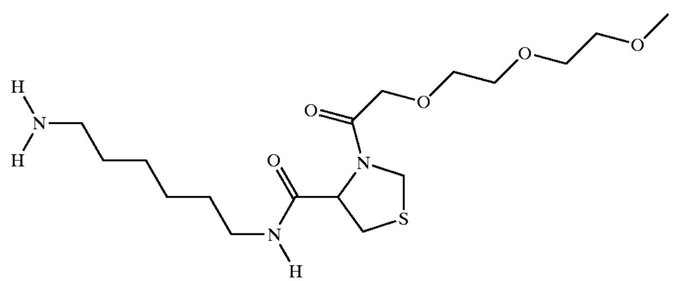 | N-(6-aminohexyl)-3-{[(2-{[(2-(methyloxy)ethyl]oxy)ethyl]oxy]acetyl}-1,3-thiazolidine-4-carboxamide | 391.53 | n/a | 392.2 390.2 |
| 14 | 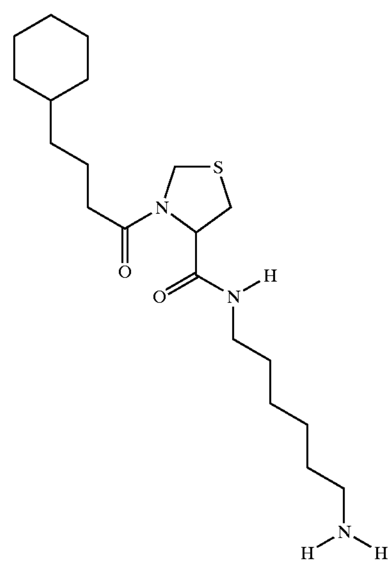 | N-(6-aminohexyl)-3-(4-cyclohexylbutanoyl)-1,3-thiazolidine-4-carboxamide | 383.60 | n/a | 384.2 382.0 |

TABLE 1-continued (Examples 2-140):

| Ex. No. | Structure | IUPAC Name | MW | | |
|---|---|---|---|---|---|
| 15 | 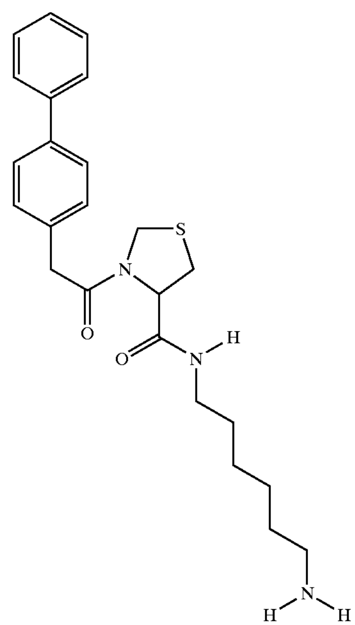 | N-(6-aminohexyl)-3-([1,1'-biphenyl]-4-ylacetyl)-1,3-thiazolidine-4-carboxamide | 425.60 | 90% | 426.2 424.0 |

TABLE 1-continued
(Examples 2-140):
| Ex. No. | Structure | IUPAC Name | MW | | |
|---|---|---|---|---|---|
| 16 | 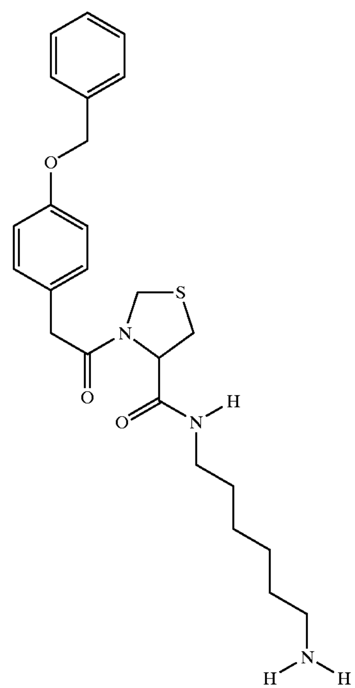 | N-(6-aminohexyl)-3-({4-[(phenylmethyl)oxy]phenyl}acetyl)-1,3-thiazolidine-4-carboxamide | 455.62 | 94% | 456.2 454.0 |

TABLE 1-continued (Examples 2–140):

| Ex. No. | Structure | IUPAC Name | MW | | |
|---|---|---|---|---|---|
| 17 | 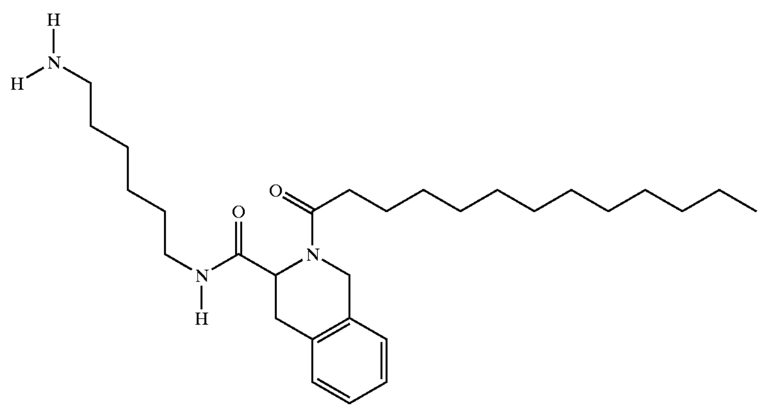 | N-(6-aminohexyl)-2-tridecanoyl-1,2,3,4-tetrahydroisoquinoline-3-carboxamide | 471.73 | 97% | 472.4 470.2 |
| 18 | 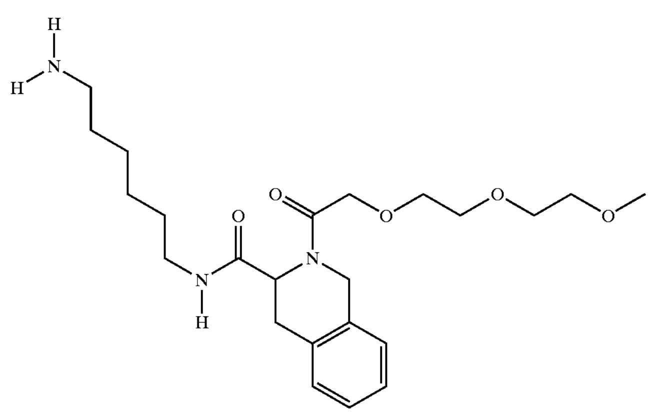 | N-(6-aminohexyl)-2-{[(2-{[2-(methyloxy)ethyl]oxy}ethyl)oxy]acetyl}-1,2,3,4-tetrahydroisoquinoline-3-carboxamide | 435.57 | 96% | 436.2 434.2 |

TABLE 1-continued (Examples 2–140):

| Ex. No. | Structure | IUPAC Name | MW | | | |
|---|---|---|---|---|---|---|
| 19 | 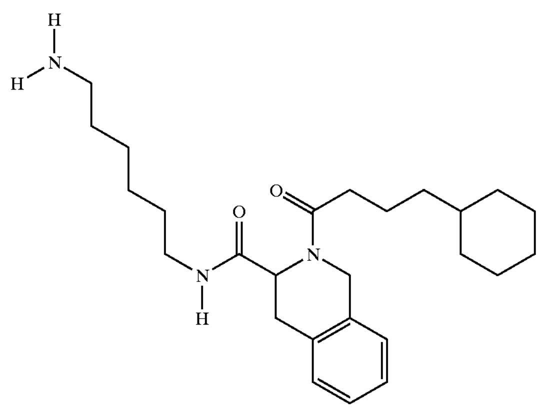 | N-(6-aminohexyl)-2-(4-cyclohexylbutanoyl)-1,2,3,4-tetrahydroisoquinoline-3-carbaxamide | 427.64 | 94% | 428.2 | 426.0 |
| 20 | 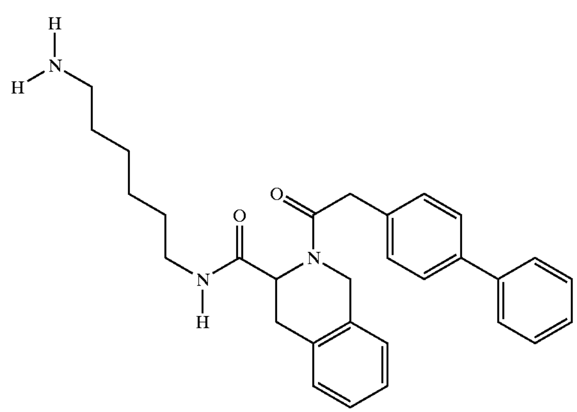 | N-(6-aminohexyl)-2-[[1,1'-biphenyl]-4-ylacetyl)-1,2,3,4-tetrahydroisoquinoline-3-carboxamide | 469.63 | 93% | 470.2 | 468.2 |

TABLE 1-continued (Examples 2–140):

| Ex. No. | IUPAC Name | MW | | | Structure |
|---|---|---|---|---|---|
| 21 | N-(6-aminohexyl)-2-({4-[(phenylmethyl)oxy]phenyl}acetyl)-1,2,3,4-tetrahydroisoquinoline-3-carboxamide | 499.66 | 95% | 500.2 498.2 | 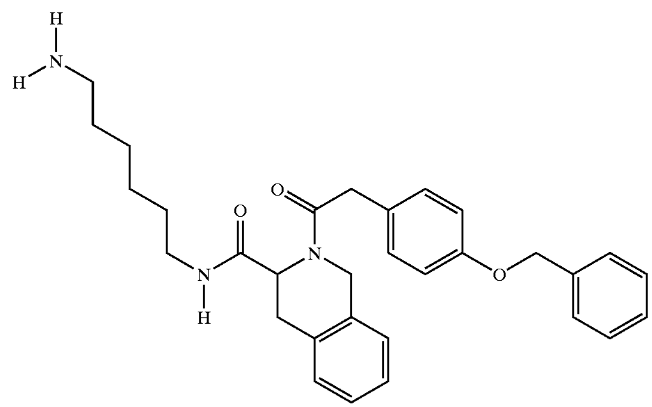 |
| 22 | (S)-N-(1-{[(6-aminohexyl)amino]carbonyl}-2-methylpropyl)-N-methyltridecanamide | 425.70 | n/a | 426.4 424.4 | 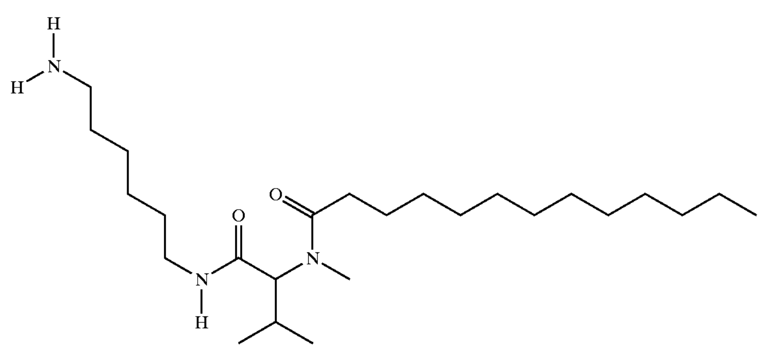 |

TABLE 1-continued (Examples 2–140):

| Ex. No. | Structure | IUPAC Name | MW | | |
|---|---|---|---|---|---|
| 23 | 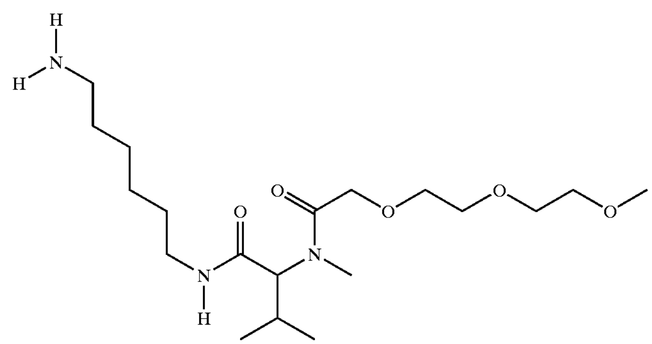 | N-(6-aminohexyl)-11-methyl-12-(1-methylethyl)-10-oxo-2,5,8-trioxa-11-azatridecan-13-amide | 389.54 | n/a 390.2 | 388.0 |
| 24 | 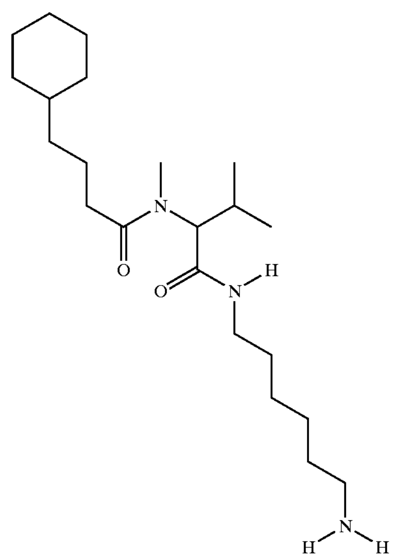 | N-(6-aminohexyl)-2-[(4-cyclohexylbutanoyl)(methyl)amino]-3-methylbutanamide | 381.61 | n/a 382.2 | 380.2 |

TABLE 1-continued
(Examples 2–140):
| Ex. No. | Structure | IUPAC Name | MW | | |
|---|---|---|---|---|---|
| 25 | 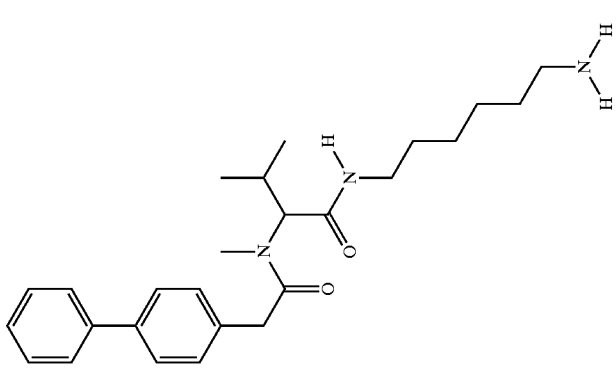 | N-(6-aminohexyl)-2-[[[1,1'-biphenyl]-4-ylacetyl)(methyl)amino]-3-methylbutanamide | 423.60 | 85% | 424.2 422.4 |

TABLE 1-continued
(Examples 2–140):
| Ex. No. | IUPAC Name | MW | | | Structure |
|---|---|---|---|---|---|
| 26 | N-(6-aminohexyl)-3-methyl-2-[methyl({4-[(phenylmethyl)oxy]phenyl}acetyl)amino]butanamide | 453.63 | 83% | 454.2 452.2 | 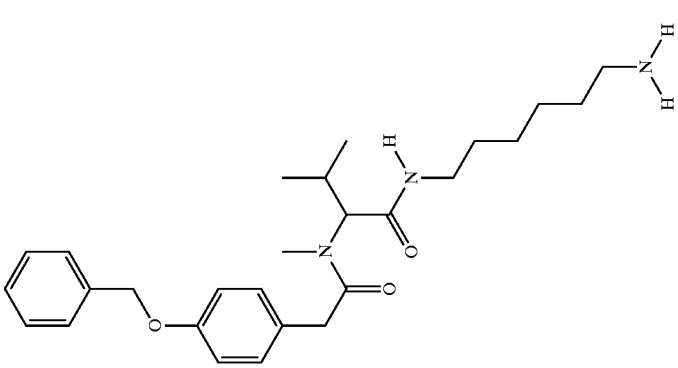 |

TABLE 1-continued (Examples 2-140):

| Ex. No. | Structure | IUPAC Name | MW | | |
|---|---|---|---|---|---|
| 27 | 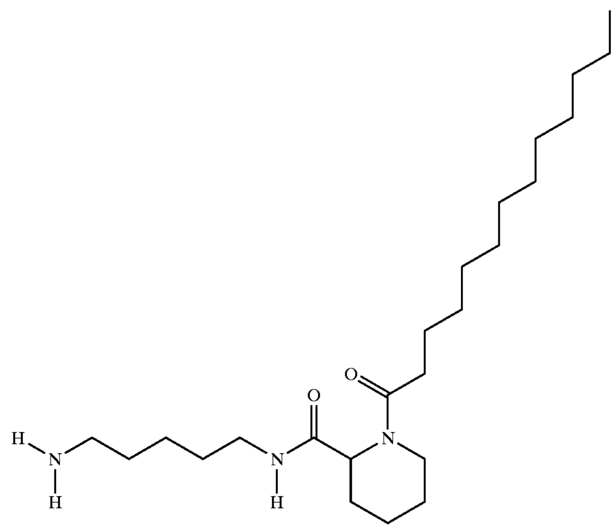 | N-(5-aminopentyl)-1-tridecanoylpiperidine-2-carboxamide | 409.66 | n/a | 410.2 408.2 |
| 28 | 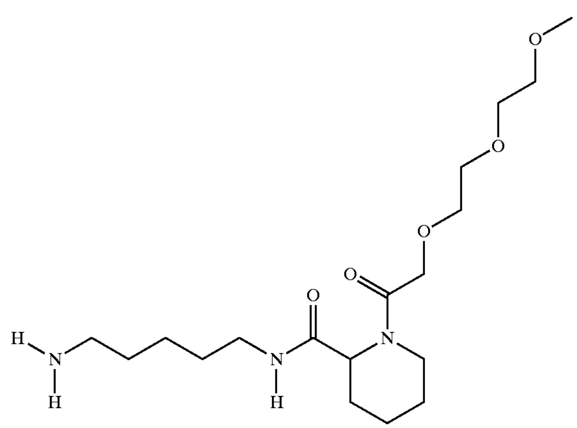 | N-(5-aminopentyl)-1-{[(2-{[2-(methyloxy)ethyl]oxy}ethyl)oxy]acetyl}piperidine-2-carboxamide | 373.50 | n/a | 374.0 372.2 |

TABLE 1-continued (Examples 2-140):

| Ex. No. | Structure | IUPAC Name | MW | | |
|---|---|---|---|---|---|
| 29 | 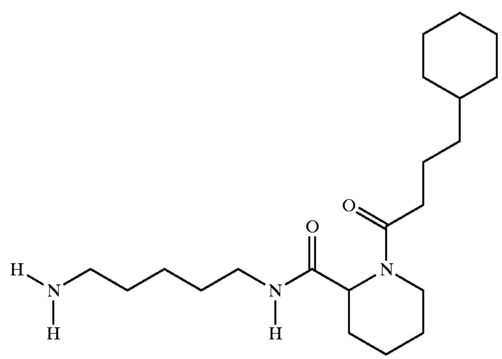 | N-(5-aminopentyl)-1-(4-cyclohexylbutanoyl)piperidine-2-carboxamide | 365.56 | n/a | 366.2 364.2 |
| 30 | 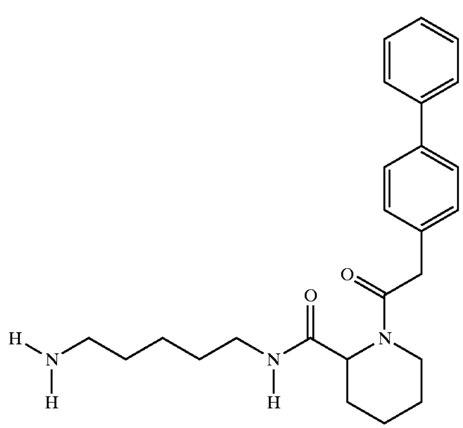 | N-(5-aminopentyl)-1-([1,1'-biphenyl]-4-ylacetyl)piperidine-2-carboxamide | 407.56 | 84% | 408.2 406.2 |

TABLE 1-continued (Examples 2-140):

| Ex. No. | Structure | IUPAC Name | MW | | |
|---|---|---|---|---|---|
| 31 | 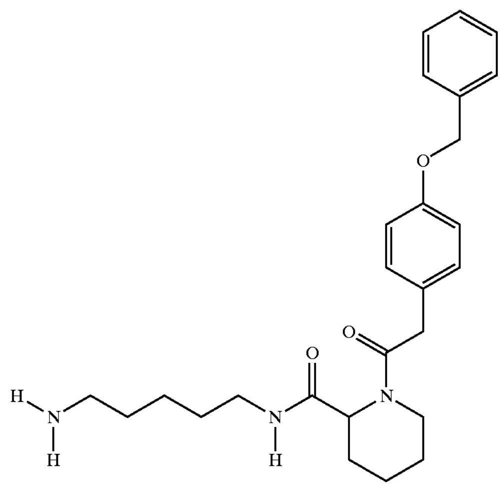 | N-(5-aminopentyl)-1-({4-[(phenylmethyl)oxy]phenyl}acetyl)piperidine-2-carboxamide | 437.59 | 82% | 438.2 436.0 |
| 32 | 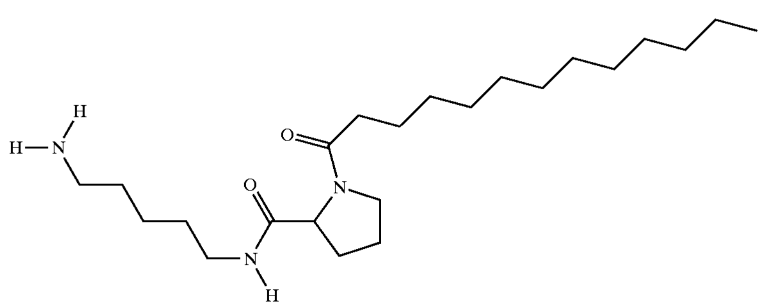 | (S)N-(5-aminopentyl)-1-tridecanoylpyrrolidine-2-carboxamide | 395.63 | n/a | 396.2 394.2 |

TABLE 1-continued (Examples 2–140):

| Ex. No. | Structure | IUPAC Name | MW | | |
|---|---|---|---|---|---|
| 33 | 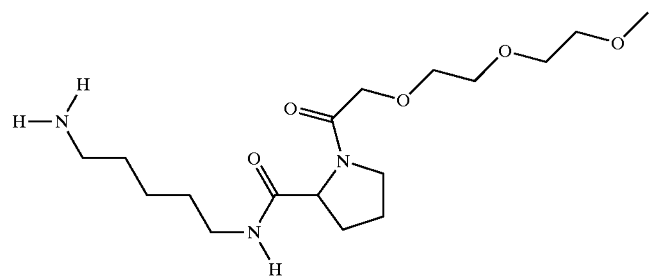 | N-(5-aminopentyl)-1-{[(2-{[2-(methyloxy)ethyl]oxy}ethyl)oxy]acetyl}pyrrolidine-2-carboxamide | 359.47 | 360.2 | 358.0 |
| 34 | 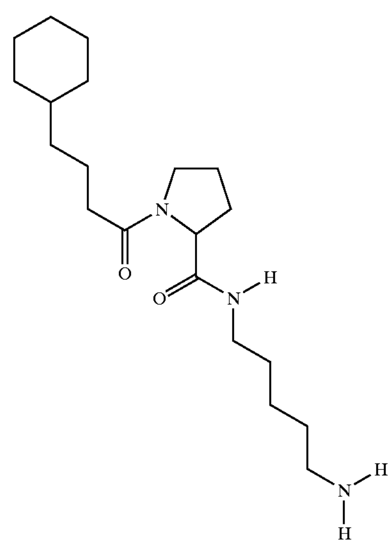 | N-(5-aminopentyl)-1-(4-cyclohexylbutanoyl)pyrrolidine-2-carboxamide | 351.54 | 352.0 | 350.0 |

TABLE 1-continued (Examples 2-140):

| Ex. No. | Structure | IUPAC Name | MW | | |
|---|---|---|---|---|---|
| 35 | ![structure] | N-(5-aminopentyl)-1-([1,1'-biphenyl]-4-ylacetyl)pyrrolidine-2-carboxamide | 393.53 | 97% | 394.2 392.0 |

TABLE 1-continued (Examples 2–140):

| Ex. No. | Structure | IUPAC Name | MW | | | |
|---|---|---|---|---|---|---|
| 36 | 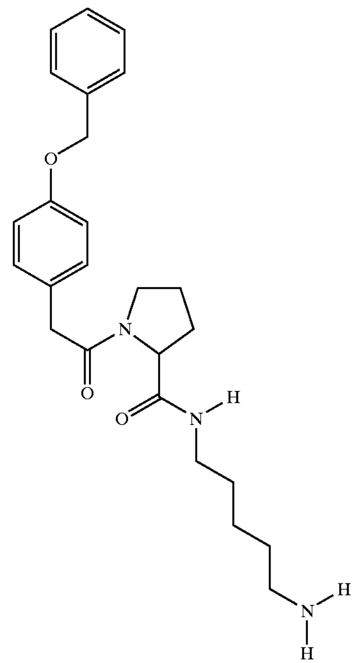 | N-(5-aminopentyl)-1-({4-[(phenylmethyl)oxy]phenyl}acetyl)pyrrolidine-2-carboxamide | 423.56 | 97% | 424.2 | 422.2 |
| 37 | 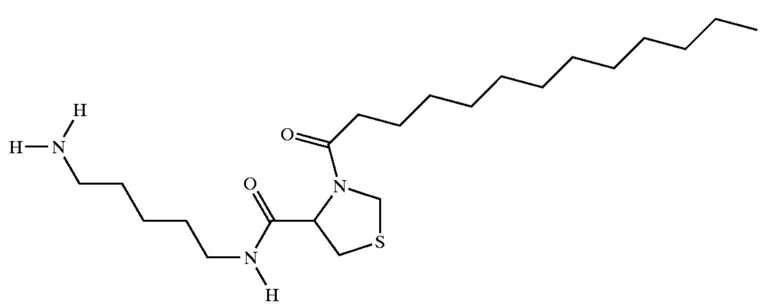 | N-(5-aminopentyl)-3-tridecanoyl-1,3-thiazolidine-4-carboxamide | 413.67 | n/a | 414.2 | 412.0 |

TABLE 1-continued
(Examples 2–140):
| Ex. No. | Structure | IUPAC Name | MW | | |
|---|---|---|---|---|---|
| 38 | 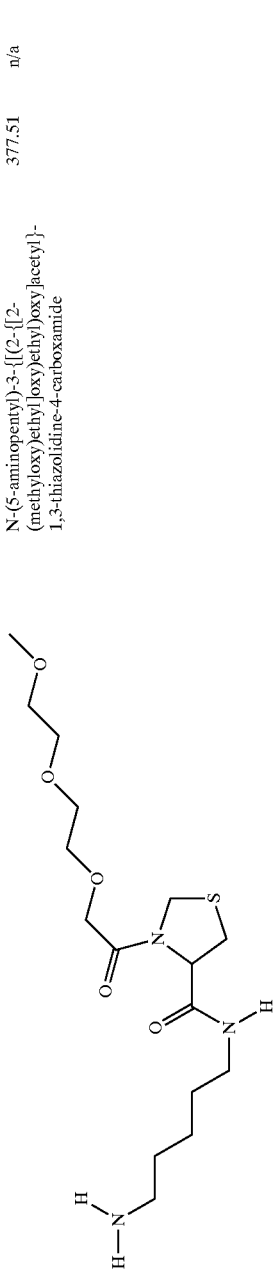 | N-(5-aminopentyl)-3-{[(2-{[2-(methyloxy)ethyl]oxy}ethyl)oxy]acetyl}-1,3-thiazolidine-4-carboxamide | 377.51 | n/a | 378.0 | 376.0 |
| 39 |  | N-(5-aminopentyl)-3-(4-cyclohexylbutanoyl)-1,3-thiazolidine-4-carboxamide | 369.57 | n/a | 370.2 | 368.2 |

TABLE 1-continued
(Examples 2–140):
| Ex. No. | Structure | IUPAC Name | MW | | |
|---|---|---|---|---|---|
| 47 | 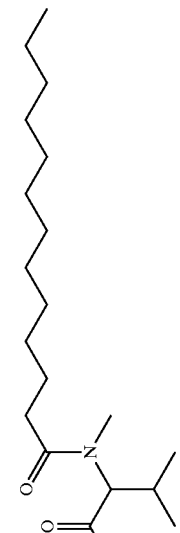 | N-(1-{[(5-aminopentyl)amino]carbonyl}-2-methylpropyl)-N-methyltridecanamide | 411.68 | 412.2 | 410.4 |
| 48 | 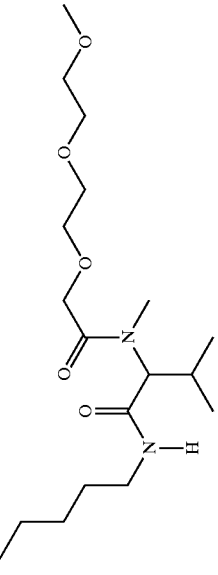 | N-(5-aminopentyl)-11-methyl-12-(1-methylethyl)-10-oxo-2,5,8-trioxa-11-azatridecan-13-amide | 375.51 | 376.2 | 374.0 |

TABLE 1-continued (Examples 2–140):

| Ex. No. | Structure | IUPAC Name | MW | | |
|---|---|---|---|---|---|
| 49 | 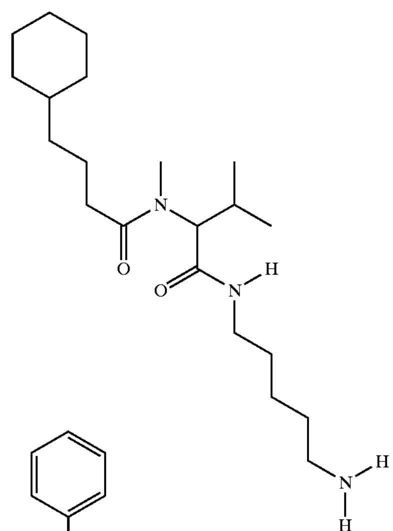 | N-(5-aminopentyl)-2-[(4-cyclohexylbutanoyl)(methyl)amino]-3-methylbutanamide | 367.58 | n/a | 368.2 366.2 |
| 50 | 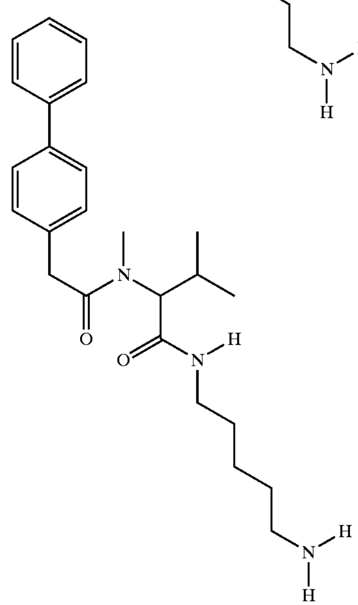 | N-(5-aminopentyl)-2-[[(1,1'-biphenyl]-4-ylacetyl)(methyl)amino]-3-methylbutanamide | 409.58 | 86% | 410.2 408.0 |

TABLE 1-continued (Examples 2-140):

| Ex. No. | Structure | IUPAC Name | MW | | |
|---|---|---|---|---|---|
| 51 | 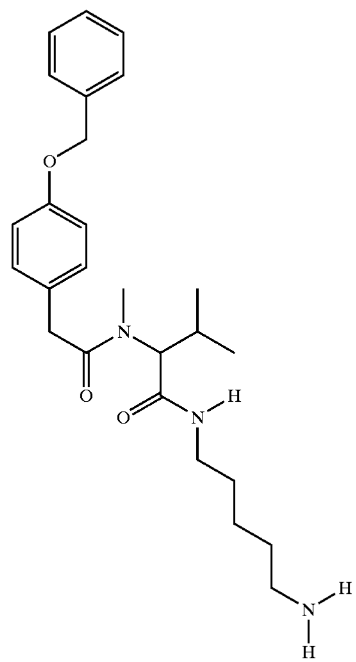 | N-(5-aminopentyl)-3-methyl-2-[methyl({4-[(phenylmethyl)oxy]phenyl}acetyl)amino]butanamide | 439.60 | 84% | 440.2 438.0 |

TABLE 1-continued (Examples 2-140):

| Ex. No. | Structure | IUPAC Name | MW | | |
|---|---|---|---|---|---|
| 52 | | N-(7-aminoheptyl)-1-tridecanoylpiperidine-2-carboxamide | 437.72 | n/a | 438.4 | 436.4 |
| 53 | | N-(7-aminoheptyl)-1-{[(2-{[2-(methyloxy)ethyl]oxy}ethyl)oxy]acetyl}piperidine-2-carboxamide | 401.55 | n/a | 402.2 | 400.0 |

TABLE 1-continued (Examples 2-140):

| Ex. No. | Structure | IUPAC Name | MW | | |
|---|---|---|---|---|---|
| 54 | (structure) | N-(7-aminoheptyl)-1-(4-cyclohexylbutanoyl)piperidine-2-carboxamide | 393.62 | 394.2 | 392.2 |
| | | | | n/a | |
| 55 | (structure) | N-(7-aminoheptyl)-1-([1,1'-biphenyl]-4-ylacetyl)piperidine-2-carboxamide | 435.61 | 436.2 | 434.0 |
| | | | | 84% | |

TABLE 1-continued (Examples 2–140):

| Ex. No. | Structure | IUPAC Name | MW | | |
|---|---|---|---|---|---|
| 56 | | N-(7-aminoheptyl)-1-({4-[(phenylmethyl)oxy]phenyl}acetyl)piperidine-2-carboxamide | 465.64 | 85% | 466.2 | 464.0 |
| 57 | | N-(7-aminoheptyl)-1-tridecanoylpyrrolidine-2-carboxamide | 423.69 | n/a | 424.4 | 422.4 |

TABLE 1-continued
(Examples 2–140):
| Ex. No. | Structure | IUPAC Name | MW | | |
|---|---|---|---|---|---|
| 58 | 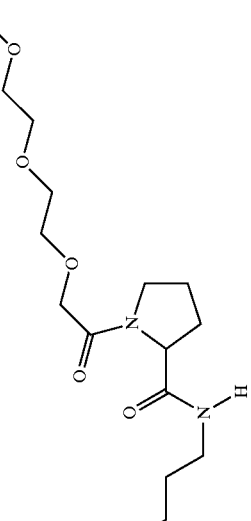 | N-(7-aminoheptyl)-1-{[(2-{[2-(methyloxy)ethyl]oxy}ethyl)oxy]acetyl}pyrrolidine-2-carboxamide | 387.52 | n/a | 388.2 386.0 |
| 59 | 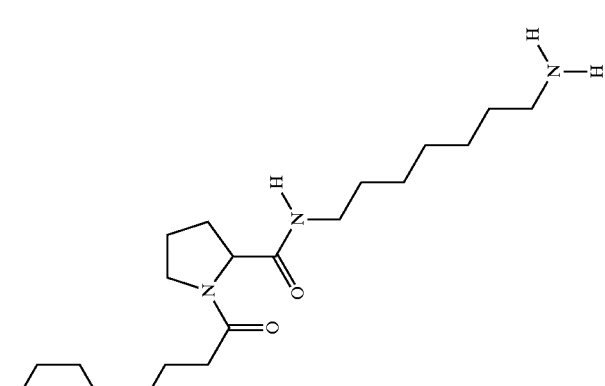 | N-(7-aminoheptyl)-1-(4-cyclohexylbutanoyl)pyrrolidine-2-carboxamide | 379.59 | n/a | 380.2 378.0 |

TABLE 1-continued (Examples 2-140):

| Ex. No. | Structure | IUPAC Name | MW | | | |
|---|---|---|---|---|---|---|
| 60 | 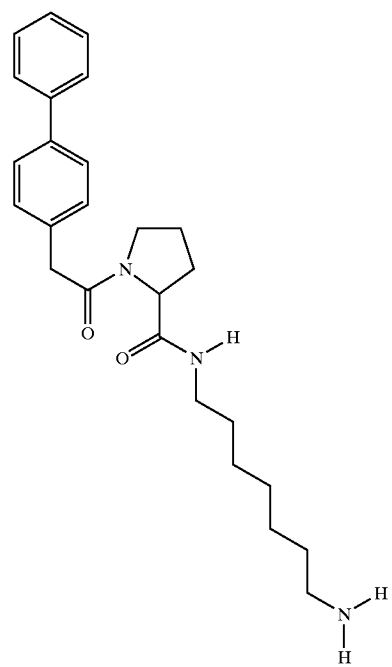 | N-(7-aminoheptyl)-1-([1,1'-biphenyl]-4-ylacetyl)pyrrolidine-2-carboxamide | 421.59 | 97% | 422.2 | 420.2 |

TABLE 1-continued
(Examples 2-140):
| Ex. No. | Structure | IUPAC Name | MW | | | |
|---|---|---|---|---|---|---|
| 67 | 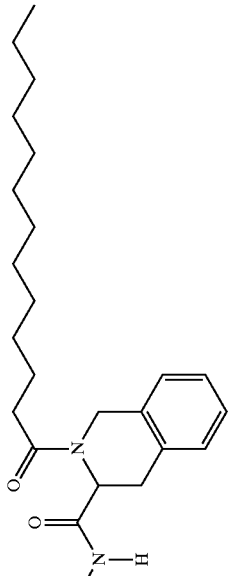 | N-(7-aminoheptyl)-2-tridecanoyl-1,2,3,4-tetrahydroisoquinoline-3-carboxamide | 485.76 | 97% | 486.2 | 484.2 |
| 68 | 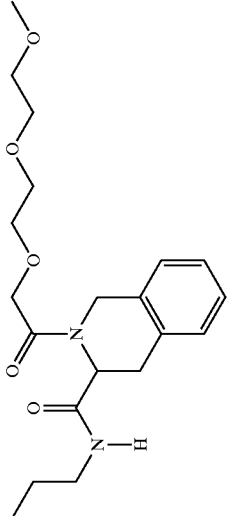 | N-(7-aminoheptyl)-2-{[(2-{[2-(methyloxy)ethyl]oxy}ethyl)oxy]acetyl}-1,2,3,4-tetrahydroisoquinoline-3-carboxamide | 449.60 | 97% | 450.2 | 448.2 |

TABLE 1-continued (Examples 2-140):

| Ex. No. | Structure | IUPAC Name | MW | | | |
|---|---|---|---|---|---|---|
| 69 | 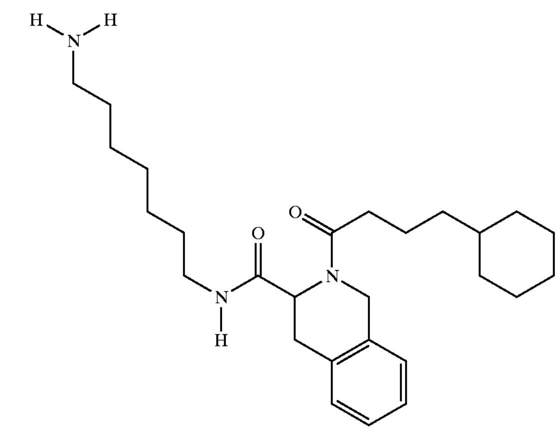 | N-(7-aminoheptyl)-2-(4-cyclohexylbutanoyl)-1,2,3,4-tetrahydroisoquinoline-3-carboxamide | 441.66 | 94% | 442.2 | 440.4 |
| 70 | 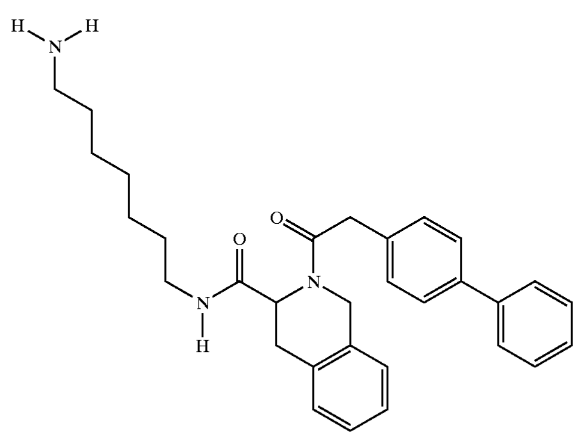 | N-(7-aminoheptyl)-2-([1,1'-biphenyl]-4-ylacetyl)-1,2,3,4-tetrahydroisoquinoline-3-carboxamide | 483.66 | 93% | 484.2 | 482.0 |

TABLE 1-continued (Examples 2–140):

| Ex. No. | Structure | IUPAC Name | MW | | |
|---|---|---|---|---|---|
| 71 | 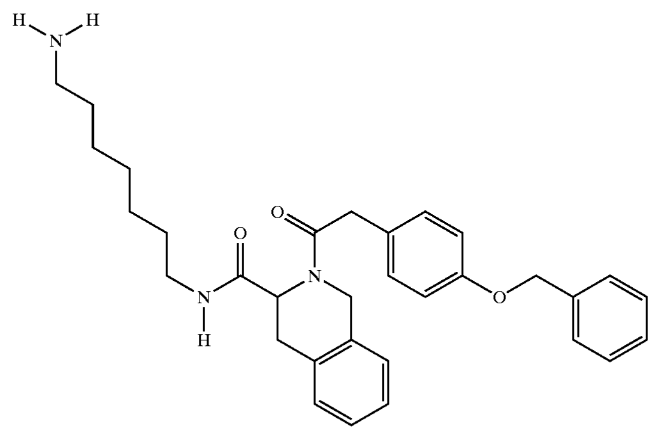 | N-(7-aminoheptyl)-2-({4-[(phenylmethyl)oxy]phenyl}acetyl)-1,2,3,4-tetrahydroisoquinoline-3-carboxamide | 513.69 | 93% | 514.2 512.2 |
| 72 | 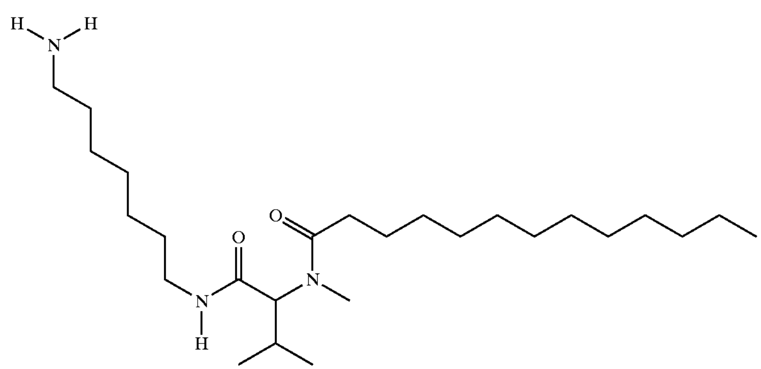 | N-(1-{[(7-aminoheptyl)amino]carbonyl}-2-methylpropyl)-N-methyltridecanamide | 439.73 | n/a | 440.4 438.4 |

TABLE 1-continued (Examples 2-140):

| Ex. No. | Structure | IUPAC Name | MW | | |
|---|---|---|---|---|---|
| 73 | 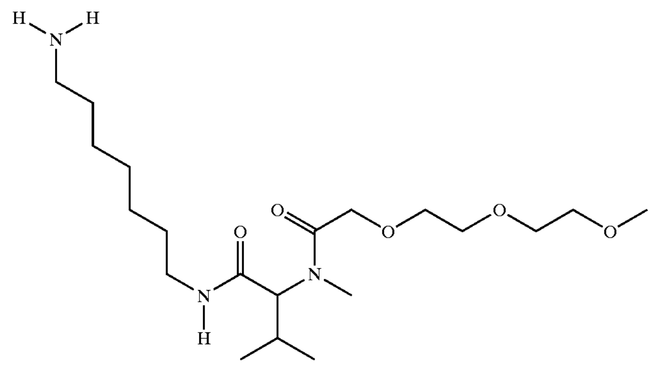 | N-(7-aminoheptyl)-11-methyl-12-(1-methylethyl)-10-oxo-2,5,8-trioxa-11-azatridecan-13-amide | 403.57 | n/a | 404.2 402.0 |
| 74 | 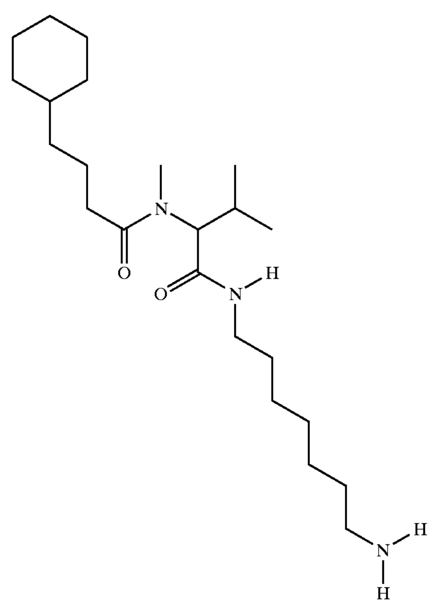 | N-(7-aminoheptyl)-2-[(4-cyclohexylbutanoyl)(methyl)amino]-3-methylbutanamide | 395.63 | n/a | 396.2 394.2 |

TABLE 1-continued
(Examples 2–140):
| Ex. No. | Structure | IUPAC Name | MW | | |
|---|---|---|---|---|---|
| 75 | 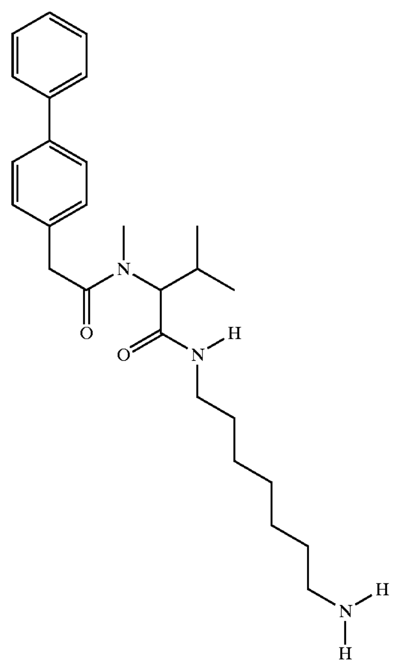 | N-(7-aminoheptyl)-2-[[[1,1'-biphenyl]-4-ylacetyl](methyl)amino]-3-methylbutanamide | 437.63 | 88% | 438.2 436.2 |

TABLE 1-continued
(Examples 2-140):
| Ex. No. | Structure | IUPAC Name | MW | | |
|---|---|---|---|---|---|
| 76 | 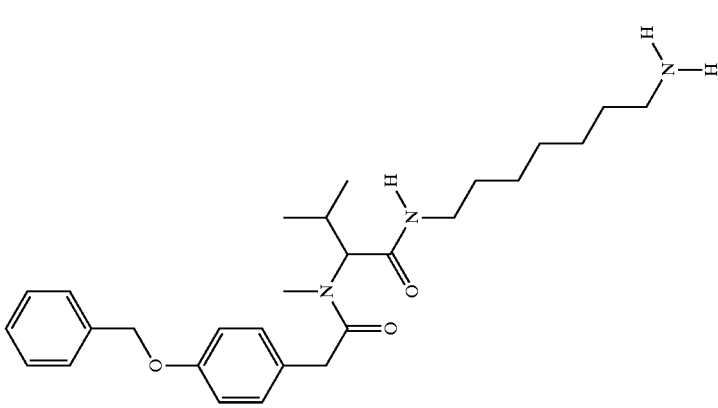 | N-(7-aminoheptyl)-3-methyl-2-[methyl({4-[(phenylmethyl)oxy]phenyl}acetyl)amino]butanamide | 467.66 | 78% | 468.2 466.2 |

TABLE 1-continued (Examples 2-140):

| Ex. No. | Structure | IUPAC Name | MW | | |
|---|---|---|---|---|---|
| 77 | 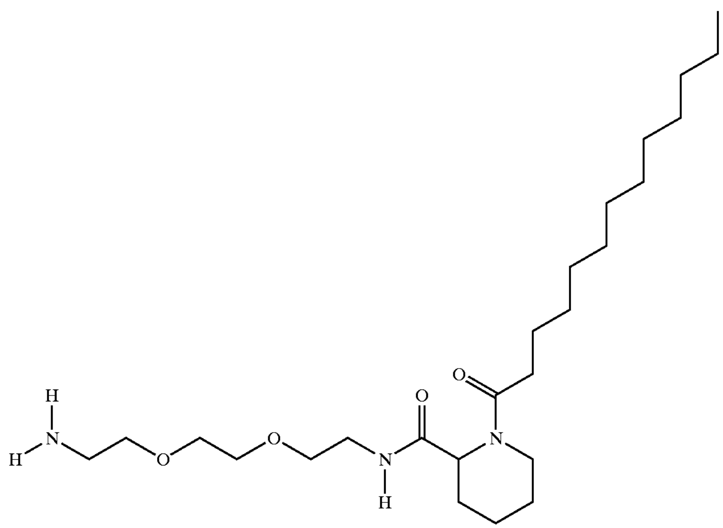 | N-[2-({2-[(2-aminoethyl)oxy]ethyl}oxy)ethyl]-1-tridecanoylpiperidine-2-carboxamide | 455.69 | n/a | 456.2 454.4 |
| 78 | 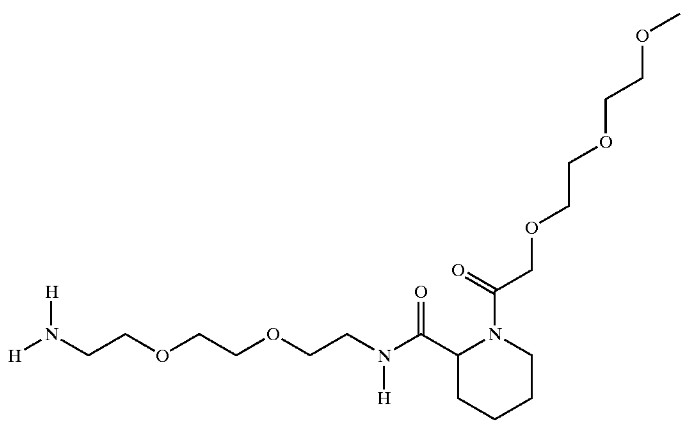 | N-[2-({2-[(2-aminoethyl)oxy]ethyl}oxy)ethyl]-1-{[(2-{[2-(methyloxy)ethyl]oxy}ethyl)oxy]acetyl}piperidine-2-carboxamide | 419.52 | n/a | 420.2 418.2 |

TABLE 1-continued (Examples 2-140):

| Ex. No. | Structure | IUPAC Name | MW | | | |
|---|---|---|---|---|---|---|
| 79 | 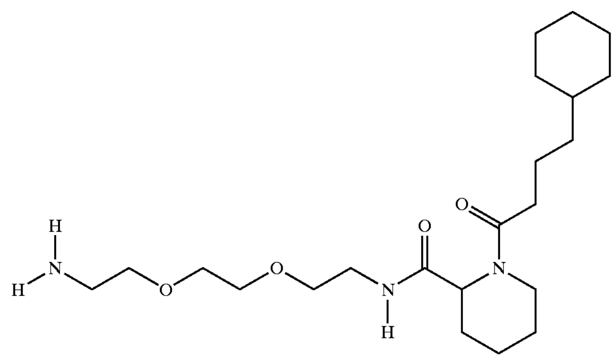 | N-[2-({2-[(2-aminoethyl)oxy]ethyl}oxy)ethyl]-1-4-cyclohexylbutanoyl)piperidine-2-carboxamide | 411.59 | n/a | 412.2 | 410.2 |
| 80 | 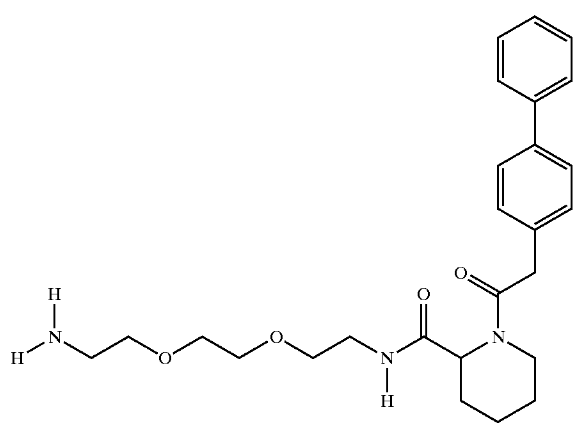 | N-[2-({2-[(2-aminoethyl)oxy]ethyl]-1-([1,1'-biphenyl]-4-ylacetyl)piperidine-2-carboxamide | 453.59 | 80% | 454.2 | 452.2 |

TABLE 1-continued (Examples 2-140):

| Ex. No. | Structure | IUPAC Name | MW | | | |
|---|---|---|---|---|---|---|
| 81 | 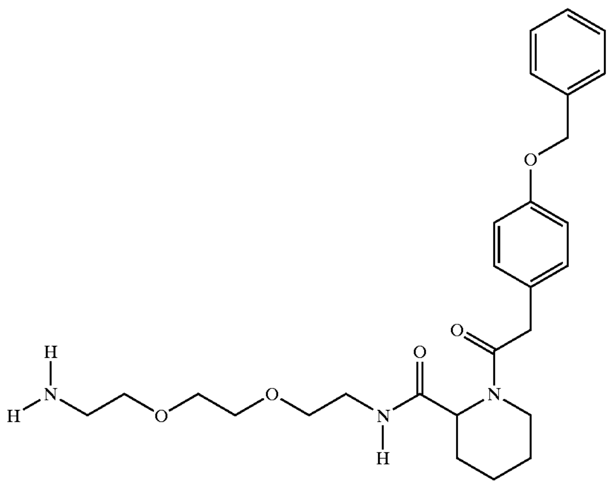 | N-[2-({2-[(2-aminoethyl)oxy]ethyl}oxy)ethyl]-1-({4-[(phenylmethyl)oxy]phenyl}acetyl)piperidine-2-carboxamide | 483.61 | 77% | 484.2 | 482.2 |
| 82 | 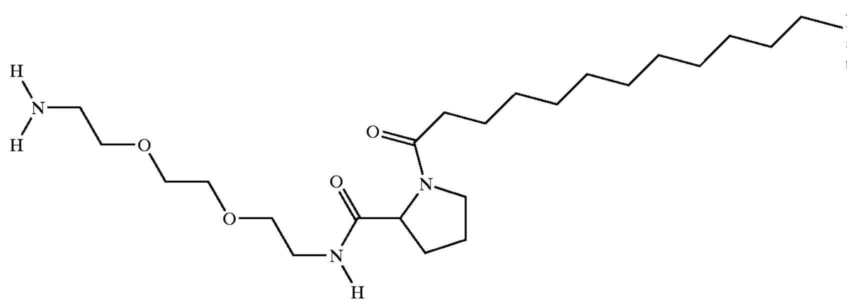 | N-[2-({2-[(2-aminoethyl)oxy]ethyl}oxy)ethyl]-1-tridecanoylpyrrolidine-2-carboxamide | 441.66 | n/a | 442.2 | 440.2 |

TABLE 1-continued (Examples 2–140):

| Ex. No. | Structure | IUPAC Name | MW | | |
|---|---|---|---|---|---|
| 83 | 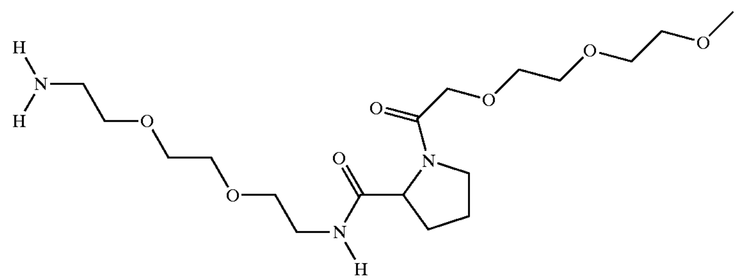 | N-[2-({2-[(2-aminoethyl)oxy]ethyl}oxy)ethyl]-1-{[(2-{[2-(methyloxy)ethyl]oxy}ethyl)oxy]acetyl}pyrrolidine-2-carboxamide | 405.50 | 406.2 | 404.0 |
| 84 | 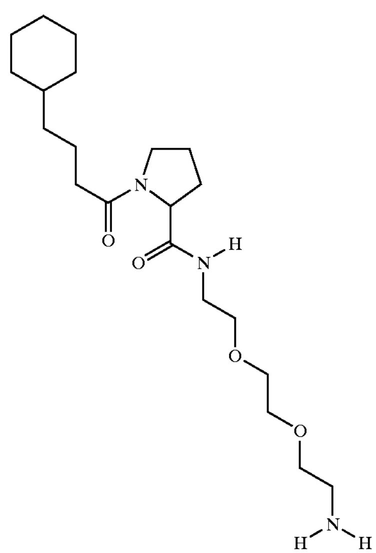 | N-[2-({2-[(2-aminoethyl)oxy]ethyl}oxy)ethyl]-1-4-cyclohexylbutanoyl)pyrrolidine-2-carboxamide | 397.56 | 398.2 | 396.2 |

TABLE 1-continued (Examples 2–140):

| Ex. No. | Structure | IUPAC Name | MW | | | |
|---|---|---|---|---|---|---|
| 85 | 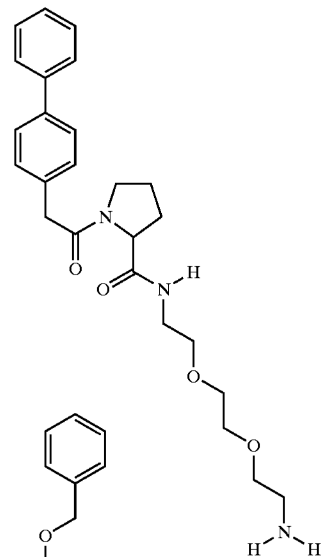 | N-[2-({2-[(2-aminoethyl)oxy]ethyl}-1-{[1,1'-biphenyl]-4-ylacetyl)pyrrolidine-2-carboxamide | 439.56 | 95% | 440.2 | 438.2 |
| 86 | 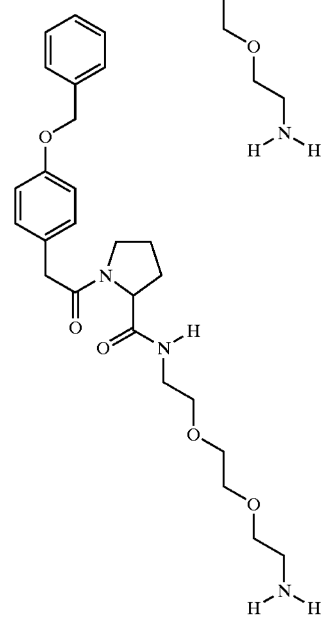 | N-[2-({2-[(2-aminoethyl)oxy]ethyl]-1-({4-[(phenylmethyl)oxy]phenyl}acetyl)pyrrolidine-2-carboxamide | 469.59 | 96% | 470.2 | 468.0 |

TABLE 1-continued (Examples 2-140):

| Ex. No. | IUPAC Name | MW | | |
|---|---|---|---|---|
| 87 | N-[2-({2-[(2-aminoethyl)oxy]ethyl}oxy)ethyl]-3-tridecanoyl-1,3-thiazolidine-4-carboxamide | 459.70 | n/a | 460.2 458.2 |
| 88 | N-[2-({2-[(2-aminoethyl)oxy]ethyl}oxy)ethyl]-3-{[(2-(methyloxy)ethyl]oxy)acetyl]-1,3-thiazolidine-4-carboxamide | 423.53 | n/a | 424.2 422.2 |
| 89 | N-[2-({2-[(2-aminoethyl)oxy]ethyl}oxy)ethyl]-3-(4-cyclohexylbutanoyl)-1,3-thiazolidine-4-carboxamide | 415.60 | n/a | 416.0 414.2 |

TABLE 1-continued (Examples 2–140):

| Ex. No. | Structure | IUPAC Name | MW | | | |
|---|---|---|---|---|---|---|
| 90 | 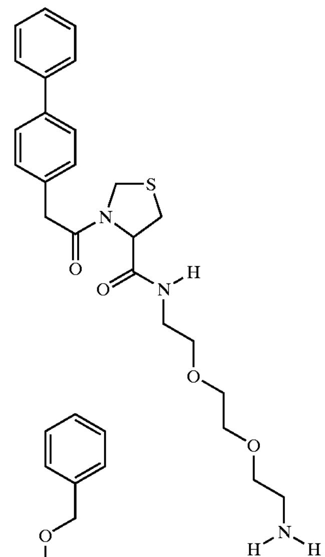 | N-[2-({2-[(2-aminoethyl)oxy]ethyl}oxy)ethyl]-3-({[1,1'-biphenyl]-4-ylacetyl)-1,3-thiazolidine-4-carboxamide | 457.60 | 91% | 458.0 | 456.0 |
| 91 | 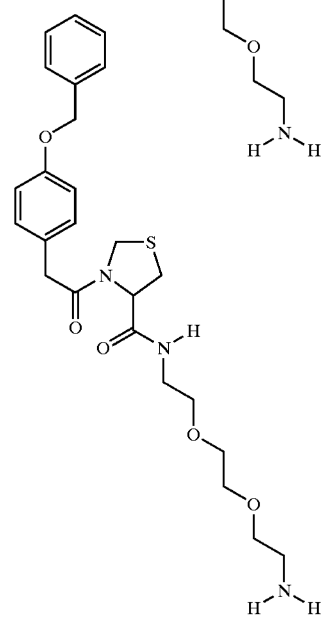 | N-[2-({2-[(2-aminoethyl)oxy]ethyl}oxy)ethyl]-3-({4-[(phenylmethyl)oxy]phenyl}acetyl)-1,3-thiazolidine-4-carboxamide | 487.62 | 92% | 488.0 | 486.0 |

TABLE 1-continued
(Examples 2–140):
| Ex. No. | Structure | IUPAC Name | MW | | |
|---|---|---|---|---|---|
| 99 | 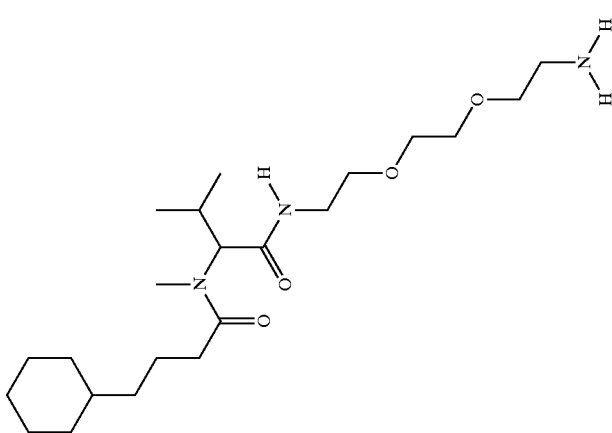 | N-[2-({2-[(2-aminoethyl)oxy]ethyl}oxy)ethyl]-2-[(4-cyclohexylbutanoyl)(methyl)amino]-3-methylbutanamide | 413.61 | n/a | 414.2 412.2 |

TABLE 1-continued (Examples 2–140):

| Ex. No. | Structure | IUPAC Name | MW | | | |
|---|---|---|---|---|---|---|
| 100 | 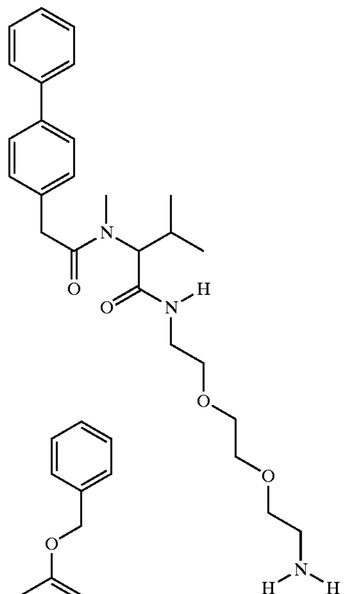 | N-[2-({2-[(2-aminoethyl)oxy]ethyl}oxy)ethyl]-2-[([1,1'-biphenyl]-4-ylacetyl)(methyl)amino]-3-methylbutanamide | 455.60 | 78% | 456.2 | 454.2 |
| 101 | 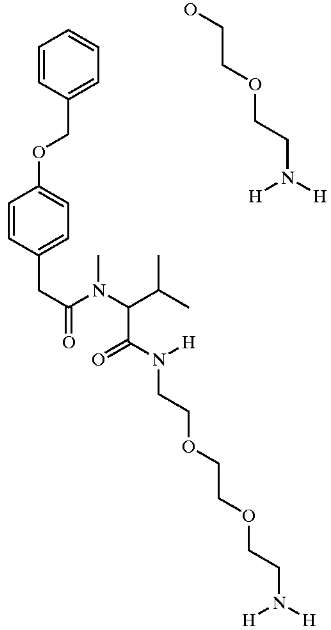 | N-[2-({2-[(2-aminoethyl)oxy]ethyl}oxy)ethyl]-3-methyl-2-[methyl({4-[(phenylmethyl)oxy]phenyl}acetyl)amino]butanamide | 485.63 | 61% | 486.0 | 484.0 |

TABLE 1-continued
(Examples 2–140):
| Ex. No. | Structure | IUPAC Name | MW | | |
|---|---|---|---|---|---|
| 102 | 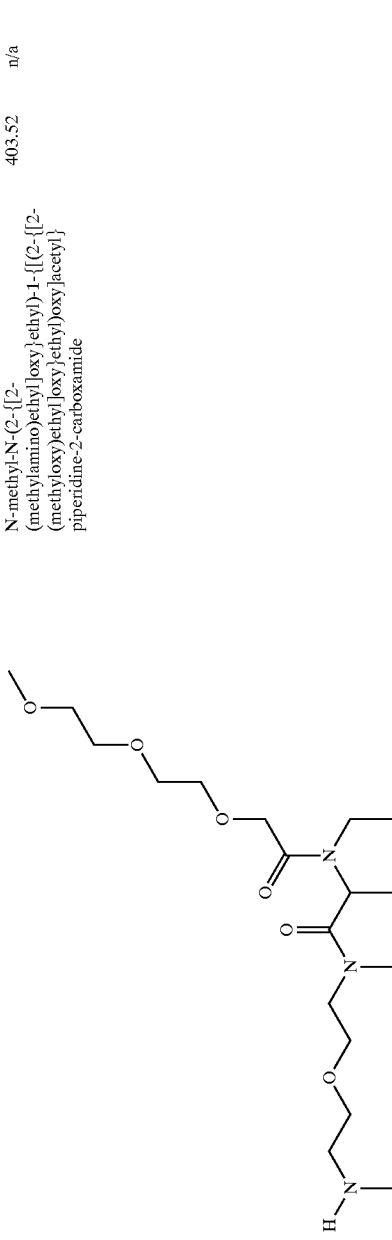 | N-methyl-N-(2-{[2-(methylamino)ethyl]oxy}ethyl)-1-{[(2-{[2-(methyloxy)ethyl]oxy}ethyl)oxy]acetyl}piperidine-2-carboxamide | 403.52 | 404.0 | 418.2 |
| 103 | 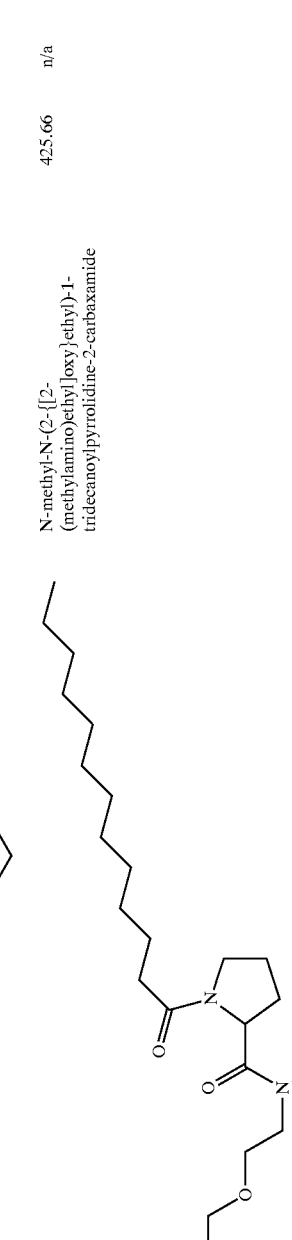 | N-methyl-N-(2-{[2-(methylamino)ethyl]oxy}ethyl)-1-tridecanoylpyrrolidine-2-carboxamide | 425.66 | n/a | 426.2 | — |
| 104 | 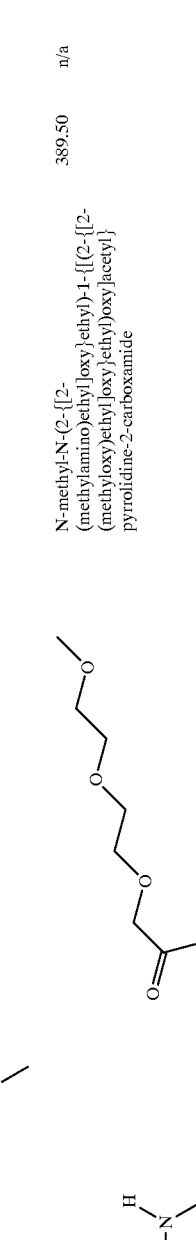 | N-methyl-N-(2-{[2-(methylamino)ethyl]oxy}ethyl)-1-{[(2-{[2-(methyloxy)ethyl]oxy}ethyl)oxy]acetyl}pyrrolidine-2-carboxamide | 389.50 | n/a | 390.2 | — |

TABLE 1-continued (Examples 2–140):

| Ex. No. | Structure | IUPAC Name | MW | | |
|---|---|---|---|---|---|
| 105 | | 1-(4-cyclohexylbutanoyl)-N-methyl-N-(2-{[2-(methylamino)ethyl]oxy}ethyl)pyrrolidine 2-carboxamide | 381.56 | n/a | 382.2 | — |
| 106 | | 1-([1,1'-biphenyl]-4-ylacetyl)-N-methyl-N-(2-{[2-(methylamino)ethyl]oxy}ethyl)pyrrolidine 2-carboxamide | 423.56 | 86% | 424.2 | — |

TABLE 1-continued (Examples 2-140):

| Ex. No. | Structure | IUPAC Name | MW | | |
|---|---|---|---|---|---|
| 107 | | N-methyl-N-(2-{[2-(methylamino)ethyl]oxy}ethyl)-1-({4-[(phenylmethyl)oxy]phenyl}acetyl)pyrrolidine-2-carboxamide | 453.59 | 85% | 454.0 | — |
| 108 | | N-methyl-N-(2-{[2-(methylamino)ethyl]oxy}ethyl)-3-tridecanoyl-1,3-thiazolidine-4-carboxamide | 443.70 | n/a | 444.4 | — |

TABLE 1-continued (Examples 2-140):

| Ex. No. | Structure | IUPAC Name | MW | | |
|---|---|---|---|---|---|
| 109 | | N-methyl-N-(2-{[2-(methylamino)ethyl]oxy}ethyl)-3-{[(2-{[2-(methyloxy)ethyl]oxy}ethyl)acetyl]-1,3-thiazolidine-4-carboxamide | 407.53 | n/a | 408.0 | — |
| 110 | | 3-(4-cyclohexybutanoyl)-N-methyl-N-(2-{[2-(methylamino)ethyl]oxy}ethyl)-1,3-thiazolidine-4-carboxamide | 399.60 | n/a | 400.2 | — |

TABLE 1-continued (Examples 2–140):

| Ex. No. | Structure | IUPAC Name | MW | | | |
|---|---|---|---|---|---|---|
| 111 | 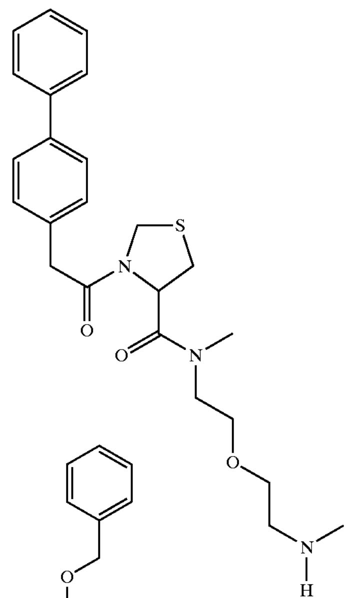 | 3-([1,1'-biphenyl]-4-ylacetyl)-N-methyl-N-(2-{[2-(methylamino)ethyl]oxy}ethyl)-1,3-thiazolidine-4-carboxamide | 441.60 | 93% | 442.2 | 440.2 |
| 112 | 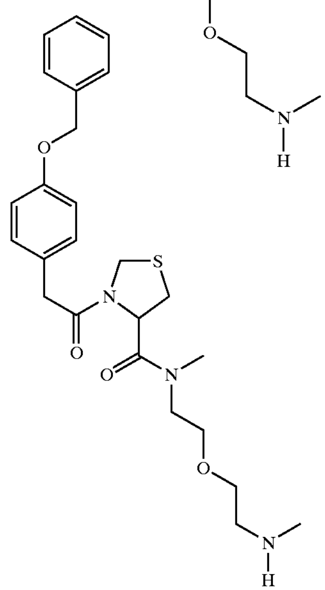 | N-methyl-N-(2-{[2-(methylamino)ethyl]oxy}ethyl)-3-({4-[(phenylmethyl)oxy]phenyl}acetyl)-1,3-thiazolidine-4-carboxamide | 471.62 | 96% | 472.2 | 470.2 |

TABLE 1-continued (Examples 2–140):

| Ex. No. | Structure | IUPAC Name | MW | | | |
|---|---|---|---|---|---|---|
| 113 | 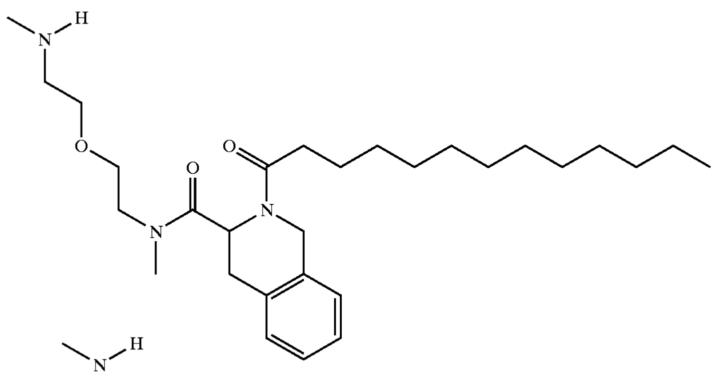 | N-methyl-N-(2-{[2-(methylamino)ethyl]oxy}ethyl)-2-tridecanoyl-1,2,3,4-tetrahydroisoquinoline-3-carboxamide | 487.73 | 91% | 488.2 | — |
| 114 | 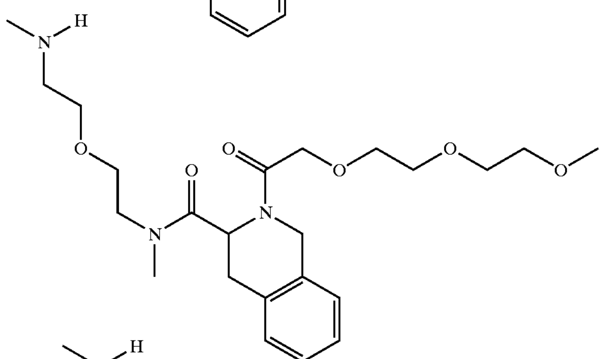 | N-methyl-N-(2-{[2-(methylamino)ethyl]oxy}ethyl)-2-{[(2-{(2-(methyloxy)ethyl]oxy}ethyl)oxy]acetyl}-1,2,3,4-tetrahydroisoquinoline-3-carboxamide | 451.57 | 97% | 452.2 | — |
| 115 | 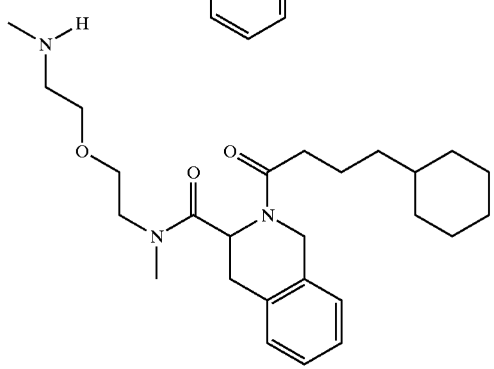 | 2-(4-cyclohexylbutanoyl)-N-methyl-N-(2-{[2-(methylamino)ethyl]oxy}ethyl)-1,2,3,4-tetrahydroisoquinoline-3-carboxamide | 443.63 | 89% | 444.4 | |

TABLE 1-continued (Examples 2–140):

| Ex. No. | Structure | IUPAC Name | MW | | | |
|---|---|---|---|---|---|---|
| 116 | 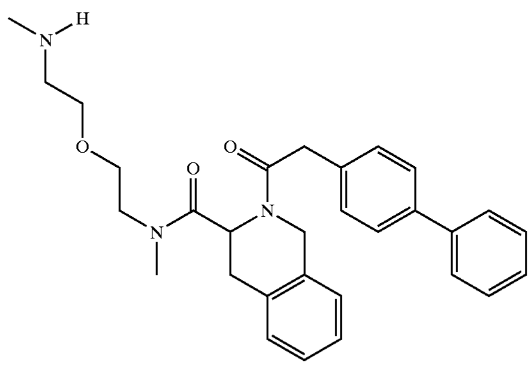 | 2-([1,1'-biphenyl]-4-ylacetyl)-N-methyl-N-(2-{[2-(methylamino)ethyl]oxy}ethyl)-1,2,3,4-tetrahydroisoquinoline-3-carboxamide | 485.63 | 93% | 486.2 | 484.2 |
| 117 | 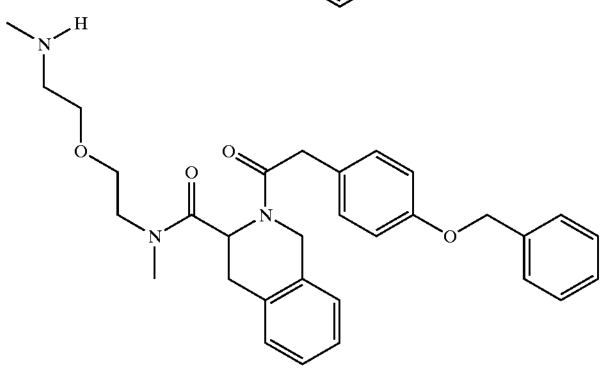 | N-methyl-N-(2-{[2-(methylamino)ethyl]oxy}ethyl)-2-({4-[(phenylmethyl)oxy]phenyl}acetyl)-1,2,3,4-tetrahydroisoquinoline-3-carbaxamide | 515.66 | 94% | 516.2 | 514.0 |
| 118 | 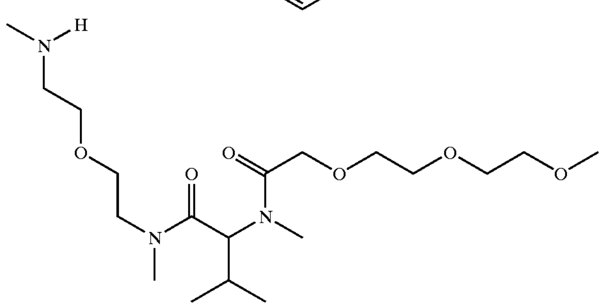 | N,11-dimethyl-N-(2-{[2-(methylamino)ethyl]oxy}ethyl)-12-(1-methylethyl)-10-oxo-2,5,8-trioxa-11-azatridecan-13-amide | 405.54 | n/a | 406.2 | — |

TABLE 1-continued (Examples 2–140):

| Ex. No. | Structure | IUPAC Name | MW | | |
|---|---|---|---|---|---|
| 119 | 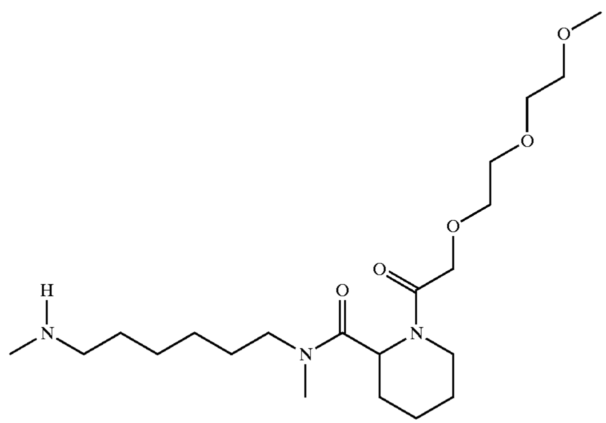 | N-methyl-N-[6-(methylamino)hexyl]-1-{[(2-{[2-(methyloxy)ethyl]oxy}ethyl)oxy]acetyl}piperidine-2-carboxamide | 415.58 | n/a | 416.2 — |
| 120 | 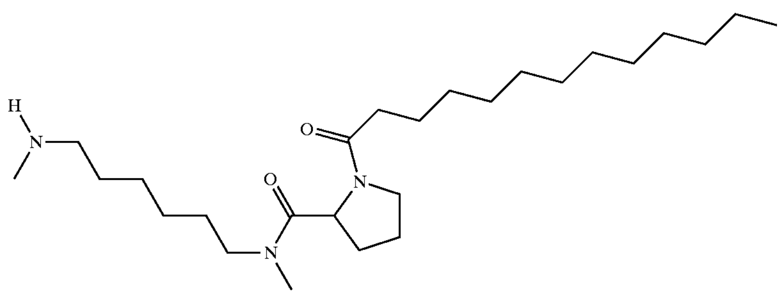 | N-methyl-N-[6-(methylamino)hexyl]-1-tridecanoylpyrrolidine-2-carboxamide | 437.72 | n/a | 438.4 — |
| 121 | 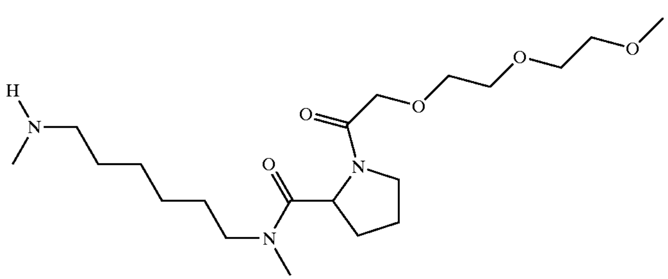 | N-methyl-N-[6-(methylamino)hexyl]-1-{[(2-{[2-(methyloxy)ethyl]oxy}ethyl)oxy]acetyl}pyrrolidine-2-carboxamide | 401.55 | n/a | 402.2 — |

TABLE 1-continued (Examples 2–140):

| Ex. No. | Structure | IUPAC Name | MW | | |
|---|---|---|---|---|---|
| 122 | | 1-(4-cyclohexylbutanoyl)-N-methyl-N-[6-(methylamino)hexyl]pyrrolidine-2-carboxamide | 393.62 | n/a | 394.2 | — |
| 123 | | 1-(1,1'-biphenyl]-4-ylacetyl)-N-methyl-N-[6-(methylamino)hexyl]pyrrolidine-2-carboxamide | 435.61 | 97% | 436.2 | — |

TABLE 1-continued (Examples 2–140):

| Ex. No. | Structure | IUPAC Name | MW | | |
|---|---|---|---|---|---|
| 124 | | N-methyl-[6-(methylamino)hexyl]-1-({4-[(phenylmethyl)oxy]phenyl}acetyl)pyrrolidine-2-carboxamide | 465.64 | 95% | 466.2 | — |
| 131 | | N-methyl-N-[6-(methylamino)hexyl]-2-{[(2-{[2-(methyloxy)ethyl]oxy}ethyl)oxy]acetyl}-1,2,3,4-tetrahydroisoquinoline-3-carboxamide | 463.62 | 95% | 464.2 | — |

TABLE 1-continued
(Examples 2-140):
| Ex. No. | IUPAC Name | MW | | | Structure |
|---|---|---|---|---|---|
| 132 | 2-(4-cyclohexylbutanoyl)-N-methyl-N-[6-(methylamino)hexyl]-1,2,3,4-tetrahydroisoquinoline-3-carboxamide | 455.69 | 91% | 456.2 | — | 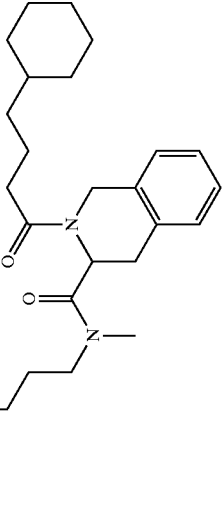 |
| 133 | 2-{[[1,1'-biphenyl]-4-ylacetyl]-N-methyl-N-[6-(methylamino)hexyl]-1,2,3,4-tetrahydroisoquinoline-3-carbaxamide | 497.69 | 91% | 498.4 | 496.0 | 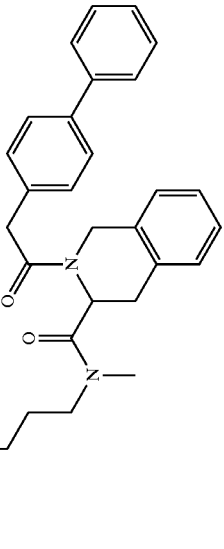 |

TABLE 1-continued (Examples 2–140):

| Ex. No. | Structure | IUPAC Name | MW | | |
|---|---|---|---|---|---|
| 134 | 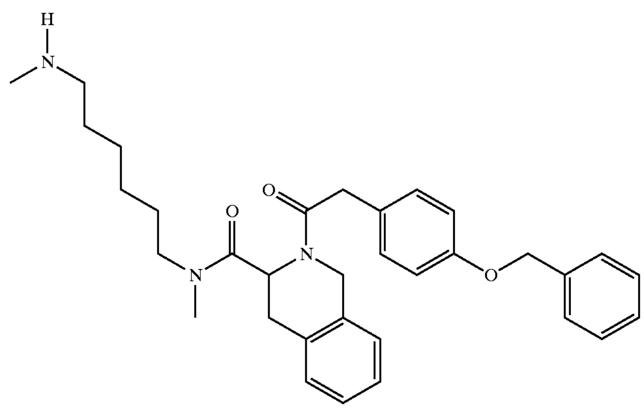 | N-methyl-N-[6-(methylamino)hexyl]-2-({4-[(phenylmethyl)oxy]phenyl}acetyl)-1,2,3,4-tetrahydroisoquinoline-3-carboxamide | 527.71 | 92% | 528.4 526.4 |
| 135 | 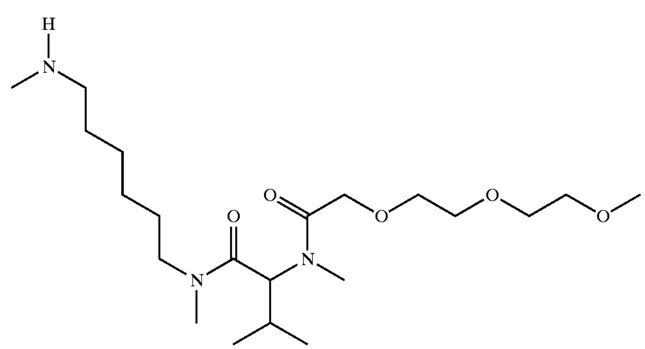 | N,11-dimethyl-N-[6-(methylamino)hexyl]-12-(1-methylethyl)-10-oxo-2,5,8-trioxa-11-azatridecan-13-amide | 417.59 | n/a | 418.2 — |

TABLE 1-continued (Examples 2–140):

| Ex. No. | Structure | IUPAC Name | MW | | |
|---|---|---|---|---|---|
| 136 | 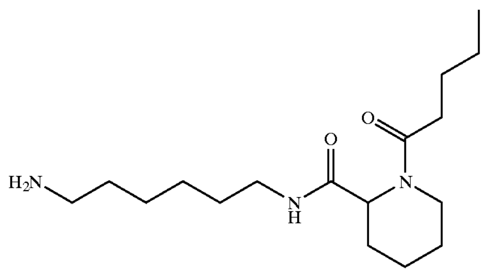 | N-(6-aminohexyl)-1-pentanoylpiperidine 2-carboxamide | 311.47 | 100% | 310.2 312.2 |
| 137 | 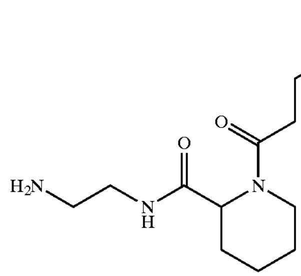 | N-(2-aminoethyl)-1-pentanoylpipendine 2-carboxamide | 255.36 | 90% | 254.2 256.2 |
| 138 | 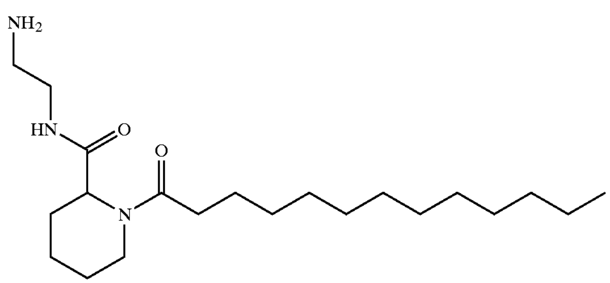 | N-(2-aminoethyl)-1-trideeanoylpiperidine-2-carboxamide | 367.58 | 93% | 368.0 366.2 |

TABLE 1-continued (Examples 2-140):

| Ex. No. | Structure | IUPAC Name | MW | | |
|---|---|---|---|---|---|
| 139 | | (R)-N-(5-aminopentyl)-1-tridecanoylpyrrolidine-2-carboxamide | 395.63 | n/a | 396.2 | 394.2 |
| 140 | | (R)-N-(6-aminohexyl)-1-tridecanoylpyrrolidine-2-carboxamide | 409.66 | n/a | 410.2 | N/a |

Example 141 through 188

The compounds of to examples 141 through 188 were prepared according to the procedure outlined in scheme III by using the corresponding precursors and starting materials. Thereby, the oxime resin of formula XII may be Oxime Resin from Novabiochem, while the amino carboxylic acids of formula II may be chosen among those set out in Examples 2 to 140 for the compounds of formula IIA. Also, the carboxylic acids and sulfonly chlorides may be chosen among those set out in Examples 2 to 140 for compounds VA and VB. The primary or secondary amines of formula III such as N,N-dimethylpropane-1,3-diamine, or N,N-diethylbutane-1,3-diamine are commerciably available or may be obtained by using methods that are known to a person skilled in the art. The reaction procedure and conditions are adapted from the one set out in Example 2. The overall yield ranges between 70 to 90%.

TABLE 2

(Examples 141–188)

| Ex. No. | Structure | IUPAC Name | MW |
|---|---|---|---|
| 141 | 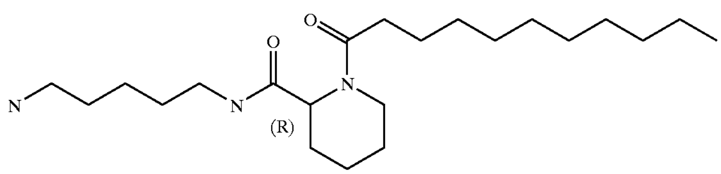 | (R)-1-Undecanoyl-piperidine-2-carboxylic acid (5-amino-pentyl)-amide | 381.61 |
| 142 | 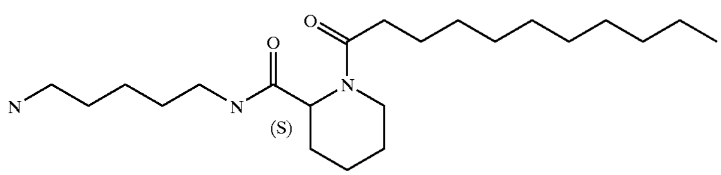 | (S)-1-Undecanoyl-piperidine-2-carboxylic acid (5-amino-pentyl)-amide | 381.61 |
| 143 | 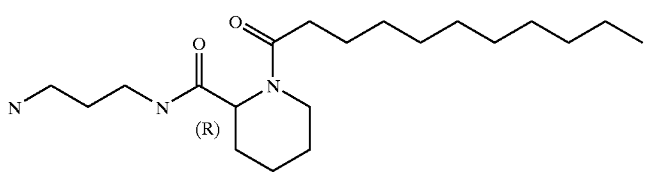 | (R)-1-Undecanoyl-piperidine-2-carboxylic acid (3-amino-propyl)-amide | 353.55 |
| 144 | 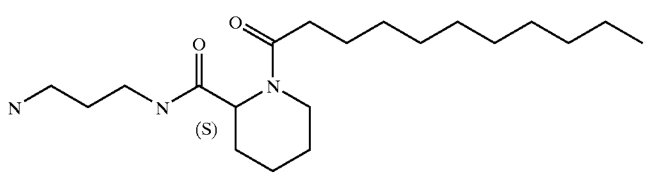 | (S)-1-Undecanoyl-piperidine-2-carboxylic acid (3-amino-propyl)-amide | 353.55 |
| 145 | 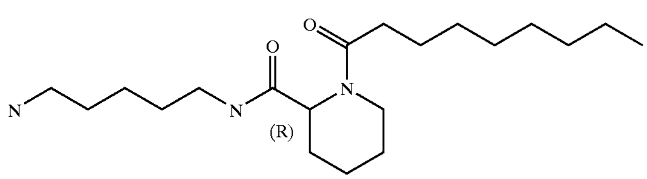 | (R)-1-Nonanoyl-piperidine-2-carboxylic acid(5-amino-pentyl)-amide | 353.55 |
| 146 | 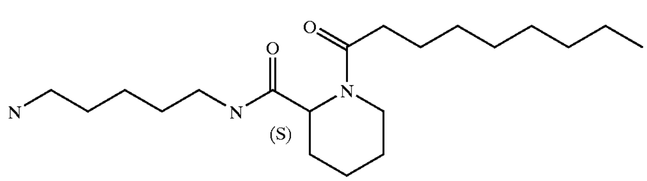 | (S)-1-Nonanoyl-piperidine-2-carboxylic acid(5-amino-pentyl)-amide | 353.55 |
| 147 | 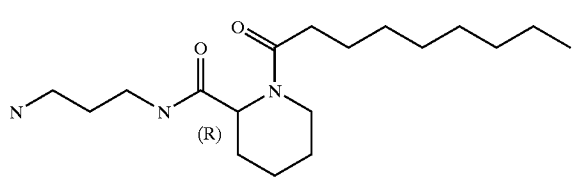 | (R)-1-Nonanoyl-piperidine-2-carboxylic acid(3-amino-propyl)-amide | 325.50 |

TABLE 2-continued (Examples 141–188)

| Ex. No. | Structure | IUPAC Name | MW |
|---|---|---|---|
| 148 | 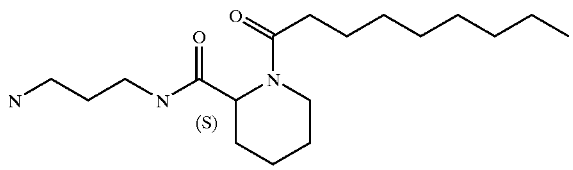 | (S)-1-Nonanoyl-piperidine-2-carboxylic acid(3-amino-propyl)-amide | 325.50 |
| 149 | 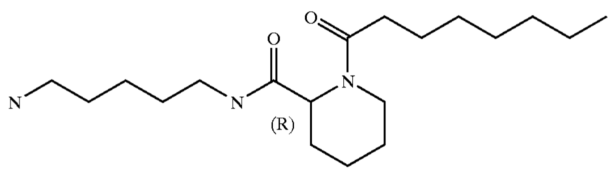 | (R)-1-Octanoyl-piperidine-2-carboxylic acid(5-amino-pentyl)-amide | 339.53 |
| 150 | 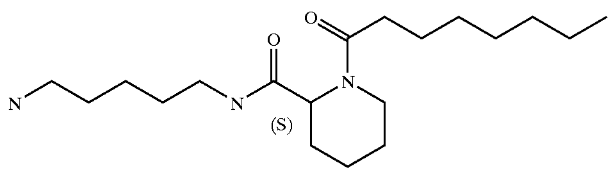 | (S)-1-Octanoyl-piperidine-2-carboxylic acid(5-amino-pentyl)-amide | 339.53 |
| 151 | 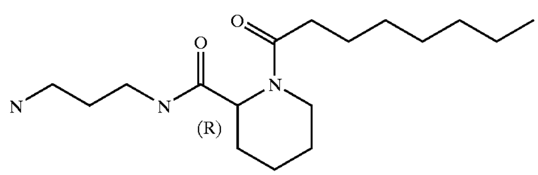 | (R)-1-Octanoyl-piperidine-2-carboxylic acid(3-amino-propyl)-amide | 311.47 |
| 152 | 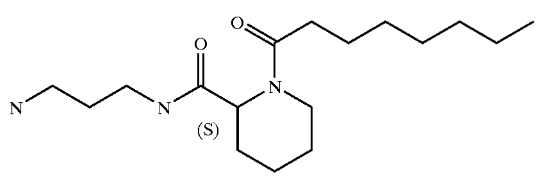 | (S)-1-Octanoyl-piperidine-2-carboxylic acid(3-amino-propyl)-amide | 311.47 |
| 153 | 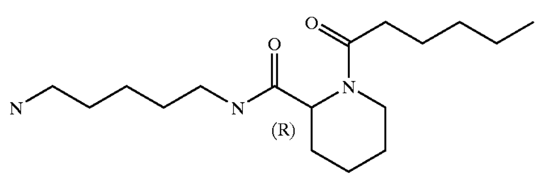 | (R)-1-Hexanoyl-piperidine-2-carboxylic acid(5-amino-pentyl)-anide | 311.47 |
| 154 | 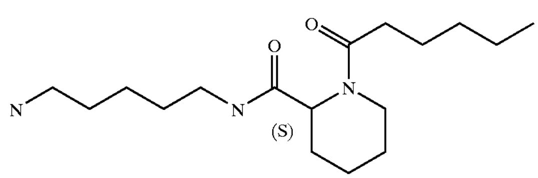 | (S)-1-Hexanoyl-piperidine-2-carboxylic acid(5-amino-pentyl)-amide | 311.47 |
| 155 | 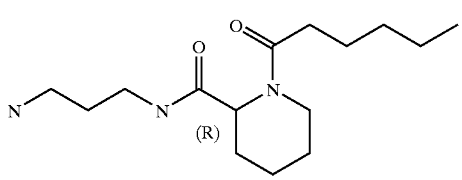 | (R)-1-Hexanoyl-piperidine-2-carboxylic acid(3-amino-propyl)-amide | 283.42 |

TABLE 2-continued (Examples 141–188)

| Ex. No. | Structure | IUPAC Name | MW |
|---|---|---|---|
| 156 | 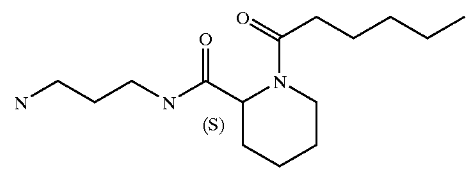 | (S)-1-Hexanoyl-piperidine-2-carboxylic acid(3-amino-propyl)-amide | 283.42 |
| 157 | 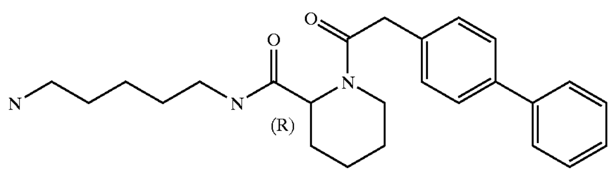 | (R)-1-(2-Biphenyl-4-yl-ethanoyl)-piperidine-2-carboxylic acid(5-amino-pentyl)-amide | 407.56 |
| 158 | 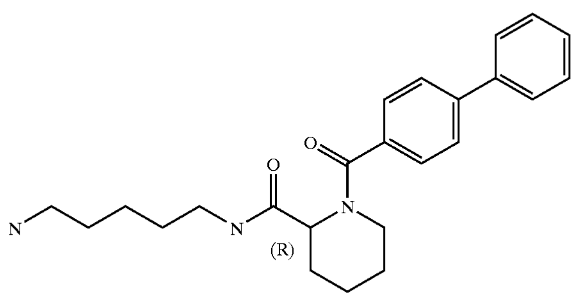 | (R)-1-(1-Biphenyl-4-yl-methanoyl)-piperidine-2-carboxylic acid(5-amino-pentyl)-amide | 393.53 |
| 159 | 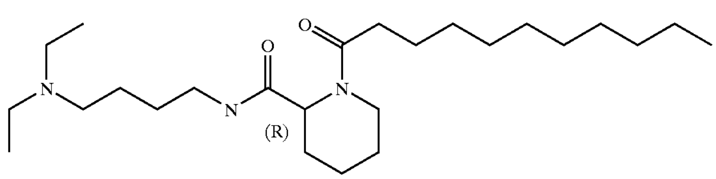 | (R)-1-Undecanoyl-piperidine-2-carboxylic acid (4-diethylamino-butyl)-amide | 423.69 |
| 160 | 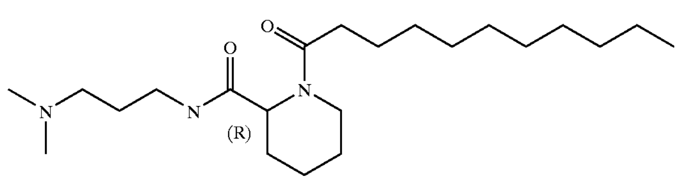 | (R)-1-Undecanoyl-piperidine-2-carboxylic acid (3-dimethylamino-propyl-amide | 381.61 |
| 161 | 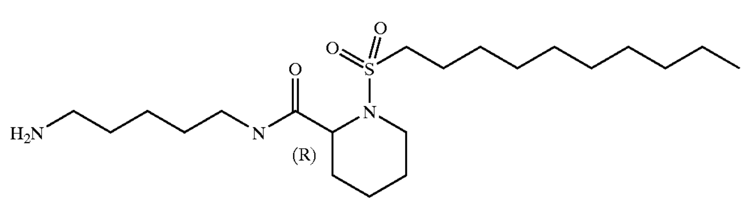 | (R)-1-(Decane-1-sulfonyl)-piperidine-2-carboxylic acid (5-amino-pentyl)-amide | 417.66 |
| 162 | 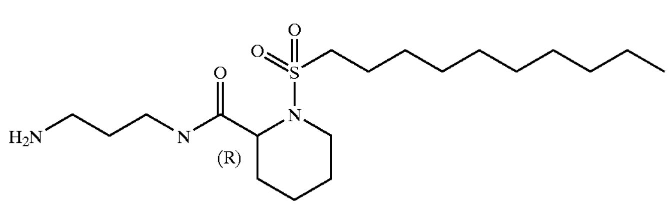 | (R)-1-(Decane-1-sulfonyl)-piperidine-2-carboxylic acid (3-amino-propyl)-amide | 389.60 |

TABLE 2-continued (Examples 141–188)

| Ex. No. | Structure | IUPAC Name | MW |
|---|---|---|---|
| 163 | 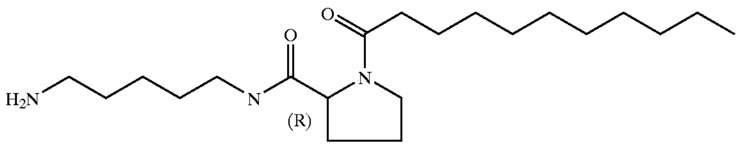 | (R)-1-Undecanoyl-pyrrolidine-2-carboxylic acid (5-amino-pentyl)-amide | 357.58 |
| 164 | 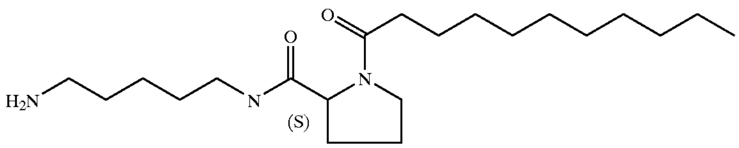 | (S)-1-Undecanoyl-pyrrolidine-2-carboxylic acid (5-amino-pentyl)-amide | 357.58 |
| 165 | 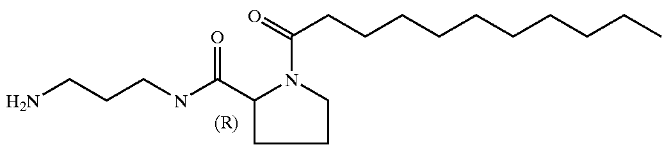 | (R)-1-Undecanoyl-pyrrolidine-2-carboxylic acid (3-amino-propyl)-amide | 339.53 |
| 166 | 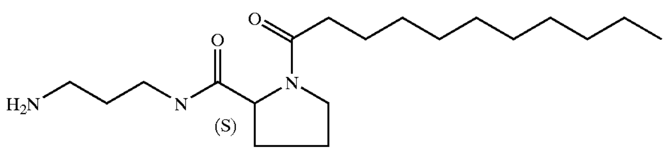 | (S)-1-Undecanoyl-pyrrolidine-2-carboxylic acid (3-amino-propyl)-amide | 339.53 |
| 167 | 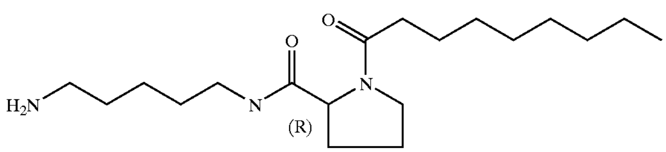 | (R)-1-Nonanoyl-pyrrolidine-2-carboxylic acid(5-amino-pentyl)-amide | 339.53 |
| 168 | 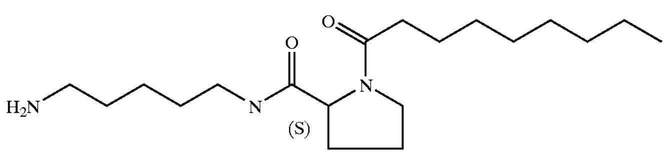 | (S)-1-Nonanoyl-pyrrolidine-2-carboxylic acid(5-amino-pentyl)-amide | 339.53 |
| 169 | 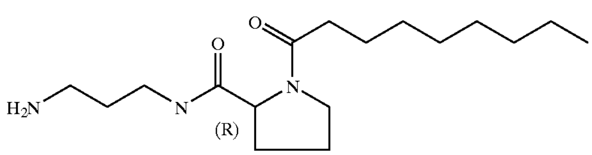 | (R)-1-Nonanoyl-pyrrolidine-2-carboxylic acid(3-amino-propyl)-amide | 311.47 |
| 170 | 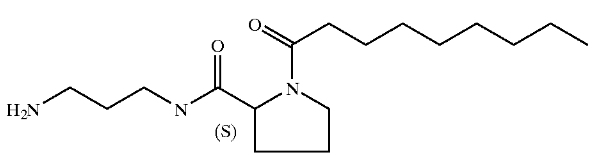 | (S)-1-Nonanoyl-pyrrolidine-2-carboxylic acid(3-amino-propyl)-amide | 311.47 |
| 171 | 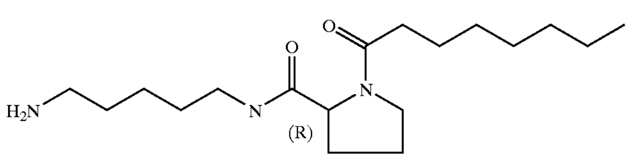 | (R)-1-Octanoyl-pyrrolidine-2-carboxylic acid(5-amino-pentyl)-amide | 325.50 |

TABLE 2-continued (Examples 141–188)

| Ex. No. | Structure | IUPAC Name | MW |
|---|---|---|---|
| 172 | 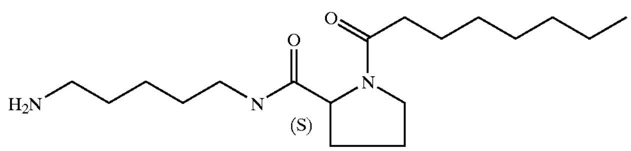 | (S)-1-Octanoyl-pyrrolidine-2-carboxylic acid(5-amino-pentyl)-amide | 325.50 |
| 173 | 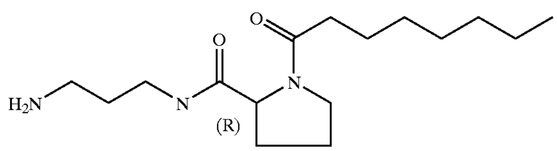 | (R)-1-Octanoyl-pyrrolidine-2-carboxylic acid(3-amino-propyl)-amide | 297.44 |
| 174 | 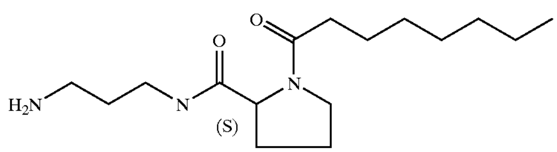 | (S)-1-Octanoyl-pyrrolidine-2-carboxylic acid(3-amino-propyl)-amide | 297.44 |
| 175 | 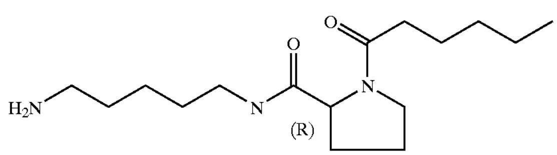 | (R)-1-Hexanoyl-pyrrolidine-2-carboxylic acid(5-amino-pentyl)-amide | 297.44 |
| 176 | 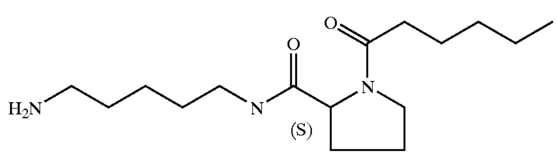 | (S)-1-Hexanoyl-pyrrolidine-2-carboxylic acid(5-amino-pentyl)-amide | 297.44 |
| 177 | 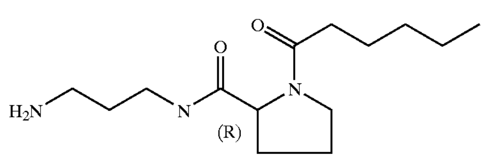 | (R)-1-Hexanoyl-pyrrolidine-2-carboxylic acid(3-amino-propyl)-amide | 269.39 |
| 178 | 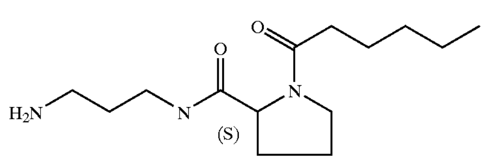 | (S)-1-Hexanoyl-pyrrolidine-2-carboxylic acid(3-amino-propyl)-amide | 269.39 |
| 179 | 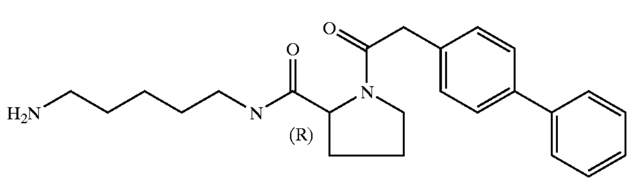 | (R)-1-(2-Biphenyl-4-yl-ethanoyl)-pyrrolidine-2-carboxylic acid(5-amino-pentyl)-amide | 393.53 |

TABLE 2-continued (Examples 141–188)

| Ex. No. | Structure | IUPAC Name | MW |
|---|---|---|---|
| 180 | 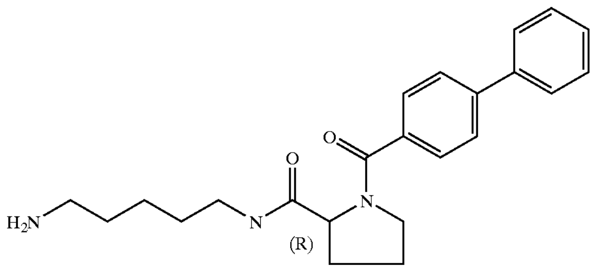 | (R)-1-(1-Biphenyl-4-yl-methanoyl)-pyrrolidine-2-carboxylic acid(5-amino-pentyl)-amide | 379.51 |
| 181 | 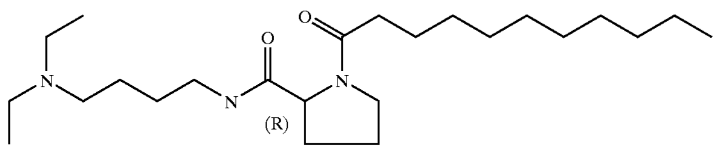 | (R)-1-Undecanoyl-pyrrolidine-2-carboxylic acid (4-diethylamino-butyl)-amide | 409.66 |
| 182 | 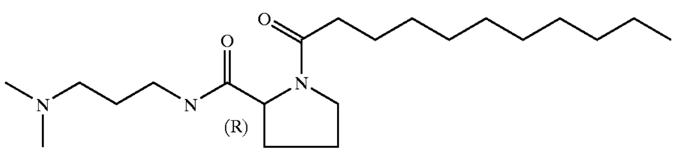 | (R)-1-Undecanoyl-pyrrolidine-2-carboxylic acid (3-dimethylamino-propyl)-amide | 367.58 |
| 183 | 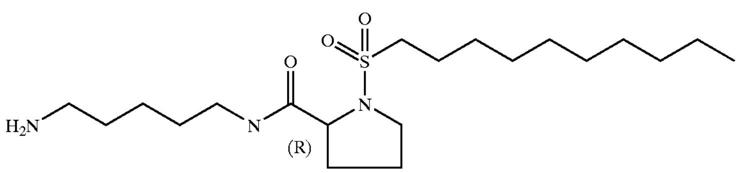 | (R)-1-(Decane-1-sulfonyl)-pyrrolidine-2-carboxylic acid (5-amino-pentyl)-amide | 403.63 |
| 184 | 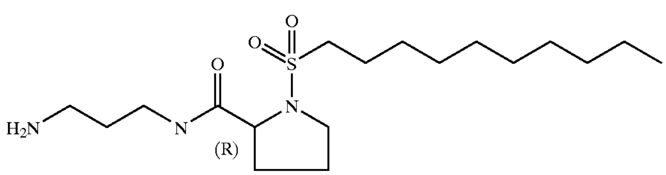 | (R)-1-(Decane-1-sulfonyl)-pyrrolidine-2-carboxylic acid (3-amino-propyl)-amide | 375.58 |
| 185 | 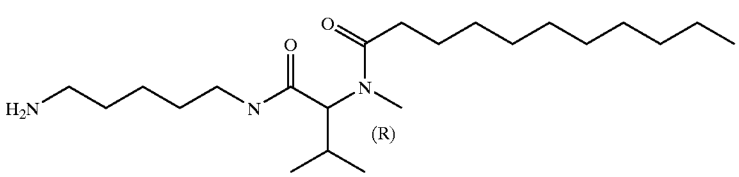 | (R)-N-(5-Aminopentyl)-methyl-C-(methyl-undecanoyl-amino)-butyramide | 383.62 |
| 186 | 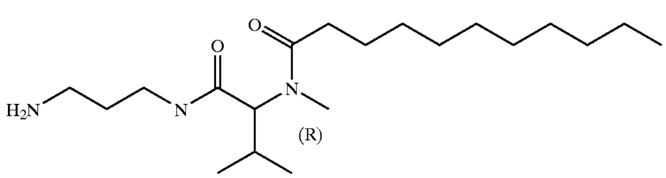 | (R)-N-(3-Aminopropyl)-methyl-C-(methyl-undecanoyl-amino)-butyramide | 355.57 |
| 187 | 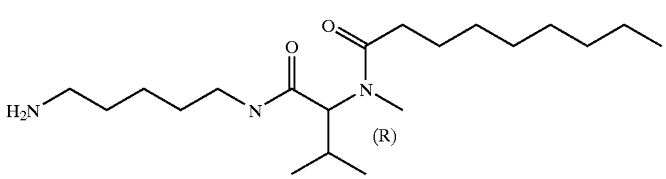 | (R)-N-(5-Aminopentyl)-methyl-C-(methyl-nonanoyl-amino)-butyramide | 355.57 |

TABLE 2-continued (Examples 141–188)

| Ex. No. | Structure | IUPAC Name | MW |
|---|---|---|---|
| 188 | 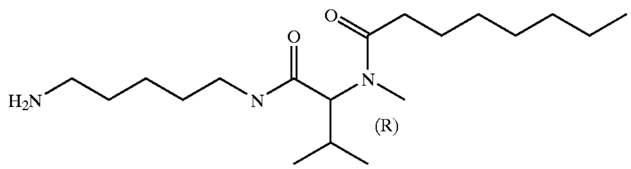 | (R)-N-(5-Aminopentyl)-methyl-C-(methyl-octanoyl-amino)butyramide | 341.54 |

Example 189

Preparation of a Pharmaceutical Formulation

The following formulation examples illustrate representative pharmaceutical compositions of this invention containing compounds according to formula I. The present invention, however, is not limited to the following pharmaceutical compositions.

Formulation 1—Tablets

A compound of formula I is admixed as a dry powder with a dry gelatin binder in an approximate 1:2 weight ration. A minor amount of magnesium stearate is added as a lubricant. The mixture is formed into 240–270 mg tablets (80–90 mg of active amino derivatives according to formula I per tablet) in a tablet press.

Formulation 2—Capsules

A compound of formula I is admixed as a dry powder with a starch diluent in an approximate 1:1 weight ratio The mixture is filled into 250 mg capsules (125 mg of active amino derivatives according to formula I per capsule).

Formulation 3—Liquid

A compound of formula 1 (1250 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

The compound of formula I is admixed as a dry powder with a dry gelatin binder in an approximate 1:2 weight ratio. A minor amount of magnesium stearate is added as a lubricant. The mixture is formed into 450–900 mg tablets (150–300 mg of active amino derivatives according to formula I) in a tablet press.

Formulation 5—Injection

The compound of formula I is dissolved in a buffered sterile saline injectable aqueous medium to a concentration of approximately 5 mg/ml.

In the following the present invention shall be illustrated by means of some examples which are not construed to be viewed as limiting the scope of the invention.

Example 190

Biological Assays a) Production of Recombinant Bax

Human Bax-α lacking 20 amino acids at the COOH-terminus is expressed as a GST fusion protein or a His-tagged protein in *Escherichia coli*, and the protein is purified from the soluble cell fraction. In brief, the GST-Bax fusion protein is applied to a glutathione-Sepha-rose column, and Bax was released by cleavage with thrombin (0.6U/mL). Bax is subsequently purified on heparin-Sepharose, followed by fast protein liquid chromatography (FPLC) Mono Q. His-tagged Bax is purified on a Ni-nitriloacetic acid-agarose column followed by FPLC MonoQ:

b) Isolation of Mitochondria

Mitochondria are isolated from mouse liver cells by differential centrifugation Cells are broken with a dounce homogenizer and the suspension is centrifuged at 2,000 g in an Eppendorf centrifuge at 4° C. This procedure is repeated until almost all the cells are broken. Supernatants from each step are pooled before centrifugation at 13,000 g at 4° C. for 10 min. The pellet is resuspended in 40 mL MB buffer and centrifuged at 2000 g for 2 min. The supernatant is removed and centrifuged at 13 kg for 4 min. The mitochondria are recovered in the 13k pellet and resuspended in MB buffer at a density of 30 OD600 nm/mL.

c) In Vitro Assay for Cytochrome c Release

Mitochondria (30 $\mu$g) from mouse liver are incubated with 200 nM recombinant Bax in the presence of various compounds (5 $\mu$M) in 200 $\mu$L of KCl buffer for 20 min at 30° C. and are then centrifuged for 4 min at 13,000 g at 4° C. Mitochondrial pellets corresponding to 1.5 $\mu$g proteins are separated by SDS-PAGE using 4–20% Tris-Gly gels (NOVEX) and their respective contents of cytochrome c are estimated by Western blotting using polyclonal anti-cytochrome c antibody (dilution 1:2,500). Antigen-antibody complexes are detected using horseradish peroxidase-conjugated goat anti-rabbit IgG and enhance chemiluminescence detection reagents. The cytochrome c bands are scanned and quantified using a Bio-Rad (GS-700 Imaging Densitometer).

By using for instance compound (7) at a concentration of 10 $\mu$M in the above assay, an inhibition about 88% was determined. According to a preferred embodiment the tested compounds of formula I display an inhibition of the cytochrome c release of at least 40%, more preferred of at least 60% when tested at a concentration of between 2–50 $\mu$M, preferably between 5–20 $\mu$M and most preferred at 5–10 $\mu$M.

d) Effect of Compounds According to Formula I onto the Release of Cytochrome c Triggered by Bid-Induced Bax Activation (In Vitro Assay)

Concerning the Bid-induced activation of Bax leading to mitochondrial Cytochrome C release, it is referred to the description of Martinou et al. in *The Journal of Cell Biology*, Vol. 144, No. 5, Mar. 8, 1999, pages 891–901 as well as Eskes, Desagher, Antonsson and Martinou in *Molecular and Cellular Biology*, February 2000, p. 929–935, Vol. 20, No. 3. Mitochondria isolated from HeLa cells are incubated for 15 min at 30° C. in 100 $\mu$l of KCl buffer in the presence or absence of 10 nM recombinant Bid. The various compounds (10 $\mu$M) are pre-incubated for 5 min prior to addition of Bid.

Following incubation, mitochondria were centrifuged for 5 min at 13000 g at 4° C. and the supernatant is collected for cytochrome c analysis. Cytochrome c is detected by Western blotting. The cytochrome c bands are scanned and quantified using a Bio-Rad (GS-700 Imaging Densitometer).

By using for instance compound (22) at a concentration of 5 $\mu$M in the above assay, an inhibition of about 95% was determined. According to a preferred embodiment the tested compounds of formula I display an inhibition of the cytochrome c release of at least 40%, more preferred of at least 60% when tested at a concentration of between 2–50 $\mu$M, preferably between 5–20 $\mu$M and most preferred at 5–10 $\mu$M.

The above set out 2 in vitro assays c) and d) involving the determination of mitochondrial cytochrome c release are based on immunochemical methods using the Western blot analysis. Alternatively, said quantitative cytochrome c determinations could be performed by using spectrophotometric means:

I. by recording the difference between reduced and oxidised cytochrome c by dual wavelength double beam spectrophotometry;

II. by measuring the rather intensive $\gamma$ or Soret peak in the spectrum of cytochrome c ($\epsilon=100$ mM$^{-1}$cm$^{-1}$) is used for rapid and quantitative determination of the release of cytochrome c from isolated mitochondria. This technique allows a highly convenient, fast and reliable quantitative determination of the release of cytochrome c.

e) Sympathetic Neuron Culture and Survival Assay (In Vitro Assay)

Sympathetic neurons from superior cervical ganglia (SCG) of newborn rats (p4) are dissociated in dispase, plated at a density of 104 cells/cm$^2$ in 48 well MTT plates coated with rat tail collagen, and cultured in Leibowitz medium containing 5% rat serum, 0.75 g/ml NGF 7S (Boehringer Mannheim Corp., Indianapolis, Ind.) and arabinosine 105M. Cell death is induced at day 4 after plating by exposing the culture to medium containing 10 g/ml of anti NGF antibody (Boehringer Mannheim Corp., Indianapolis, Ind.) and no NGF or arabinosine, in the presence or absence of amino derivatives according to formula I. 24 hours after cell death induction, determination of cell viability is performed by incubation of the culture for 1 hour, at 37° C. in 0.5 mg/ml of 3-(4,5-dimethyl-thiazol-2-yl)2,5 diphenyl tetrazolium bromide (MTT). After incubation in MTT cells are re-suspended in DMSO, transferred to a 96 MTT plate and cell viability is evaluated by measuring optical density at 590nm.

By using for instance compound (2) at a concentration of 10 $\mu$M in the above assay, a neuronal survival rate of about 41% was determined. According to a preferred embodiment, the tested compounds display a neuronal survival rate of at least 30%, preferably of at least 40%.

f) Global Ischemia In Gerbils (In Vivo)

The ability of the amine compounds of formula I to protect cell death during a stroke event may be assessed using the following protocol:

—1—METHOD
Surgery
Anesthesia: halothane or isoflurane (0.5–4%).
Sheaving of the gorge and incision of the skin.
The common carotid arteries (left and right) are freed from tissue.
Occlusion of the arteries using Bulldog microclamps during 5 min.
Disinfection of the surgery plan (Betadine®) and suture of the skin (Autoclip® or Michel's hooks).
Stabulation of the animals under heating lamp until awake.
Stabulation of the animals in the animalry in individual cages.
Sacrifice of the Animals
7 days after ischemia (Decapitation or overdose of pentobarbital).
Sampling of the brain.
Histological Parameters
Freezing of the brain in isopentane (–20° C.)
Slicing of the hippocampus using a cryo-microtome (20 $\mu$m).
Staining with cresyl violet and/or TUNEL method
Evaluation of the lesions (in CA1/CA2 subfields of the hippocampus)
Gerhard & Boast score modified or
Cell counting in the CA1/CA2
Biochemical Parameters
Microdissection of the cerebral structures
Parameters determined: DNA fragmentation, lactate, calcium penetration.
Analytical methods: ELISA, colorimetry, enzymology, radiometry.

—2—TREATMENT
Administration of the test article or the vehicle: 15 min after reperfusion (5–10 min after the recovery of the anesthesia).
Standard protocol
50 animals : 5 groups of 10 (group A: control, groups B-D: test article at 3 doses and group E : reference compound (ketamine 3×120 mg/kg, ip or Orotic acid 3×300 mg/kg, ip).

By using for instance compounds (1) or (139) at a concentration of 30 mg/kg in the above assay, a protection rate of cell survival of about 45% or 55%, respectively, were determined. According to a preferred embodiment, the tested compounds display a protection rate of at least 25%, preferably of at least 40%.

The compounds of the present invention were also subjected to the transient model of focal cerebral ischemia. The method used was adapted from Nagasawa and Kogure, Stroke, 20, 1037, 1989 as well as Zea Longa, Weinstein, Carlon and Cummins, Stroke, 20, 84, 1989. Thus, the focal ischemia assay conducted by transient middle cerebral artery occlusion in male Wistar rats after administration of compound (1) shows a decrease in the cortex infarct volume of about 56% at a dose of 1 mg/kg (i.v.)

The compounds of the present invention were also subjected to the model of kainate-induced neuronal cell death in the rat hippocampus. The method used was adapted from Gelowitz, Paterson, Pharmacol.Biochem.Behav., 62: 255–62 (1999), Magyar et al. Transm.Suppl., 52: 109–23 (1998) as well as Sperk et al, Brain Re., 338: 289–95 (1985). Thus, the kainate assay conducted in male Wistar rats after administration of compound (1) shows protection rate of about 50% at a dose of 30 mg/kg (i.v.). According to a preferred embodiment, the tested compounds display a protection rate of at least 25%, preferably of at least 40% at a dose of 30 mg/kg (i.v.)

What is claimed is:

1. An amine according to formula I:

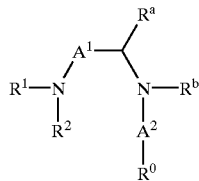

wherein
- $A^1$ and $A^2$ are selected independently from each other from the group consisting of —C(O)— and —SO$_2$—;
- $R^a$ is $C_1$–$C_{10}$ alkyl $R^b$ is CH$_3$, or $R^a$ and $R^b$ taken together with the atoms to which they are attached form a five-membered saturated ring optionally containing a sulfur atom or a six-membered saturated ring optionally fused with an aryl or heteroaryl group;
- $R^1$ is either H or $C_1$–$C_6$ alkyl;
- $R^2$ is —(R$^d$—X$_1$)$_m$—R$^e$ wherein m is an integer from 0 to 8;
- wherein $R^d$ is aryl, heteroaryl, $C_1$–$C_{18}$ alkyl, 3–8-membered cycloalkyl, $C_2$–$C_{18}$ alkenyl, 3–8-membered cycloalkenyl, $C_2$–$C_{18}$ alkynyl;
- $X_1$ is a bond, O, NH, NR$^g$, NR$^g$N$^{g'}$, S, Si(R$^g$R$^{g'}$), SO, SO$_2$, wherein R$^g$ and R$^{g'}$ are independently substituted or unsubstituted $C_1$–$C_6$ alkyl, $C_2$–$C_8$ alkenyl, $C_2$–$C_8$ alkynyl, aryl or heteroaryl;
- $R^e$ is aryl-$C_1$–$C_{18}$ alkyl, aryl-$C_2$–$C_{18}$ alkenyl, aryl-$C_2$–$C_{18}$ alkynyl, heteroaryl-$C_1$–$C_{18}$ alkyl, heteroaryl-$C_2$–$C_{18}$ alkenyl, heteroaryl-$C_2$–$C_{18}$ alkynyl, $C_1$–$C_{18}$ alkyl, $C_2$–$C_{18}$ alkenyl, $C_2$–$C_{18}$ alkynyl, wherein said $C_1$–$C_{18}$ alkyl, $C_2$–$C_{18}$ alkenyl and $C_2$–$C_{18}$ alkynyl have a terminal substituent of the formula —NRR' or —N$^+$RR'R" wherein R, R', R" are H, $C_1$–$C_6$-alkyl; or
- $R^1$ and $R^2$ together with the N atom to which they are attached form an unsubsituted or substituted 4–12 membered unsaturated or saturated ring containing one further heteroatom selected from the group consisting of O, and N optionally substituted by R$^e$, or
- $R^1$ and $R^2$ together with the N atom to which they are attached form an unsubsituted or substituted 4–12 membered unsaturated or saturated ring substituted by R$^e$, or by a substituent of the formula —NRR' or —N$^+$RR'R" wherein R, R', R" are H, $C_1$–$C_6$-alkyl;
- $R^0$ is R$^f$—X$_2$—R$^{f'}$ wherein
- $R^f$ and $R^{f'}$ are independently from each other aryl, heteroaryl, 3–8-membered cycloalkenyl, 3–8-membered cycloalkyl, $C_2$–$C_{18}$ alkyl, $C_2$–$C_{18}$alkenyl, $C_2$–$C_{18}$ alkynyl, aryl-$C_1$–$C_{18}$ alkyl, aryl-$C_2$–$C_{18}$ alkenyl, aryl-$C_2$–$C_{18}$ alkynyl, heteroaryl-$C_1$–$C_{18}$ alkyl, heteroaryl-$C_2$–$C_{18}$ alkenyl, or heteroaryl-$C_2$–$C_{18}$ alkynyl;
- $X_2$ is a bond, O, S, Si(R$^g$R$^{g'}$), SO, or SO$_2$;
- and geometrical isomers, optically active enantiomers, diastereomers, racemates and pharmaceutically acceptable salts thereof.

2. The amine according to claim 1, wherein A$^1$ and A$^2$ are each C═O.

3. The amine according to claim 1, wherein R$^0$ is C$_8$–C$_{18}$ alkyl.

4. The amine according to claim 1 wherein R$^e$ is an $C_{10}$–$C_{18}$ alkyl having a terminal NH$_2$ or ammonium group.

5. The amine according to claim 1 wherein R$^a$ and R$^b$ form a five-membered saturated ring optionally containing a sulfur atom, or a six-membered saturated ring wherein said ring may be fused with an unsubstituted phenyl group.

6. The amine according to claim 5 wherein said ring is pyrrolidinyl, piperidinyl, tetrahydroisoquinolinyl or 1,3-thiazolidinyl.

7. The amine according to claim 1 wherein R$^1$ is H or CH$_3$, R$^2$ is —(R$^d$—X$_1$)$_m$—R$^e$ in which R$^d$—X$_1$ is —(CH$_2$)$_2$—O— or a bond, R$^e$ is $C_1$–$C_{10}$-alkylamine, and m is 1, 2 or 3.

8. The amine derivative according to claim 7, wherein R$^2$ is a $C_2$–$C_8$ alkylamine.

9. The amine according to claim 8, wherein R$^2$ is ethylenamine, hexylenamin, heptylenamine, octylamine.

10. The amine derivative according to claim 1, wherein R$^0$ is selected from the group consisting of unsubstituted $C_4$–$C_{16}$ alkyl, a $C_4$–$C_{16}$ alkyl having a terminal cyclohexyl group, —CH$_2$-phenyl-O—CH$_2$-phenyl and —CH$_2$—Ph—Ph.

11. The amine derivative according to claim 10, wherein R$^0$ is dodecacyl.

12. The amine derivative according to claim 1, wherein R$^a$ and R$^b$ form a five-membered saturated ring which may contain a sulfur atom or a six-membered saturated ring optionally fused with an unsubstituted phenyl group, A$^1$ and A$^2$ are each C═O, R$^0$ is an unsubstituted $C_4$–$C_{16}$alkyl having optionally a terminal cyclohexyl group or —CH$_2$—Ph—O—CH$_2$—Ph or CH$_2$—Ph—Ph, R$^1$ is H or —CH$_3$, R$^2$ is —(R$^d$—X$_1$)$_m$—R$^e$ wherein R$^d$—X$_1$ is —(CH$_2$)$_2$—O— with m being 0 or 2, R$^e$ is an unsubstituted $C_2$–$C_8$-alkylamine.

13. The amine according to claim 12, wherein R$^e$ is $C_2$–$C_7$ alkylamine.

14. The amine derivative according to claim 1 wherein R$^a$ and R$^b$ form a piperidinyl, pyrrolidinyl or thiazolidinyl ring optionally fused with an un-substituted phenyl group, A$^1$ and A$^2$ are each C═O, R$^0$ is an unsubstituted $C_4$ or $C_{12}$ alkyl chain, R$^1$ is H or CH$_3$, R$^2$ is —(R$^d$—X$_1$)$_m$—R$^e$ wherein m is 0 and R$^e$ is $C_2$–$C_8$ alkylamine.

15. The amine derivative according to claim 1 wherein R$^b$ is CH$_3$, R$^a$ is iPr, A$^1$ and A$^2$ are each C═O, R$^0$ is $C_4$–$C_{15}$ alkyl, R$^1$ is H, R$^2$ is —(R$^d$—X$_1$)$_m$—R$^e$ wherein m is 0, R$^e$ is $C_4$–$C_{10}$.

16. The amine derivative according to claim 1 selected from the group consisting of:
- (S)-N-(6-Aminohexyl)-1-tridecanoylpiperidine-2-carboxamide,
- (R)-N-(6-Aminohexyl)-1-tridecanoylpiperidine-2-carboxamide,
- (±)-N-(6-Aminohexyl)-1-{[(2-{[2-(methyloxy)ethyl]oxy}ethyl)oxy]acetyl}-piperidine-2-carboxamide,
- (±)-N-(6-Aminohexyl)-1-(4-cyclohexylbutanoyl)piperidine-2-carboxamide,
- (±)-N-(6-Aminohexyl)-1-([1,1'-biphenyl]-4-ylacetyl)piperidine-2-carboxamide,
- (±)-N-(6-Aminohexyl)-1-({4-[(phenylmethyl)oxy]phenyl}acetyl)piperidine-2-carboxamide
- (S)-N-(6-Aminohexyl)-1-tridecanoylpyrrolidine-2-carboxamide,
- (±)-N-(6-Aminohexyl)-1-{[(2-{[2-(methyloxy)ethyl]oxy}ethyl)oxy]acetyl}-pyrrolidine-2-carboxamide,
- (±)-N-(6-Aminohexyl)-1-(4-cyclohexylbutanoyl)pyrrolidine-2-carboxamide,
- (±)-N-(6-Aminohexyl)-1-([1,1'-biphenyl]-4-ylacetyl)pyrrolidine-2-carboxamide, (±)-N-(6-Aminohexyl)-1-({4-[(phenylmethyl)oxy]phenyl}acetyl)pyrrolidine-2-carboxamide, (±)-N-(6-Aminohexyl)-3-tridecanoyl-1,3-thiazolidine-4-carboxamide, (±)-N-(6-Aminohexyl)-3-{[(2-{[2-(methyloxy)ethyl]oxy}ethyl)oxy]acetyl}-1,3-thiazolidine-4-carboxamide, (±)-N-(6-Aminohexyl)-3-(4-cyclohexylbutanoyl)-1,3-thiazolidine-4-carboxamide, (±)-N-(6-Aminohexyl)-3-([1,1'-biphenyl]4-ylacetyl)-1,3-thiazolidine-4-carboxamide, (±)-N-(6-Aminohexyl)-3-({4-[(phenylmethyl)oxy]phenyl}acetyl)-1,3-thiazolidine-4-carboxamide, (±)-N-(6-Aminohexyl)-2-tridecanoyl-1,2,3,4-tetrahydroisoquinoline-3-carboxamide, (±)-N-(6-Aminohexyl)-2-{[(2-{[2-(methyloxy)ethyl]oxy}ethyl)oxy]acetyl}-1,2,3,4-tetrahydroisoquinoline-3-carboxamide, (±)-N-(6-Aminohexyl)-2-(4-cyclohexylbutanoyl)-1,2,3,4-tetrahydroisoquinoline-3-carboxamide, (±)-N-(6-Aminohexyl)-2-([1,1'-biphenyl]-4-ylacetyl)-1,2,3,4-tetra-hydroisoquinoline-3-carboxamide, (±)-N-(6-Aminohexyl)-2-({4-[(phenylmethyl)oxy]phenyl}acetyl)-1,2,3,4 tetra-hydroisoquinoline-3-carboxamide, (S)-N-(1-{[(6-Aminohexyl)amino]carbonyl}-2-methylpropyl)-N-methyltridecanamide, (±)-N-(6-Aminohexyl)-11-methyl-12-(1-methylethyl)-10-oxo-2,5,8-trioxa-11-azatridecan-13-amide, (±)-N-(6-Aminohexyl)-2-[(4-cyclohexylbutanoyl)(methyl)amino]-3-methylbutanamide, (±)-N-(6-Aminohexyl)-2-[([1,1'-biphenyl]-4-ylacetyl)(methyl)amino]-3-methyl-butanamide, (±)-N-(6-Aminohexyl)-3-methyl-2-[methyl({4-[(phenylmethyl)oxy]phenyl}-acetyl)amino]butanamide, (±)-N-(5-Aminopentyl)-1-tridecanoylpiperidine-2-carboxamide, (±)-N-(5-Aminopentyl)-1-{[(2-{[2-(methyloxy)ethyl]oxy}ethyl)oxy]acetyl}-piperidine-2-carboxamide, (±)-N-(5-Aminopentyl)-1-(4-cyclohexylbutanoyl)piperidine-2-carboxamide, (±)-N-(5-Aminopentyl)-1-([1,1'-biphenyl]-4-ylacetyl)piperidine-2-carboxamide, (±)-N-(5-Aminopentyl)-1-({4-[(phenylmethyl)oxy]phenyl}acetyl)piperidine-2-carboxamide, (±)-N-(5-Aminopentyl)-1-tridecanoylpyrrolidine-2-carboxamide, (±)-N-(5-Aminopentyl)-1-{[(2-{[2-(methyloxy)ethyl]oxy}ethyl)oxy]acetyl}-pyrrolidine-2-carboxamide, (±)-N-(5-Aminopentyl)-1-(4-cyclohexylbutanoyl)pyrrolidine-2-carboxamide, (±)-N-(5-Aminopentyl)-1-([1,1'-biphenyl]-4-ylacetyl)pyrrolidine-2-carboxamide, (±)-N-(5-Aminopentyl)-1-({4-[(phenylmethyl)oxy]phenyl}acetyl)pyrrolidine-2-carboxamide, (±)-N-(5-Aminopentyl)-3-tridecanoyl-1,3-thiazolidine-4-carboxamide, (±)-N-(5-Aminopentyl)-3-{[(2-{[2-(methyloxy)ethyl]oxy}ethyl)oxy]acetyl}-1,3-thiazolidine-4-carboxamide, (±)-N-(5-Aminopentyl)-3-(4-cyclohexylbutanoyl)-1,3-thiazolidine-4-carboxamide, (±)-N-(5-Aminopentyl)-3-([1,1'-biphenyl]-4-ylacetyl)-1,3-thiazolidine-4-carboxamide, (±)-N-(5-Aminopentyl)-3-({4-[(phenylmethyl)oxy]phenyl}acetyl)-1,3-thiazolidine-4-carboxamide, (±)-N-(5-Aminopentyl)-2-tridecanoyl-1,2,3,4-tetrahydroisoquinoline-3-carboxamide, (±)-N-(5-Aminopentyl)-2-{[(2-{[2-(methyloxy)ethyl]oxy}ethyl)oxy]acetyl}-1,2,3,4-tetrahydroisoquinoline-3-carboxamide (±)-N-((5-Aminopentyl)-2-(4-cyclohexylbutanoyl)-1,2,3,4-tetrahydroisoquinoline-3-carboxamide, (±)-N-(5-Aminopentyl)-2-([1,1'-biphenyl]-4-ylacetyl)-1,2,3,4-tetrahydroisoquinoline-3-carboxamide, (±)-N-(5-Aminopentyl)-2-({4-[(phenylmethyl)oxy]phenyl}acetyl)-1,2,3,4-tetra-hydroisoquinoline-3-carboxamide, (±)-N-(1-{[(5-Aminopentyl)amino]carbonyl}-2-methylpropyl)-N-methyltridecanamide, (±)-N-(5-Aminopentyl)-11-methyl-12-(1-methylethyl)-10-oxo-2,5,8-trioxa-11-azatridecan-13-amide, (±)-N-(5-Aminopentyl)-2-[(4-cyclohexylbutanoyl)(methyl)amino]-3-methylbutanamide, (±)-N-(5-Aminopentyl)-2-[([1,1'-biphenyl]-4-ylacetyl)(methyl)amino]-3-methyl-butanamide, (±)-N-(5-Aminopentyl)-3-methyl-2-[methyl({4-[(phenylmethyl)oxy]phenyl}acetyl)-amino]butanamide, (±)-N-(7-Aminoheptyl)-1-tridecanoylpiperidine-2-carboxamide, (±)-N-(7-Aminoheptyl)-1-{[(2-{[2-(methyloxy)ethyl]oxy}ethyl)oxy]acetyl}-piperidine-2-carboxamide, (±)-N-(7-Aminoheptyl)-1-(4-cyclohexylbutanoyl)piperidine-2-carboxamide, (±)-N-(7-Aminoheptyl)-1-([1,1'-biphenyl-4]-ylacetyl)piperidine-2-carboxamide, (±)-N-(7-Aminoheptyl)-1-({4-[(phenylmethyl)oxy]phenyl }acetyl)piperidine-2-carboxamide, (±)-N-(7-Aminoheptyl)-1-tridecanoylpyrrolidine-2-carboxamide (±)-N-(7-Aminoheptyl)-1-{[(2-{[2-(methyloxy)ethyl]oxy}ethyl)oxy]acetyl}pyrrolidine-2-carboxamide, (±)-N-(7-Aminoheptyl)-1-(4-cyclohexylbutanoyl)pyrrolidine-2-carboxamide, (±)-N-(7-Aminoheptyl)-1-([1,1'-biphenyl]-4-ylacetyl)pyrrolidine-2-carboxamide, (±)-N-(7-Aminoheptyl)-1-({4-[(phenylmethyl)oxy]phenyl}acetyl)pyrrolidine-2-carboxamide, (±)-N-(7-Aminoheptyl)-3-tridecanoyl-1,3-thiazolidine-4-carboxamide, (±)-N-(7-Aminoheptyl)-3-{[(2-{[2-(methyloxy)ethyl]oxy}ethyl)oxy]acetyl}-1,3-thiazolidine-4-carboxamide, (±)-N-(7-Aminoheptyl)-3-(4-cyclohexylbutanoyl)-1,3-thiazolidine-4-carboxamide, (±)-N-(7-Aminoheptyl)-3-([1,1'-biphenyl]-4-ylacetyl)-1,3-thiazolidine-4-carboxamide, (±)-N-(7-Aminoheptyl)-3-({4-[(phenylmethyl)oxy]phenyl }acetyl)-1,3-thiazolidine-4-carboxamide, (±)-N-(7-Aminoheptyl)-2-tridecanoyl-1,2,3,4-tetrahydroisoquinoline-3-carboxamide, (±)-N-(7-Aminoheptyl)-2-{[(2-{[2-(methyloxy)ethyl]oxy}ethyl)oxy]acetyl}-1,2,3,4-tetrahydroisoquinoline-3-carboxamide, (±)-N-(7-Aminoheptyl)-2-(4-cyclohexylbutanoyl)-1,2,3,4-tetrahydroisoquinoline-3-carboxamide, (±)-N-(7-Aminoheptyl)-2-([1,1'-biphenyl]-4-ylacetyl)-1,2,3,4-tetrahydroisoquinoline-3-carboxamide, (±)-N-(7-Aminoheptyl)-2-({4-[(phenylmethyl)oxy]phenyl}acetyl)-1,2,3,4-tetra-hydroisoquinoline-3-carboxamide, (±)-N-(1-{[(7-Aminoheptyl)amino]carbonyl}-2-methylpropyl)-N-methyltridecanamide, (±)-N-(7-Aminoheptyl)-11-methyl-12-(1-methylethyl)-10-oxo-2,5,8-trioxa-11-azatridecan-13-amide (±)-N-(7-Aminoheptyl)-2-[(4-cyclohexylbutanoyl)(methyl)amino]-3-methyl-butanamide, (±)-N-(7-Aminoheptyl)-2-[([1,1'-biphenyl]-4-ylacetyl)(methyl)amino]-3-methylbutanamide, (±)-N-(7-Aminoheptyl)-3-methyl-2-[methyl({4-[(phenylmethyl)oxy]phenyl}-acetyl)amino]butanamide, (±)-N-[2-({2-[(2-Aminoethyl)oxy]ethyl}oxy)ethyl]-1-tridecanoylpiperidine-2-carboxamide, (±)-N-[2-({2-[(2-Aminoethyl)oxy]ethyl}oxy)ethyl]-1-{[(2-{[2-(methyloxy)-ethyl]oxy}ethyl)oxy]acetyl}piperidine-2-carboxamide, (±)-N-[2-({2-[(2-Aminoethyl)oxy]ethyl}oxy)ethyl]-1-(4-cyclohexylbutanoyl)-piperidine-2-carboxamide, (±)-N-[2-({2-[(2-Aminoethyl)oxy]ethyl}oxy)ethyl]-1-([1,1'-biphenyl]-4-ylacetyl)-piperidine-2-carboxamide, (±)-N-[2-({2-[(2-Aminoethyl)oxy]ethyl}oxy)ethyl]-1-({4-[(phenylmethyl)oxy]-phenyl}acetyl)piperidine-2-carboxamide, (±)-N-[2-({2-[(2-Aminoethyl)oxy]ethyl}oxy)ethyl]-1-tridecanoylpyrrolidine-2-carboxamide, (±)-N-[2-({2-[(2-Aminoethyl)oxy]ethyl}oxy)ethyl]-1-{[(2-{[2-(methyloxy)ethyl]oxy}ethyl)oxy]acetyl}pyrrolidine-2-carboxamide, (±)-N-[2-({2-[(2-Aminoethyl)oxy]ethyl}oxy)ethyl]-1-(4-cyclohexylbutanoyl)-pyrrolidine-2-carboxamide, (±)-N-[2-({2-[(2-Aminoethyl)oxy]ethyl}oxy)ethyl]-1-([1,1'-biphenyl]-4-ylacetyl)pyrrolidine-2-carboxamide, (±)-N-[2-({2-[(2-Aminoethyl)oxy]ethyl}oxy)ethyl]-1-({4-[(phenylmethyl)oxy]-phenyl}acetyl)pyrrolidine-2-carboxamide, (±)-N-[2-({2-[(2-Aminoethyl)oxy]ethyl}oxy)ethyl]-3-tridecanoyl-1,3-thiazolidine-4-carboxamide, (±)-N-[2-({2-[(2-Aminoethyl)oxy]ethyl}oxy)ethyl]-3-{[(2-{[2-(methyloxy)ethyl]-oxy}-ethyl)oxy]acetyl}-1,3-thiazolidine-4-carboxamide, (±)-N-[2-({2-[(2-Aminoethyl)oxy]ethyl}oxy)ethyl]-3-(4-cyclohexylbutanoyl)-1,3-thiazolidine-4-carboxamide, (±)-N-[2-({2-[(2-Aminoethyl)oxy]ethyl}oxy)ethyl]-3-([1,1'-biphenyl]-4-ylacetyl)-1,3-thiazolidine-4-carboxamide, (±)-N-[2-({2-[(2-Aminoethyl)oxy]ethyl}oxy)ethyl]-3-({4-[(phenylmethyl)oxy]-phenyl}acetyl)-1,3-thiazolidine-4-carboxamide, (±)-N-[2-({2-[(2-Aminoethyl)oxy]ethyl}oxy)ethyl]-2-tridecanoyl-1,2,3,4-tetra-hydroisoquinoline-3-carboxamide, (±)-N-[2-({2-[(2-Aminoethyl)oxy]ethyl}oxy)ethyl]-2-{[(2-{[2-(methyloxy)ethyl]oxy}-ethyl)oxy]acetyl}-1,2,3,4-tetrahydroisoquinoline-3-carboxamide, (±)-N-[2-({2-[(2-Aminoethyl)oxy]ethyl}oxy)ethyl]-2-(4-cyclohexylbutanoyl)-1,2,3,4-tetrahydroisoquinoline-3-carboxamide, (±)-N-[2-({2-[(2-Aminoethyl)oxy]ethyl}oxy)ethyl]-2-([1,1'-biphenyl]-4-ylacetyl)-1,2,3,4-tetrahydroisoquinoline-3-carboxamide, (±)-N-[2-({2-[(2-Aminoethyl)oxy]ethyl}oxy)ethyl]-2-({4-[(phenylmethyl)oxy]-phenyl}acetyl)-1,2,3,4-tetrahydroisoquinoline-3-carboxamide, (±)-N-[1-({[2-({2-[($^2$-Aminoethyl)oxy]ethyl}oxy)ethyl]amino}carbonyl)-2-methyl-propyl]-N-methyltridecanamide, (±)-N-[2-({2-[(2-Aminoethyl)oxy]ethyl}oxy)ethyl]-11-methyl-12-(1-methylethyl)-10-oxo-2,5,8-trioxa-11-azatridecan-13-amide, (±)-N-[2-({2-[(2-Aminoethyl)oxy]ethyl}oxy)ethyl]-2-[(4-cyclohexylbutanoyl)-(methyl)-amino]-3-methylbutanamide, (±)-N-[2-({2-[(2-Aminoethyl)oxy]ethyl}oxy)ethyl]-2-[([1,1'-biphenyl]-4-ylacetyl)(methyl)-amino]-3-methylbutanamide, (±)-N-[2-({2-[(2-Aminoethyl)oxy]ethyl}oxy)ethyl]-3-methyl-2-[methyl({4-[(phenylmethyl)oxy]phenyl}acetyl)amino]butanamide, (±)-N-Methyl-N-(2-{[2-(methylamino)ethyl]oxy}ethyl)-1-{[(2-{[2-(methyloxy)-ethyl]-oxy}ethyl)oxy]acetyl}piperidine-2-carboxamide, (±)-N-Methyl-N-(2-{[2-(methylamino)ethyl]oxy}ethyl)-1-tridecanoylpyrrolidine-2-carboxamide, (±)-N-Methyl-N-(2-{[2-(methylamino)ethyl]oxy}ethyl)-1-{[(2-{[2-(methyloxy)-ethyl]oxy}ethyl)oxy]acetyl}pyrrolidine-2-carboxamide, (±)-1-(4-Cyclohexylbutanoyl)-N-methyl-N-(2-{[2-(methylamino)ethyl]oxy}ethyl)-pyrrolidine-2-carboxamide, (±)-1-([1,1'-Biphenyl]-4-ylacetyl)-N-methyl-N-(2-{[2-(methylamino)ethyl]oxy}-ethyl)-pyrrolidine-2-carboxamide, (±)-N-Methyl-N-(2-{[2-(methylamino)ethyl]oxy}ethyl)-1-({4-[(phenylmethyl)oxy]-phenyl}acetyl)pyrrolidine-2-carboxamide, (±)-N-Methyl-N-(2-{[2-(methylamino)ethyl]oxy}ethyl)-3-tridecanoyl-1,3-thiazolidine-4-carboxamide, (±)-N-Methyl-N-(2-{[2-(methylamino)ethyl]oxy}ethyl)-3-{[(2-{[2-(methyloxy)-ethyl]oxy}ethyl)oxy]acetyl}-1,3-thiazolidine-4-carboxamide, (±)-3-(4-Cyclohexylbutanoyl)-N-methyl-N-(2-{[2-(methylamino)ethyl]oxy}ethyl)-1,3-thiazolidine-4-carboxamide, (±)-3-([1,1'-Biphenyl]-4-ylacetyl)-N-methyl-N-(2-{[2-(methylamino)ethyl]oxy}-ethyl)-1,3-thiazolidine-4-carboxamide, (±)-N-Methyl-N-(2-{[2-(methylamino)ethyl]oxy}ethyl)-3-({4-[(phenylmethyl)oxy]-phenyl}acetyl)-1,3-thiazolidine-4-carboxamide, (±)-N-Methyl-N-(2-{[2-(methylamino)ethyl]oxy}ethyl)-2-tridecanoyl-1,2,3,4-tetrahydroisoquinoline-3-carboxamide, (±)-N-Methyl-N-(2-{[2-(methylamino)ethyl]oxy}ethyl)-2-{[(2-{[2-(methyloxy)-ethyl]oxy}-ethyl)oxy]acetyl}-1,2,3,4-tetrahydroisoquinoline-3-carboxamide, (±)-2-(4-Cyclohexylbutanoyl)-N-methyl-N-(2-{[2-(methylamino)ethyl]oxy}ethyl)-1,2,3,4-tetrahydroisoquinoline-3-carboxamide, (±)-2-([1,1'-Biphenyl-4-ylacetyl)-N-methyl-N-(2-{[2-(methylamino)ethyl]oxy}-ethyl)-1,2,3,4-tetrahydroisoquinoline-3-carboxamide, (±)-N-Methyl-N-(2-{[2-(methylamino)ethyl]oxy}ethyl)-2-({4-[(phenylmethyl)oxy]-phenyl}acetyl)-1,2,3,4-tetrahydroisoquinoline-3-carboxamide, (±)-N,11-Dimethyl-N-(2-{[2-(methylamino)ethyl]oxy}ethyl)-12-(1-methylethyl)-10-oxo-2,5,8-trioxa-11-azatridecan-13-amide, (±)-N-Methyl-N-[6-(methylamino)hexyl]-1-{[(2-{[2-(methyloxy)ethyl]oxy}-ethyl)oxy]acetyl}piperidine-2-carboxamide, (±)-N-Methyl-N-[6-(methylamino)hexyl]-1-tridecanoylpyrrolidine-2-carboxamide, (±)-N-Methyl-N-[6-(methylamino)hexyl]-1-{[(2-{[2-(methyloxy)ethyl]oxy}ethyl)-oxy]acetyl}pyrrolidine-2-carboxamide, (±)-1-(4-Cyclohexylbutanoyl)-N-methyl-N-[6-(methylamino)hexyl]pyrrolidine-2-carboxamide, (±)-1-([1,1'-Biphenyl]-4-ylacetyl)-N-methyl-N-[6-(methylamino)hexyl]pyrrolidine-2-carboxamide, (±)-N-Methyl-N-[6-(methylamino)hexyl]-1-({4-[(phenylmethyl)oxy]phenyl}-acetyl)pyrrolidine-2-carboxamide, (±)-N-Methyl-N-[6-(methylamino)hexyl]-3-tridecanoyl-1,3-thiazolidine-4-carboxamide, (±)-N-Methyl-N-[6-(methylamino)hexyl]-3-{[(2-{[2-(methyloxy)ethyl]oxy}-ethyl)oxy]acetyl}-1,3-thiazolidine-4-carboxamide, (±)-3-(4-Cyclohexylbutanoyl)-N-methyl-N-[6-(methylamino)hexyl]-1,3-thiazolidine-4-carboxamide, (±)-3-([1,1'-Biphenyl]-4-ylacetyl)-N-methyl-N-[6-(methylamino)hexyl]-1,3-thiazolidine-4-carboxamide, (±)-N-Methyl-N-[6-(methylamino)hexyl]-3-({4-[(phenylmethyl)oxy]phenyl}-acetyl)-1,3-thiazolidine-4-carboxamide, (±)-N-Methyl -N-[6-(methylamino)hexyl]-2-tridecanoyl-1,2,3,4-tetrahydroisoquinoline-3-carboxamide, (±)-N-Methyl-N-[6-(methylamino)hexyl]-2-{[(2-{[2-(methyloxy)ethyl]oxy}-ethyl)oxy]-acetyl}-1,2,3,4-tetrahydroisoquinoline-3-carboxamide, (±)-2-(4-Cyclohexylbutanoyl)-N-methyl-N-[6-(methylamino)hexyl]-1,2,3,4-tetrahydroisoquinoline-3-carboxamide, (±)-2-([1,1'-Biphenyl]-4-ylacetyl)-N-methyl-N-[6-(methylamino)hexyl]-1,2,3,4-tetrahydroisoquinoline-3-carboxamide, (±)-N-Methyl-N-[6-(methylamino)hexyl]-2-({4-[(phenylmethyl)oxy]phenyl}-acetyl)-1,2,3,4-tetrahydroisoquinoline-3-carboxamide, (±)-N, 11-Dimethyl-N-[6-(methylamino)hexyl]-12-(1-methylethyl)-10-oxo-2,5,8-trioxa-11-azatridecan-13-amide, (±)-N-(6-Aminohexyl)-1-pentanoylpiperidine-2-carboxamide, (±)-N-(2-Aminoethyl)-1-pentanoylpiperidine-2-carboxamide, (R)-1-Undecanoyl-piperidine-2-carboxylic acid (5-amino-pentyl)-amide, (S)-1-Undecanoyl-piperidine-2-carboxylic acid (5-amino-pentyl)-amide, (R)-1-Undecanoyl-piperidine-2-carboxylic acid (3-amino-propyl)-amide, (S)-1-Undecanoyl-piperidine-2-carboxylic acid (3-amino-propyl)-amide, (R)-1-Nonanoyl-piperidine-2-carboxylic acid (5-amino-pentyl)-amide, (S)-1-Nonanoyl-piperidine-2-carboxylic acid (5-amino-pentyl)-amide, (R)-1-Nonanoyl-piperidine-2-carboxylic acid (3-amino-propyl)-amide, (S)-1-Nonanoyl-piperidine-2-carboxylic acid (3-amino-propyl)-amide, (R)-1-Octanoyl-piperidine-2-carboxylic acid (5-amino-pentyl)-amide, (S)-1-Octanoyl-piperidine-2-carboxylic acid (5-amino-pentyl)-amide, (R)-1-Octanoyl-piperidine-2-carboxylic acid (3-amino-propyl)-amide, (S)-1-Octanoyl-piperidine-2-carboxylic acid (3-amino-propyl)-amide, (R)-1-Hexanoyl-piperidine-2-carboxylic acid (5-amino-pentyl)-amide, (S)-1-Hexanoyl-piperidine-2-carboxylic acid (5-amino-pentyl)-amide, (R)-1-Hexanoyl-piperidine-2-carboxylic acid (3-amino-propyl)-amide, (S)-1-Hexanoyl-piperidine-2-carboxylic acid (3-amino-propyl)-amide, (R)-1-(2-Biphenyl-4-yl-ethanoyl)-piperidine-2-carboxylic acid (5-amino-pentyl)-amide, (R)-1-(1-Biphenyl-4-yl-methanoyl)-piperidine-2-carboxylic acid (5-amino-pentyl)-amide, (R)-1-Undecanoyl-piperidine-2-carboxylic acid (4-diethylamino-butyl)-amide, (R)-1-Undecanoyl-piperidine-2-carboxylic acid (3-dimethylamino-propyl)-amide, (R)-1-(Decane-1-sulfonyl)-piperidine-2-carboxylic acid (5-amino-pentyl)-amide, (R)-1-(Decane-1-sulfonyl)-piperidine-2-carboxylic acid (3-amino-propyl)-amide, (R)-1-Undecanoyl-pyrrolidine-2-carboxylic acid (5-amino-pentyl)-amide, (S)-1-Undecanoyl-pyrrolidine-2-carboxylic acid (5-amino-pentyl)-amide, (R)-1-Undecanoyl-pyrrolidine-2-carboxylic acid (3-amino-propyl)-amide, (S)-1-Undecanoyl-pyrrolidine-2-carboxylic acid (3-amino-propyl)-amide, (R)-1-Nonanoyl-pyrrolidine-2-carboxylic acid (5-amino-pentyl)-amide, (S)-1-Nonanoyl-pyrrolidine-2-carboxylic acid (5-amino-pentyl)-amide, (R)-1-Nonanoyl-pyrrolidine-2-carboxylic acid (3-amino-propyl)-amide, (S)-1-Nonanoyl-pyrrolidine-2-carboxylic acid (3-amino-propyl)-amide, (R)-1-Octanoyl-pyrrolidine-2-carboxylic acid (5-amino-pentyl)-amide, (S)-1-Octanoyl-pyrrolidine-2-carboxylic acid (5-amino-pentyl)-amide, (R)-1-Octanoyl-pyrrolidine-2-carboxylic acid (3-amino-propyl)-amide, (S)-1-Octanoyl-pyrrolidine-2-carboxylic acid (3-amino-propyl)-amide, (R)-1-Hexanoyl-pyrrolidine-2-carboxylic acid (5-amino-pentyl)-amide, (S)-1-Hexanoyl-pyrrolidine-2-carboxylic acid (5-amino-pentyl)-amide, (R)-1-Hexanoyl-pyrrolidine-2-carboxylic acid (3-amino-propyl)-amide, (S)-1-Hexanoyl-pyrrolidine-2-carboxylic acid (3-amino-propyl)-amide, (R)-1-(2-Biphenyl-4-yl-ethanoyl)-pyrrolidine-2-carboxylic acid (5-amino-pentyl)-amide, (R)-1-(1-Biphenyl-4-yl-methanoyl)-pyrrolidine-2-carboxylic acid (5-amino-pentyl)-amide, (R)-1-Undecanoyl-pyrrolidine-2-carboxylic acid (4-diethylamino-butyl)-amide, (R)-1-Undecanoyl-pyrrolidine-2-carboxylic acid (3-dimethylamino-propyl)-amide, (R)-1-(Decane-1-sulfonyl)-pyrrolidine-2-carboxylic acid (5-amino-pentyl)-amide, (R)-1-(Decane-1-sulfonyl)-pyrrolidine-2-carboxylic acid (3-amino-propyl)-amide, (R)-N-(5-Aminopentyl)-methyl-C-(methyl-undecanoyl-amino)-butyramide, (R)-N-(3-Aminopropyl)-methyl-C-(methyl-undecanoyl-amino)-butyramide, (R)-N-(5-Aminopentyl)-methyl-C-(methyl-nonanoyl-amino)-butyramide, (R)-N-(5-Aminopentyl)-methyl-C-(methyl-octanoyl-amino)butyramide.

17. The amine according to claim 16, which is selected from the group consisting of:

(S)-1-Tridecanoyl-piperidine-2-carboxylic acid (6-amino-hexyl)-amide, (R)-1-Tridecanoyl-piperidine-2-carboxylic acid (6-amino-hexyl)-amide, (S)-N-(6-Aminohexyl)-1-tridecanoylpyrrolidine-2-carboxamide, (R)-N-(6-Aminohexyl)-1-tridecanoylpyrrolidine-2-carboxamide, (R)-N-(6-Aminopentyl)-1-tridecanoylpyrrolidine-2-carboxamide, (S)-N-(6-Aminopentyl)-1-tridecanoylpyrrolidine-2-carboxamide, (S)-N-(1-{[(6-Aminohexyl)amino]carbonyl}-2-methylpropyl)-N-methyltridecanamide.

18. The amine derivative according to claim 1 for use as a medicament.

19. A method comprising
contacting cells expressing Bax with at least one amine according to claim 1 in an amount effective for inhibiting the expression, activity or both expression and activity of Bax.

20. A method for the treatment of disease states mediated by Bax, comprising
administering a pharmaceutically active amount of an amine according to claim 1 to a patient in need thereof.

21. A pharmaceutical composition comprising at least one amine of claim 1 and a pharmaceutically acceptable carrier, diluent or excipient.

22. A process for preparing the amine according to claim 1, comprising
reacting a compound according to the following formula IV

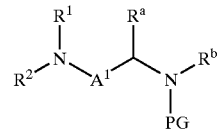

wherein PG is a protective group,
after a deprotection step, with an electrophile according to the formula $R^0—A^{2'}(=O)$, wherein $A^{2'}$ is either C—OH or S(O)—Cl.

23. The process according to claim 22, wherein $A^1$ is —C=O, and $A^{2'}$ is C—OH.

24. The amine according to claim 3, wherein $R^0$ is $C_{10-C18}$ alkyl.

25. The amine according to claim 3, wherein $R^0$ is $C_{10}-C_{12}$-alkyl.

26. The amine according to claim 10, wherein $R^0$ is $C_6-C_{14}$ alkyl.

27. The amine according to claim 13, wherein $R^e$ is hexyl amine.

28. The amine according to claim 15, wherein $R^0$ is a dodecacyl group.

29. The amine according to claim 15, wherein $R^e$ is $C_6$ alkyl amine.

30. A method comprising
administering a pharmaceutical composition comprising an amine according to formula 1 to a mammal

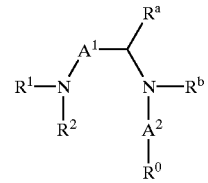

wherein
$A^1$ and $A^2$ are selected independently from each other from the group consisting of —C(O)— and —SO$_2$—;

$R^a$ is $C_1-C_{10}$ alkyl, $R^b$ is $CH_3$, or $R^a$ and $R^b$ taken together with the atoms to which they are attached form a five-membered saturated ring optionally containing a sulfur atom or a six-membered saturated ring optionally fused with an aryl or heteroaryl group;

$R^1$ is either H or $C_1-C_6$ alkyl;

$R^2$ is—$(R^d—X_1)_m$—$R^e$ wherein m is an integer from 0 to 8; wherein $R^d$ is aryl, heteroaryl, $C_1-C_{18}$ alkyl, 3–8-membered cycloalkyl, $C_2-C_{18}$ alkenyl, 3–8-membered cycloalkenyl, or $C_2-C_{18}$ alkynyl;

$X^1$ is a bond, O, NH, $NR^g$, $NR^gN^{g'}$, S, $Si(R^gR^{g'})$, SO, or $SO_2$, wherein $R^g$ and $R^{g'}$ are independently substituted or unsubstituted $C_1-C_6$ alkyl, $C_2-C_8$ alkenyl, $C_2-C_8$ alkynyl, aryl or heteroaryl;

$R^e$ is aryl-$C_1-C_{18}$ alkyl, aryl-$C_2-C_{18}$ alkenyl, aryl-$C_2-C_{18}$ alkynyl, heteroaryl-$C_1-C_{18}$ alkyl, heteroaryl-$C_2-C_{18}$ alkenyl, heteroaryl-$C_2-C_{18}$ alkynyl, $C_1-C_{18}$ alkyl, $C_2-C_{18}$ alkenyl, $C_2-C_{18}$ alkynyl, wherein said $C_1-C_{18}$ alkyl, $C_2-C_{18}$ alkenyl and $C_2-C_{18}$ alkynyl have a terminal substituent of the formula —NRR' or —N$^+$RR'R" wherein R, R', R" are H, $C_1-C_6$-alkyl; or R' and $R^2$ together with the N atom to which they are attached form an unsubstituted or substituted 4–12 membered unsaturated or saturated ring containing one further heteroatom selected from the group consisting of O and N optionally substituted by $R^e$, or $R_1$ and $R^2$ together with the N atom to which they are attached form an unsubstituted or substituted 4–12 membered unsaturated or saturated ring substituted by $R^e$, or by a substituent of the formula —NRR' or —N⁺RR'R" wherein R, R', R" are H, $C_1$–$C_6$-alkyl;

$R^0$ $R^f$—$X_2$—$R^f$ wherein $R^f$ and $R^f$ are independently from each other aryl, heteroaryl, 3–8-membered cycloalkenyl, 3–8-membered cycloalkyl, $C_2$—$C_{18}$ alkyl, $C_2$–$C_{18}$ alkenyl, $C_2$–$C_{18}$ alkynyl, aryl-$C_{1-C18}$ alkyl, aryl-$C_2$–$C_{18}$ is alkenyl, aryl-$C_2$–$C_{18}$ alkynyl, heteroaryl-$C_1$–$C_{18}$ alkyl, heteroaryl-$C_2$–$C_{18}$ alkenyl, or heteroaryl-$C_2$–$C_{18}$ alkynyl;

$X_2$ is a bond, O, S, Si($R^gR^g$), SO, or $SO_2$;

and geometrical isomers, optically active enantiomers, diastereomers, racemates and pharmaceutically acceptable salts thereof.

31. The method according to claim 30, wherein the terminal substituent of $R^e$ is —$NH_2$ or an ammonium moiety.

32. The method according to claim 30, wherein the amine is administered in an amount effect for the treatment of disorders associated with the abnormal expression or the activity of Bax by inhibition of the Bax function, inhibition of the Bax activation or both the inhibition of the Bax function and the inhibition of the Bax activation.

33. A process for preparing a pharmaceutical composition, comprising mixing the amine according to claim 1 with one or more pharmaceutically acceptable diluents or additives to form the pharmaceutical composition.

34. A method comprising administering a pharmaceutical composition comprising the amine of claim 1 in an amount effective for the treatment of a neuronal disorder selected from the group consisting of epilepsy, Alzheimer's disease, Huntington's disease, Parkinson's disease, Retinal diseases, spinal cord injury, Chron's disease, head trauma, spinocerebellar ataxias and dentatorubral-pallidoluysian atrophy.

35. A method comprising administering a pharmaceutical composition comprising the amine according to claim 1 to a human in an amount effect for the treatment of an autoimmune disease selected from the group consisting of Multiple Sclerosis, amyotrophic lateral sclerosis, retinitis pigmentosa, inflammatory bowel disease (IBD), rheumatoid arthritis, asthma, septic shock, transplant rejection and AIDS.

36. A method comprising administering a pharmaceutical composition comprising the amine according to claim 1 to a mammal in an amount effective for the treatment of ischemia, stroke myocardial infraction, reperfusion injury, cardiovascular disorders, arteriosclerosis, heart failure, heart transplantation, renal hypoxia or hepatitis.

37. A method comprising administering a pharmaceutical composition comprising the amine according to claim 1 to a mammal in an amount effective for the treatment of infertility related disorders.

38. The method of claim 37, wherein the infertility related disorder is selected from the group consisting of premature menopause, ovarian failure and follicular atresia.

39. A method comprising administering a pharmaceutical composition comprising the amine according to claim 1 to a mammal in an amount effective for the treatment of disorders associated with the abnormal expression, activity or both expression and activity of Bax by inhibition of Bax function, Bax activation or both Bax function and Bax activation.

40. The method of claim 30, wherein the pharmaceutical composition is capable of oral administration.

* * * * *